United States Patent
Schauer et al.

(10) Patent No.: US 11,116,852 B2
(45) Date of Patent: Sep. 14, 2021

(54) FRATAXIN EXPRESSION CONSTRUCTS

(71) Applicant: PRECIGEN, INC., Blacksburg, VA (US)

(72) Inventors: Stephen Schauer, Rockville, MD (US); Darby Thomas, Blacksburg, VA (US); Gregory Robinson, Cambridge, MA (US); Mark Pykett, Cambridge, MA (US); Richard Thorn, Cambridge, MA (US); Kirsten Gruis, Cambridge, MA (US)

(73) Assignee: PRECIGEN, INC., Blacksburg, VA (US)

( * ) Notice: Subject to any disclaimer, the term of this patent is extended or adjusted under 35 U.S.C. 154(b) by 261 days.

(21) Appl. No.: 15/807,350

(22) Filed: Nov. 8, 2017

(65) Prior Publication Data
US 2018/0140721 A1 May 24, 2018

Related U.S. Application Data

(60) Provisional application No. 62/419,621, filed on Nov. 9, 2016.

(51) Int. Cl.
| | | |
|---|---|---|
| *A61K 48/00* | (2006.01) | |
| *C12N 15/864* | (2006.01) | |
| *A61P 25/00* | (2006.01) | |
| *A61K 38/17* | (2006.01) | |
| *C07K 14/47* | (2006.01) | |
| *C12N 15/86* | (2006.01) | |

(52) U.S. Cl.
CPC ...... *A61K 48/0058* (2013.01); *A61K 38/1709* (2013.01); *A61K 48/005* (2013.01); *A61K 48/0066* (2013.01); *A61K 48/0075* (2013.01); *A61P 25/00* (2018.01); *C07K 14/47* (2013.01); *C12N 15/86* (2013.01); *C12N 15/8645* (2013.01); *C12N 2750/14143* (2013.01); *C12N 2830/002* (2013.01)

(58) Field of Classification Search
CPC ............ A61K 48/0058; A61K 48/0066; C12N 15/86; C12N 15/8645
See application file for complete search history.

(56) References Cited

U.S. PATENT DOCUMENTS

| | | | |
|---|---|---|---|
| 9,066,966 B2 | 6/2015 | Puccio et al. | |
| 9,217,019 B2 * | 12/2015 | Testi | C07K 14/47 |
| 9,402,919 B2 * | 8/2016 | Roeth | A61K 48/0066 |
| 9,593,330 B2 | 3/2017 | Collard et al. | |
| 9,944,906 B2 | 4/2018 | Testi | |
| 10,337,027 B2 | 7/2019 | Puccio et al. | |
| 10,548,947 B2 | 2/2020 | Samulski | |
| 10,617,770 B2 | 4/2020 | Corti et al. | |
| 2005/0196754 A1 | 9/2005 | Drmanac et al. | |
| 2007/0060743 A1 | 3/2007 | Tang et al. | |
| 2014/0135275 A1 | 5/2014 | Keefe et al. | |
| 2016/0024526 A1 | 1/2016 | Puccio et al. | |
| 2016/0243260 A1 | 8/2016 | Blits | |
| 2017/0166925 A1 | 6/2017 | Gao et al. | |
| 2018/0021364 A1 | 1/2018 | Stewart et al. | |
| 2018/0050117 A1 | 2/2018 | Puccio et al. | |
| 2018/0245073 A1 | 8/2018 | Kotin et al. | |
| 2018/0334687 A1 | 11/2018 | Puccio et al. | |
| 2019/0038777 A1 | 2/2019 | Donsante et al. | |
| 2019/0119337 A1 | 4/2019 | Cherqui | |
| 2019/0160186 A1 | 5/2019 | Lundberg et al. | |
| 2019/0192691 A1 | 6/2019 | Barrett et al. | |
| 2020/0138975 A1 | 5/2020 | Corti et al. | |
| 2020/0157564 A1 | 5/2020 | Puccio et al. | |
| 2020/0206361 A1 | 7/2020 | Cherqui | |

FOREIGN PATENT DOCUMENTS

| | | |
|---|---|---|
| EP | 0885309 B1 | 4/2004 |
| EP | 2598525 B1 | 8/2015 |
| WO | 2016/115503 A1 | 7/2016 |

OTHER PUBLICATIONS

International Search Report and Written Opinion for PCT/US2017/060680, dated Jan. 30, 2018.
Zhou et al., "Comparative Analysis In Vitro of Regulatory Elements That Drive Targeted Gene Expression in Adenovirus-Associated Viral (AAV) Vectors," Molecular Therapy 23:S77-S78, Apr. 30, 2015.
Lim et al., "Functional recovery in a Friedreich's ataxia mouse model by frataxin gene transfer using an HSV-1 amplicon vector," Molecular Therapy 15(6):1072-1078, Jun. 2007.
Gomez-Sebastian et al., "Infectious Delivery and Expression of a 135kb Human FRDA Genomic DNA Locus Complements Friedreich's Ataxia Deficiency in Human Cells," Molecular Therapy 15(2):248-254, Feb. 2007.
Faraj et al., "The alteration of the C-terminal region of human frataxin distorts its structural dynamics and function," FEBS J 281:3397-3419 (2014).
Thorstad, M., "Functional Characterization and Surface Mapping of Frataxin (FXN) Interactions with the Fe—S Cluster Assembly Complex," Master's Thesis at the Texas A&M University, Aug. 2013.
Campuzano et al., "Frataxin is reduced in Friedreich ataxia patients and is associated with mitochondrial membranes," Human Molecular Genetics 6(11):1771-1780 (1997).
Carvajal et al., "The Friedreich's ataxia gene encodes a novel phosphatidylinositol-4-phosphate 5-kinase," Nature Genetics 14:157-162 (1996).
Fleming et al., "Partial Correction of Sensitivity to Oxidant Stress in Friedreich Ataxia Patient Fibroblasts by Fraxtaxin-Encoding Adeno-Associated Virus and Lentivirus Vectors," Human Gene Therapy 16:947-956 (2005).
GenBank Accession Number NM_000144.4: "*Homo sapiens* frataxin (FXN), transcript variant 1, mRNA," Last Modified Oct. 21, 2018, Accessed on Jan. 6, 2021 at <https://www.ncbi.nlm.nih.gov/nuccore/NM_000144.4>.

(Continued)

*Primary Examiner* — Marcia S Noble
(74) *Attorney, Agent, or Firm* — Medler Ferro Woodhouse & Mills PLLC

(57) ABSTRACT

The invention provides polynucleotides, vectors and viruses expressing frataxin and methods of treating Friedreich's Ataxia.

23 Claims, 33 Drawing Sheets
Specification includes a Sequence Listing.

(56) References Cited

OTHER PUBLICATIONS

Gerard et al., "An AAV9 coding for frataxin clearly improved the symptoms and prolonged the life of Friedreich ataxia mouse models," *Molecular Therapy* 1:14044 (2014).

Isaacs et al., "Prospects of gene and cell therapy for managing cardiac complications in Friedreich axtaxia," *Expert Opinion on Orphan Drugs* 3(10):1183-1196 (2015).

Mendelsohn, A., "Tunable Frataxin Replacement Therapy," National Institutes of Health Grant Number 1R43NS087730-01; Project Start May 1, 2014, Accessed on May 1, 2021 at <https://grantome.com/grant/NIH/R43-NS087730-01>.

Pandolfo, M., "Friedreich ataxia: The clinical picture," *Journal of Neurology* 256 [Suppl 1]:3-8 (2009).

Perdomini et al., "Prevention and reversal of severe mitochondrial cardiomyopathy by gene therapy in a mouse model of Friedreich's ataxia," *Nature Medicine* 20(5):542-547.

Puccio et al., "AAV Based Gene Therapy Rescues the Murine Cardiac Phenotype Associated with Friedreich's Axtaxia," *Molecular Therapy* 20 [Suppl 1]:S215 (2012).

\* cited by examiner

First Tier Expression Analysis

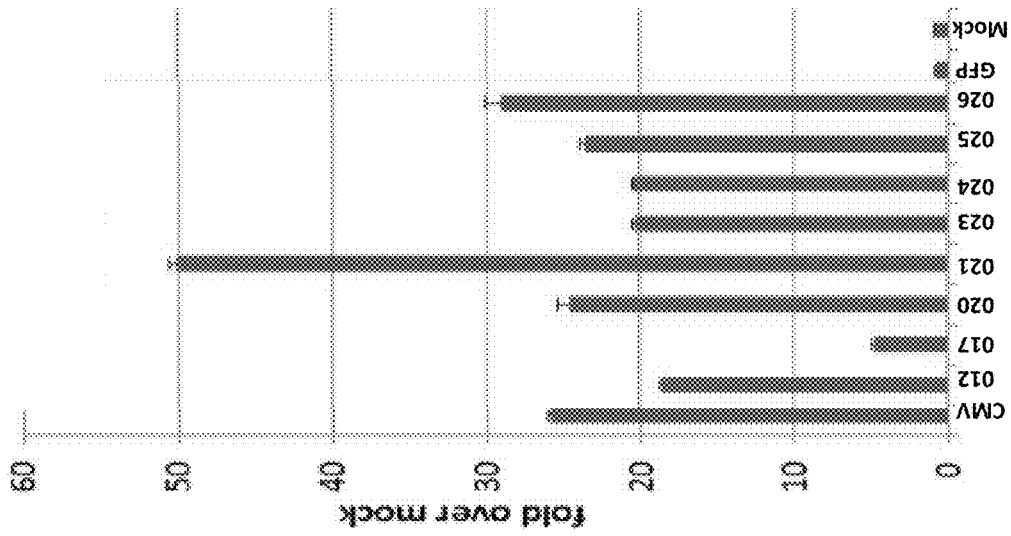
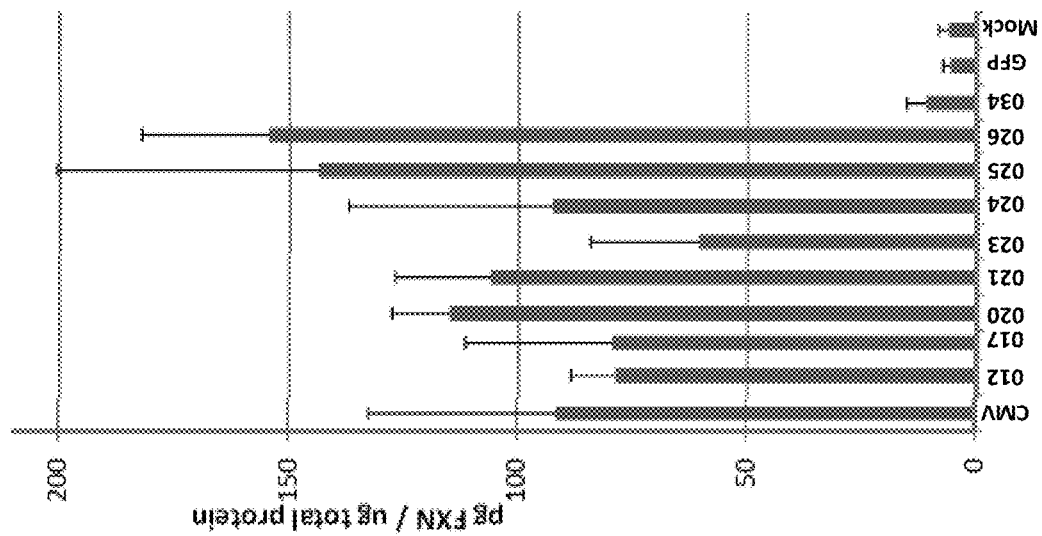
FIG. 3A
FIG. 3B
Second Tier Expression Analysis

Second Tier Expression Analysis

Human Frataxin is Transported to the Mitochondria Appropriate Intracellular Trafficking

African Green Money Fibroblasts (COS-7)

Human Frataxin is Transported to the Mitochondria
Appropriate Intracellular Trafficking Murine Fibroblasts (NC6)

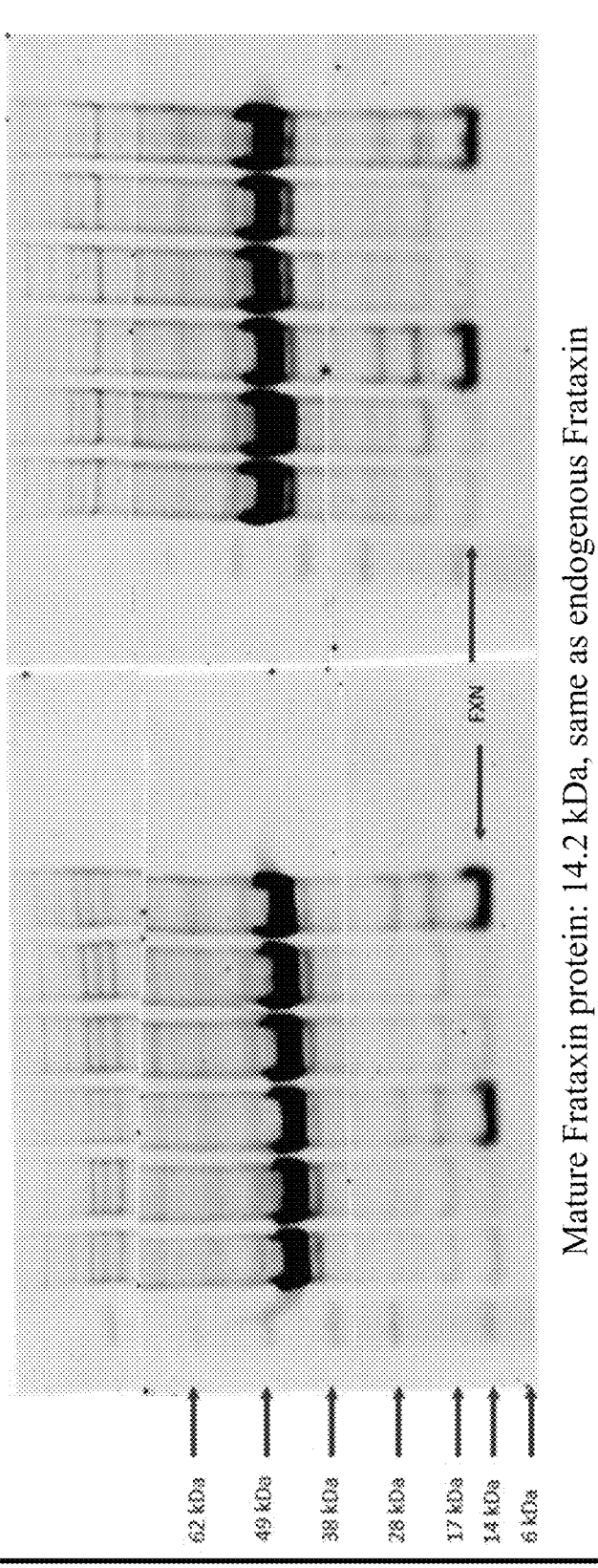

```
         10         20         30         40         50         60         70
MWTLGRRAVA GLLASPSPAQ AQTLTRVPRP AELAPLCGRR GLRTDIDATC TPRRASSNQR
GLNQIWNVKK
         80         90        100        110        120        130        140
QSVYLMNLRK SGTLGHPGSL DETTYERLAE ETLDSLAEFF EDLADKPYTF EDYDVSFGSG
VLTVKLGGDL
        150        160        170        180        190        200        210
GTYVINKOTP NKOIWLSSPS SGPKRYDWTG KNWVYSHDGV SLHELLAAEL TKALKTKLDL
SSLAYSGKDA
```

FIG. 16

```
                         AAV2 ITR
cct gca ggc agc tgc gcg ctc gct cgc tca ctg agg ccg ccc ggg caa agc ccg ggc gtc ggg cga cct ttg gtc gcc cgg cct cag tga gcg agc gag cgc gca gag agg gag tgg cca
                                       I-CeuI RE site
act cca tca cta ggg gtt cct taa cta taa cgg tcc taa ggt agc ga
 AsiSI   PacI      FseI               human UBC promoter
gcg atc gct taa tta agg ccg gcc ggc ctc cgc gcc ggg ttt ggc gct ccg cgg gcg ccc ccc tcc tca cgg cga gcg ctg cca cgt cag acg aag ggc gca gcg agc gtc ctg atc ctt ccg ccc gga cgc tca gga cag cgg ccc gct gct cat aag act cgg cct tag aac ccc agt atc agc aga agg aca ttt tag gac ggg act tgg gtg act cta ggg cac tgg ttt tct ttc cag aga gcg aac cag gcg agg aaa agt agt ccc ttc tcg gcg att ctg cgg agg gat ctc cgt ggg gcg gtg aac gcc gat gat tat ata agg acg cgc cgg gtg tgg cac agc tag ttc cgt cgc agc cgg gat ttg ggt cgc ggt tct tgt ttg tgg atc gct gtg atc gtc act tgg tga gta gcg ggc tgc tgg gct ggg tac gtg cgc tcg ggt tgc gagt gtg ttt tgt gaa gtt ttt tag gca cct ttt gaa atg taa tca ttt ggg tca ata tgt aat ttt cag tgt
                                                                        SBfI
tag act agt aaa ttg tcc gct aaa ttc tgg ccg ttt ttg gct ttt tgt tga cgc tgc
     AscI   MluI         5U2
agg ggc gcg cca cgc gtc gaa gaa ggt gag taa tct aag cat gct ctt ttt ttt ttt tgc taa tcc ctt ttg tgt gct gat gtt agg atg aca ttt aca aca aat gtt gtc tga cag gaa aaa cct tgc tgg gta cct tcg ttg ccg gac act tct tgt cct cta ctt tgg aaa
                         NheI          FXN (+ Kozak)
aaa gga att gag agc cgc tag cgc cac cat gtg gac tct cgg gcg ccg cgc agt agc cgg cct cct ggc gtc acc cag ccc agc cca ggc cca gac cct cac ccg ggt ccc gcg gcc ggc aga gtt ggc ccc act ctg cgg ccg ccg tgg cct gcg cac cga cat cga tgc gac ctg cac gcc ccg ccg cgc aag ttc gaa cca acg tgg cct caa cca gat ttg aaa tgt caa aaa gca gag tgt cta ttt gat gaa ttt gag gaa atc tgg aac ttt ggg cca ccc agg ctc tct aga tga gac cac cta tga aag act agc aga gga aac gct gga ctc ttt agc aga gtt ttt tga aga cct tgc aga caa gcc ata cac gtt tga gga cta tga tgt ctc ctt ggg agt gg tgt ctt aac tgt caa act ggg tgg aga tct agg aac cta tgt gat caa caa gca gac gcc aaa caa gca aat ctg gct atc ttc tcc atc cag tgg acc taa gcg tta tga ctg gac tgg gaa aaa ctg ggt gta ctc cca cga cgg cgt gtc cct cca tga gct gct ggc gcg aga gct cac taa agc ctt aaa aac caa act gga ctt gtc ttc ctt ggc cta ttc cgg aaa aga tgc ttg
 ClaI   SnaBI   NotI     SalI              hGH poly A
aat cga tta cgt agc ggc cgc gtc gac tga tgg gtg gca tcc ctg tga ccc ctc ccc agt
```

FIG. 19A

```
      hGH poly A (continued)
gcc tct cct ggc cct gga agt tgc cac tcc agt gcc cac cag cct tgt cct aat aaa att
aag ttg cat cat ttt gtc tga cta ggt gtc ctt cta taa tat tat ggg gtg gag ggg ggt
ggt atg gag caa ggg gca agt tgg gaa gac aac ctg tag ggc ctg cgg ggt cta ttg gga
acc aag ctg gag tgc agt ggc aca atc ttg gct cac tgc aat ctc cgc ctc ctg ggt tca
agc gat tct cct gcc tca gcc tcc cga gtt gtt ggg att cca ggc atg cat gac cag gct
cag cta att ttt gtt ttt ttg gta gag acg ggg ttt cac cat att ggc cag gct ggt ctc
caa ctc cta atc tca ggt gat cta ccc acc ttg gcc tcc caa att gct ggg att aca ggc
gtg aac cac tgc tcc ctt ccc tgt cct tct gat ttt aaa ata act ata cca gca gga gga
cgt cca gac aca gca tag gct acc tgg cca tgc cca ccg gtg gga aca ttt gag ttg ctt
                                                                         SwaI
gct tgg cac tgt cct ctc atg cgt tgg gtc cac tca gta gat gcc tgt tga att att taa
  RsrII   BsiWI        2250 bp synthetic mammalian neutral stuffer
atc ggt ccg cgt acg tta tgg cta tag aat gcc cca tct tag att gta ggt gac ttg aga
ggt cta agt cct tct ata gga tat cct tct agg tag gta taa tac tag tct agg tta aac
tag gct agg gag tca gag agc att cgc aaa gtt tac cta gtc tac aag tct ctc cca cta
tcc ttg agc cta ccc tag gct aga tcc tag gaa tca tcc cat gtc gtc att cta gct cat
agc act ctc act atc cta cta gct agg cca tct tcc tag gaa aag tat aag atc cta gtt
tga tat agc atc aat gta gct agt ggg aag gat acg gat gac ctc ata gct tgc agc ttt
ata aac ttc tcc ctc cca tac cac cta cct agg tgc tat gag gtg act tta gaa tca ccc
tct agg agg tag act atg ata gtc ctt cct tct agt atc aag ata tca tct agc tac aag
tta tcg aag gtt gac cta acc tta tag caa tat ttt gac cta cct gag agc ttt aga gcc
cta gtt tga gag tct atg tcc atc tag ggc cta cct acc tta cct act aca tga tgt agc
tct atc cta gag ccc tct cat ggt tat gag ttg cct gca agg cta gaa tct agg aag atc
ctt cca tca tat cct tgt agc tat ttt cta caa tcg aga aga ggt cct cct act tct aac
ttt tgc cat tgc ccc atc tag cta caa ggt tat gag aga gag tat aag tca tgc cat aat
acc tag gta gaa att ctc acc tat cct att tct ttc tag ctt gca gtg cta cta gca tgg
ggt gag atc ttg agt cta gcc ttt tgt cct agg gac ttt tag agc cta aga ctc tag agt
gcc ccg atc taa tat cct tct ata act tcc tac cag tct ctt ata gcc ttt gac cct att
tct acc acc tac ttc gca tgg tct ttc ttt acc tta cca taa gac tgc ctt aga cta cct
agg gag aga ctt aag gcc atg cta taa gct ata ggt cta ggc tat atc ctt tca cca tat
agc atg atc ata ggc gca aag tag aaa gga ctc tag gat aga gac tct ata gat gag ctt
```

FIG. 19B

```
gat act gac ttt gtc gtt act ttg acc cta gta gct cat act atc atg atg gtg act ctt
gag cca gta tga tct ttg tcc taa gtc cca ccc cat ctt tgc cac gct ata gat ctg ctc
taa gct ata gac cat cct tga cct acc tta gag tat agg tca aac tct aga cta gac ttt
gta gga ggg cta tag cct ttg ccc cat ctc acc tca ctc tct aat att tct atg agc ttt
tag gta aag tat ctt cta aag cta tcc tag ggt cct ttt act tca gca agt gca agg agt
caa atc tct tac ttt agg cct agc aat ctt agg tcg caa gac cct cta tag ctc tct tct
agc tca tag cat ggg ata acc ttc agt caa aag tgc tag act tgc tag aga tgc tct aga
tag ttt gac cta agg tag gtt aga aag tca ctt tcg tcc ttt tgt agt agg tca ctg aga
ctt aga atg gtc tat cct tgc tcc cta gct tag ggt ggg atc ttt tag gcc ttt gag cct
agc aag gac tct agt cta ggg tcc atc cca tct cct gca aga atc tct caa gga aag gtt
gta gaa gga atg aga gta gca atc tat agc aag gat gat ggt tgt aga atg agc atg tag
gta agg cat gag ata ctt tta cct cgt acc ttg tag gcc tat aag act ttg act tat aaa
agt ctg tcc tcc cta gcc tat atg gcc tag aaa ata gga cct tga aag aat gct ata gtg
agc tta tgg cct aca tcc tag aga atc tag gta aaa gat att atg act tag gta cta gag
tac cag caa gct aga gcc tat agc ccc atc cta ctt caa atc tta gag tat agt act tca
aag atc ata tac tct gac ttt aga cca tgg cct tag aag agg tta gag tga ggg tcc tcc
ctt gcg agg tag gag agc atc ttg agc ttt tag gag cat cct agc agc tag gtc tag aga
ggg caa gtt aga gaa gtt tga gtc atg cta gag ggc aaa gtc tca gcc tcc ttg tcc tac
                                                                          I-SceI
aag agt cat cta ggt ata gct aca tca aac tat cat aga agt ttg att acc ctg tta tcc
                  ITR
cta agg aac ccc tag tga tgg agt tgg cca ctc cct ctc tgc gcg ctc gct cgc tca ctg
agg ccg ggc gac caa agg tcg ccc gac gcc cgg gct ttg ccc ggg cgg cct cag tga gcg
agc gag cgc gca gct gcc tgc agg
```

FIG. 19C

```
0001  taactataac  ggtcctaagg  tagcgagcga  tcgcttaatt  aaggccggcc  ggcctccgcg
0061  ccgggttttg  gcgcctcccg  cgggcgcccc  cctcctcacg  gcgagcgctg  ccacgtcaga
0121  cgaagggcgc  agcgagcgtc  ctgatccttc  cgcccggacg  ctcaggacag  cggcccgctg
0181  ctcataagac  tcggccttag  aaccccagta  tcagcagaag  gacatttag   gacgggactt
0241  gggtgactct  agggcactgg  ttttctttcc  agagagcgga  acaggcgagg  aaaagtagtc
0301  ccttctcggc  gattctgcgg  agggatctcc  gtggggcggt  gaacgccgat  gattatataa
0361  ggacgcgccg  ggtgtggcac  agctagttcc  gtcgcagccg  ggatttgggt  cgcggttctt
0421  gtttgtggat  cgctgtgatc  gtcacttggt  gagtagcggg  ctgctgggct  gggtacgtgc
0481  gctcggggtt  ggcgagtgtg  ttttgtgaag  tttttttaggc acctttttgaa atgtaatcat
0541  ttgggtcaat  atgtaatttt  cagtgttaga  ctagtaaatt  gtccgctaaa  ttctggccgt
0601  ttttggcttt  tttgttagac  gcctgcaggg  gcgcgccacg  cgtcgaagaa  ggtgagtaat
0661  cttaacatgc  tcttttttt   ttttttttgct aatccctttt  gtgtgctgat  gttaggatga
0721  catttacaac  aaatgtttgt  tcctgacagg  aaaaaccttg  ctgggtacct  tcgttgccgg
0781  acacttcttg  tcctctactt  tggaaaaaag  gaattgagag  ccgctagcgc  caccatgtgg
0841  actctcgggc  gccgcgcagt  agccggcctc  ctggcgtcac  ccagcccagc  ccaggcccag
0901  accctcaccc  gggtccgcg   gccggcagag  ttggccccac  tctgcggccg  ccgtggcctg
0961  cgcaccgaca  tcgatgcgac  ctgcacgccc  cgccgcgcaa  gttcgaacca  acgtggcctc
1021  aaccagattt  ggaatgtcaa  aaagcagagt  gtctatttga  tgaatttgag  gaaatctgga
1081  actttgggcc  acccaggctc  tctagatgag  accacctatg  aaagactagc  agaggaaacg
1141  ctggactctt  tagcagagtt  ttttgaagac  cttgcagaca  agccatacac  gtttgaggac
1201  tatgatgtct  cctttgggag  tggtgtctta  actgtcaaac  tgggtgaga   tctaggaacc
1261  tatgtgatca  acaagcagac  gccaaacaag  caaatctggc  tatcttctcc  atccagtgga
1321  cctaagcgtt  atgactggac  tgggaaaaac  tgggtgtact  cccacgacgg  cgtgtccctc
1381  catgagctgc  tggccgcaga  gctcactaaa  gccttaaaaa  ccaaactgga  cttgtcttcc
1441  ttggcctatt  ccggaaaaga  tgcttgaatc  gattacgtag  cggccgcgtc  gactgatggg
1501  tggcatccct  gtgaccctc   cccagtgcct  ctcctggccc  tggaagttgc  cactccagtg
1561  cccaccagcc  ttgtcctaat  aaaattaagt  tgcatcattt  tgtctgacta  ggtgtccttc
1621  tataatatta  tggggtggag  gggggtggta  tggagcaagg  ggcaagttgg  gaagacaacc
1681  tgtagggcct  gcggggtcta  ttgggaacca  agctggagtg  cagtggcaca  atcttggctc
1741  actgcaatct  ccgcctcctg  ggttcaagcg  attctcctgc  ctcagcctcc  cgagttgttg
1801  ggattccagg  catgcatgac  caggctcagc  taattttttgt tttttttggta gagacgggt
1861  ttcaccatat  tggccaggct  ggtctccaac  tcctaatctc  aggtgatcta  cccaccttgg
1921  cctcccaaat  tgctgggatt  acaggcgtga  accactgctc  ccttccctgt  cctttctgatt
1981  ttaaaataac  tataccagca  ggaggacgtc  cagacacagc  ataggctacc  tggccatgcc
2041  caaccggtgg  gacatttgag  ttgcttgctt  ggcactgtcc  tctcatgcgt  tgggtccact
2101  cagtagatgc  ctgttgaatt  atttaaatcg  gtccgcgtac  gttatggcta  tagaatgccc
2161  catcttagat  tgtaggtgac  ttgagaggtc  taagtcctc   tataggatat  ccttctaggt
2221  aggtataata  ctagtctagg  ttaaactagg  ctagggagtc  agagagcatt  cgcaaagttt
2281  acctagtcta  caagtctctc  ccactatcct  tgagcctacc  ctaggctaga  tcctaggaat
2341  catccatgt   cgtcattcta  gctcatagca  ctctcactat  cctactagct  aggccatctt
2401  cctaggaaaa  gtataagatc  ctagtttgat  atagcatcaa  tgtagctagt  gggaaggata
2461  cggatgacct  catagcttgc  agctttataa  acttctccct  cccataccac  ctacctaggt
2521  gctatgaggt  gactttagaa  tcacctcta   ggaggtagac  tatgatagtc  cttccttcta
2581  gtatcaagat  atcatctagc  tacaagttat  cgaaggttga  cctaacctta  tagcaatatt
2641  ttgacctacc  tgagagcttt  agagccctag  tttgagagtc  tatgtccatc  tagggcctac
2701  ctaccttacc  tactacatga  tgtagctcta  tcctagagcc  ctctcatggt  tatgagttgc
2761  ctgcaaggct  agaatctagg  aagatccttc  catcatatcc  ttgtagctat  tttctacaat
2821  cgagaagagg  tcctcctact  tctaactttt  gccattgccc  catctagcta  caaggttatg
2881  agagagta    taagtcatgc  cataatacct  aggtagaaat  tctcacctat  cctatttctt
2941  tctagcttgc  agtgctacta  gcatgggtg   agatcttgag  tctagccttt  tgtcctaggg
3001  acttttagag  cctaagactc  tagagtgccc  cgatctaata  tccttctata  acttcctacc
3061  agtctcttat  agcctttgac  cctatttcta  ccacctactt  cgcatggtct  ttctttacct
3121  taccataaga  ctgccttaga  ctactagggg  agagactaa   ggcactgcta  taagctatag
3181  gtctaggcta  tatccttca   ccatataggca tgatcatagg cgcaaagtag  aaaggactct
3241  aggatagaga  ctctatagat  gagcttgata  ctgactttgt  cgttactttg  accctagtag
3301  ctcatactat  catgatggtg  actcttgagc  cagtatgatc  tttgtcctaa  gtcccacccc
3361  atctttgcca  cgctatagat  ctgctctaag  ctatagacca  tccttgacct  accttagagt
3421  ataggtcaaa  ctctagacta  gactttgtag  gagggctata  gcctttgccc  catctcacct
```

FIG. 20A

```
3481  cactctctaa  tatttctatg  agcttttagg  taaagtatct  tctaaagcta  tcctagggtc
3541  cttttacttc  agcaagtgca  aggagtcaaa  tctcttactt  taggcctagc  aatcttaggt
3601  cgcaagaccc  tctatagctc  tcttctagct  catagcatgg  gataaccttc  agtcaaaagt
3661  gctagacttg  ctagagatgc  tctagatagt  ttgacctaag  gtaggttaga  aagtcacttt
3721  cgtccttttg  tagtaggtca  ctgagactta  gaatggtcta  tccttgctcc  ctagcttagg
3781  gtgggatctt  ttaggccttt  gagcctagca  aggactctag  tctagggtcc  atcccatctc
3841  ctgcaagaat  ctctcaagga  aaggttgtag  aaggaatgag  agtagcaatc  tatagcaagg
3901  atgatggttg  tagaatgagc  atgtaggtaa  ggcatgagat  acttttacct  cgtaccttgt
3961  aggcctataa  gactttgact  tataaaagtc  tgtcctccct  agcctatatg  gcctagaaaa
4021  taggaccttg  aaagaatgct  atagtgagct  tatggcctac  atcctagaga  atctaggtaa
4081  aagatattat  gacttaggta  ctagagtacc  agcaagctag  agcctatagc  cccatcctac
4141  ttcaaatctt  agagtatagt  acttcaaaga  tcatatactc  tgactttaga  ccatggcctt
4201  agaagaggtt  agagtgaggg  tcctcccttg  cgaggtagga  gagcatcttg  agcttttagg
4261  agcatcctag  cagctaggtc  tagagagggc  aagttagaga  agtttgagtc  atgctagagg
4321  gcaaagtctc  agcctccttg  tcctacaaga  gtcatctagg  tatagctaca  tcaaactatc
4381  atagaagttt  gattaccctg  ttatccctaa  ggaacccta  gtgatggagt  tggccactcc
4441  ctctctgcgc  gctcgctcgc  tcactgaggc  cgggcgacca  aaggtcgccc  gacgccggg
4501  ctttgcccgg  gcggcctcag  tgagcgagcg  agcgcgcagc  tgcctgcagg  atctatgtcg
4561  ggtgcggaga  aagaggtaat  gaaatggcaa  gtacttccgg  aactataaat  tgcgttgcgc
4621  tcactgcccg  ctttccagtc  gggaaacctg  tcgtgccagc  tgcataaatg  aatcggccaa
4681  cgcgcgggga  gaggcggttt  gcgtattggg  cgcgcttccg  cttcctcgct  cactgactcg
4741  ctgcgctcgg  tcgttcgctg  gcggcgagcg  gtatcagctc  actcaaaggc  ggtaatacgg
4801  ttatccacag  aatcagggga  taacgcagga  aagaacatgt  gagcaaaagg  ccagcaaaag
4861  gccaggaacc  gtaaaaaggc  cgcgttgctg  gcgtttttcc  ataggctccg  cccccctgac
4921  gagcatcaca  aaaatcgacg  ctcaagtcag  aggtggcgaa  acccgacagg  actataaaga
4981  taccaggcgt  ttccccctgg  aagctccctc  gtgcgctctc  ctgttccgac  cctgccgctt
5041  accggatacc  tgtccgcctt  tctcccttcg  ggaagcgtgg  cgctttctca  tagctcacgc
5101  tgtaggtatc  tcagttcggt  gtaggtcgtt  cgctccaagc  tgggctgtgt  gcacgaaccc
5161  cccgttcagc  ccgaccgctg  cgccttatcc  ggtaactatc  gtcttgagtc  caacccggta
5221  agacacgact  tatcgccact  ggcagcagcc  actggtaaca  ggattagcag  agcgaggtat
5281  gtaggcggtg  ctacagagtt  cttgaagtgg  tggcctaact  acggctacac  tagaagaaca
5341  gtatttggta  tctgcgctct  gctgaagcca  gttaccttcg  gaaaaagagt  tggtagctct
5401  tgatccggca  aacaaaccac  cgctggtagc  ggtggttttt  ttgtttgcaa  gcagcagatt
5461  acgcgcagaa  aaaaggatc  tcaagaagat  cctttgatct  tttctacggg  gtctgacgct
5521  cagtggaacg  aaaactcacg  ttaagggatt  ttggtcatga  gattatcaaa  aaggatcttc
5581  acctagatcc  ttttaaatta  aaaatgaagt  tttaaatcaa  tctaaagtat  atatgagtaa
5641  acttggtctg  acatgcgcag  ttaccaatgc  ttaatcagtg  aggcacctat  ctcagcgatc
5701  tgtctatttc  gttcatccat  agttgcctga  ctccccgtcg  tgtagataac  tacgatacgg
5761  gagggcttac  catctggccc  cagtgctgca  atgataccgc  gagacccacg  ctcaccggct
5821  ccagatttat  cagcaataaa  ccagccagcc  ggaagcgccg  agcgcagaag  tggtcctgca
5881  actttatccg  cctccatcca  gtctattaac  tgttgccggg  aagctagagt  aagtagttcg
5941  ccagttaata  gtttgcggag  cgttgttgcc  attgctacag  gcatcgtggt  gtcacgctcg
6001  tcgtttggta  tggcttcatt  cagctccggt  tcccaacgat  caaggcgagt  tacatgatcc
6061  cccatgttgt  gcaaaaaagc  ggttagctcc  ttcggtcctc  cgatcggtgt  tgtcagaagtaag
6121  ttggccgcag  tgttatcact  catggttatg  gcagcactgc  ataattctct  tactgtcatg
6181  ccatccgtaa  gatgcttttc  tgtgactggt  gagtattcaa  ccaagtcatt  ctgagaatag
6241  tgtatgcggc  gaccgagttg  ctcttgcccg  gcgtcaatac  gggataatac  cgcgccacat
6301  agcagaactt  taaaagtgct  catcattggg  aagcgttctt  cggggcgaaa  actctcaagg
6361  atcttaccgc  tgttgagatc  cagttcgatg  taacccacac  gagcacccaa  ctgatcttca
6421  gcatctttta  ctttcaccag  cgtttctggg  tgagcaaaaa  caggaaggca  aaatgccgca
6481  aaaagggaa  taagggcgac  acggaaatgt  tgaatactca  tactcttcct  ttttcaatat
6541  tattgaagca  tttatcaggg  ttattgtctc  atgagcggat  acatatttga  atgtatttag
6601  aaaataaaca  aataggggt   tccgcgcaca  tttccccgaa  aagtgccacc  tgaggtctaa
6661  gaaaccatta  ttatcatgac  attaacctat  aaaaatag gc  gtatcacgag  gccctttctt
6721  ctcgcgcgtt  tcggtgatga  cggtgaaaac  ctctgacaca  tgcagctccc  ggatacggtc
6781  acagcttgtc  tgtaagcgga  tgccgggagc  agacaagccc  gtcagggcgc  gtcagcgggt
6841  gttggcgggt  gtcggggctg  gcttaagctg  agctaactat  gactctctta  aggtagccaa
6901  atcctgcagg  cagctgcgcg  ctcgctcgct  cactgaggcc  gcccgggcaa  agcccgggcg
6961  tcgggcgacc  tttggtcgcc  cggcctcagt  gagcgagcga  gcgcgcagag  agggagtggc
7021  caactccatc  actagggtt   cct
```

FIG. 20B

FRATAXIN EXPRESSION CONSTRUCTS

This application incorporates by reference a "Sequence Listing" (identified below) which is submitted concurrently herewith in text file format via the U.S. Patent Office's Electronic Filing System (EFS). The text file copy of the Sequence Listing submitted herewith is labeled "INX00317PT_ST25", is a file of 40.298 bytes in size, and was created on Oct. 4, 2017. This Sequence Listing is incorporated by reference in its entirety herein.

BACKGROUND OF THE INVENTION

Friedreich's Ataxia (FA) is the most common form of inheritable ataxia and affects around 1 in 50,000 people in the United States. Friedreich's ataxia is caused by a mutation in the gene coding for frataxin gene (FXN) which is present on chromosome 9. The underlying molecular pathology of FA is due to the presence of a trinucleotide GAA repeat expansion (70-1700) in the first intron of the FXN (Campuzano et al. (1996) *Hum. Mol. Genet.* 6:1771-1780). The effect of this gene mutation is production of inadequate quantities of the mitochondrial protein frataxin, which appears to play an important role in iron homeostasis (Pandolfo (2008) *Archives of Neurology* 65:1296-1303; Campuzano et al. (1996) *Hum. Mol. Genet.* 6:1771-1780). Reduced levels of frataxin protein are associated with mitochondrial dysfunction, and lead to cell toxicity and cell death (Pandolfo (2009) *J. Neurol.* 256 Suppl. 1:3-8). Heterozygote carriers of the defective gene express approximately 50% of normal frataxin protein levels and are asymptomatic; homozygous patients express 5-25% of normal frataxin levels and are symptomatic. Therefore, it is possible that modest increases in frataxin protein levels in cells in the CNS of FA patients could result in significant neurological improvements. Moreover, molecules that increase endogenous FXN levels or FXN protein replacement methods have shown promise in clinical and pre-clinical studies. As such, protein replacement via gene therapy is a compelling alternative option for therapeutic development. There is an urgent need in the art for a treatment and prevention of Friedreich's ataxia.

BRIEF SUMMARY OF THE INVENTION

The invention provides a polynucleotide comprising a nucleic acid molecule encoding human frataxin operably linked to control elements that direct the transcription and translation thereof. In some embodiments of the invention, the nucleic acid encodes a frataxin protein with amino acid sequence that is at least 80%, 85%, 90%, 95%, 98%, or 99% identical to SEQ ID NO:1. In some embodiments of the invention, the nucleic acid encodes a frataxin protein with amino acid sequence of SEQ ID NO: 1. In some embodiments, the control elements are selected from the group consisting of a promoter, a 5' regulatory element, a 3' regulatory element and combinations thereof.

In some embodiments, the promoter is selected from the group consisting of a CMV promoter, a UBC promoter an EF1α a promoter, a PGK1 promoter and a minimal frataxin promoter. In some embodiments, the 5' regulatory element is selected from the group consisting of a GAPDH sequence, a FTH1-5'UTR, a RPL6-5' Splice sequence, and a 5U2 sequence. In some embodiments, the 3' regulatory element is selected from the group consisting of an SV40 early sequence, an SV40 late sequence, a synthetic 3' regulatory element, and a human growth hormone polyadenylation sequence.

In a particular embodiment of the invention, the nucleic acid encodes a protein with the amino acid sequence of SEQ ID NO: 1, and the control elements comprise a UBC promoter (e.g., SEQ ID NO:3), a 5U2 sequence (e.g., SEQ ID NO:4) and a human growth hormone polyadenylation sequence (e.g., SEQ ID NO:5).

In another particular embodiment of the invention, the nucleic acid encodes a protein with the amino acid sequence of SEQ ID NO: 1, and the control elements comprise a UBC promoter (e.g., SEQ ID NO:3), a 5U2 sequence (e.g., SEQ ID NO:4) and a synthetic 3' regulatory element sequence (SEQ ID NO:7).

The invention also provides a viral vector comprising the polynucleotide of the invention. In some embodiments, the viral vector is an adeno-associated viral vector. In a specific embodiment, the viral vector is AAV5.

The invention also provides a recombinant virion which comprises a viral vector, and wherein the viral vector comprises a nucleic acid molecule encoding human frataxin operably linked to control elements that direct the transcription and translation thereof. In some embodiments, the virion contains an adeno-associated viral vector. In certain specific embodiments, the adeno-associated viral vector is AAV5. In some embodiments, the virion comprises a nucleic acid molecule encoding a protein with the amino acid sequence of SEQ ID NO:1.

In some embodiments, the control elements are selected from the group consisting of a promoter, a 5' regulatory element, a 3' regulatory element and combinations thereof. In some embodiments, the promoter is selected from the group consisting of a CMV promoter (e.g., SEQ ID NO:13), a UBC promoter (e.g., SEQ ID NO:3) an EF1α promoter (e.g., SEQ ID NO:18), a PGK1 promoter (e.g., SEQ ID NO: 17) and a minimal frataxin promoter. In some embodiments, the 5' regulatory element is selected from the group consisting of a GAPDH (e.g., SEQ ID NO:15) sequence, a FTH1-5'UTR (e.g., SEQ ID NO:14), a RPL6-5' Splice sequence (e.g., SEQ ID NO:16), and a 5U2 sequence (SEQ ID NO:4). In some embodiments, the 3' regulatory element is selected from the group consisting of an SV40 early sequence (e.g., SEQ ID NO:8), an SV40 late sequence (e.g., SEQ ID NO:9), a synthetic 3' regulatory element sequence (SEQ ID NO:7), and a human growth hormone polyadenylation sequence (e.g., SEQ ID NO:5). In certain specific embodiments, the nucleic acid encodes a protein with the amino acid sequence of SEQ ID NO:1, the promoter is a UBC promoter (SEQ ID NO:3), and the regulatory elements are a 5U2 sequence (SEQ ID NO:4) and a human growth hormone polyadenylation sequence (SEQ ID NO:5). In other specific embodiments, the nucleic acid encodes a protein with the amino acid sequence of SEQ ID NO: 1, the promoter is a UBC promoter (SEQ ID NO:3), and the regulatory elements are a 5U2 sequence (SEQ ID NO:4) and a synthetic 3' regulatory element sequence (SEQ ID NO:7).

The invention also provides a composition comprising (a) a viral vector, wherein the viral vector comprises a nucleic acid molecule encoding human frataxin operably linked to control elements that direct the transcription and translation thereof; and (b) a pharmaceutically acceptable excipient.

In some embodiments, the vector is an adeno-associated viral vector. In certain specific embodiments, the adeno-associated viral vector is AAV5.

In some embodiments, the nucleic acid encodes a frataxin protein with an amino acid sequence that is at least 80%, 85%, 90%, 95%, 98%, or 99% identical to SEQ ID NO: 1.

In some embodiments, the control elements are selected from the group consisting of a promoter, a 5' regulatory element, a 3' regulatory element and combinations thereof. In some embodiments, the promoter is selected from the group consisting of a CMV promoter (e.g., SEQ ID NO:13), a UBC promoter (e.g., SEQ ID NO:3) an EF1α promoter (e.g., SEQ ID NO:18), a PGK1 promoter (e.g., SEQ ID NO:17) and a minimal frataxin promoter. In some embodiments, the 5' regulatory element is selected from the group consisting of a GAPDH sequence (e.g., SEQ ID NO:15), a FTH1-5'UTR (e.g., SEQ ID NO:14), a RPL6-5' Splice sequence (e.g., SEQ ID NO:16), and a 5U2 sequence (SEQ ID NO:4). In some embodiments, the 3' regulatory element is selected from the group consisting of an SV40 early sequence (e.g., SEQ ID NO:8), an SV40 late sequence (e.g., SEQ ID NO:9), a synthetic 3' regulatory element sequence (SEQ ID NO:7), and a human growth hormone polyadenylation sequence (e.g., SEQ ID NO:5). In certain specific embodiments, the nucleic acid encodes a protein with the amino acid sequence of SEQ ID NO: 1, the promoter is a UBC promoter (SEQ ID NO:3), and the regulatory elements are a 5U2 sequence (SEQ ID NO:4) and a human growth hormone polyadenylation sequence (SEQ ID NO:5). In certain other specific embodiments, the nucleic acid encodes a protein with the amino acid sequence of SEQ ID NO:1, the promoter is a UBC promoter (SEQ ID NO:3), and the regulatory elements are a 5U2 sequence (SEQ ID NO:4) and a synthetic 3' regulatory element sequence (SEQ ID NO:7).

The invention also provides a composition comprising (a) a recombinant virion and (b) a pharmaceutically acceptable excipient, wherein the recombinant virion comprises a viral vector, and wherein the viral vector comprises a nucleic acid molecule encoding a human frataxin protein with amino acid sequence that is at least 80%, 85%, 90%, 95%, 98%, or 99% identical to SEQ ID NO: 1, operably linked to control elements that direct the transcription and translation thereof. In some embodiments, the virion contains an adeno-associated viral vector. In certain specific embodiments, the adeno-associated viral vector is AAV5. In some embodiments, the virion comprises a nucleic acid molecule encoding a protein with the amino acid sequence of SEQ ID NO: 1.

In some embodiments, the control elements are selected from the group consisting of a promoter, a 5' regulatory element, a 3' regulatory element and combinations thereof. In some embodiments, the promoter is selected from the group consisting of a CMV promoter, a UBC promoter an EF1α promoter, a PGK1 promoter and a minimal frataxin promoter. In some embodiments, the 5' regulatory element is selected from the group consisting of a GAPDH sequence (e.g., SEQ ID NO:15), a FTH1-5'UTR (e.g., SEQ ID NO:14), a RPL6-5' Splice sequence (e.g., SEQ ID NO:16), and a 5U2 sequence (SEQ ID NO:4). In some embodiments, the 3' regulatory element is selected from the group consisting of an SV40 early sequence (SEQ ID NO:8), an SV40 late sequence (SEQ ID NO:9), a synthetic 3' regulatory element sequence (SEQ ID NO:7), and a human growth hormone polyadenylation sequence (SEQ ID NO:5). In certain specific embodiments, the nucleic acid encodes a protein with the amino acid sequence of SEQ ID NO: 1, the promoter is a UBC promoter (SEQ ID NO:3), and the regulatory elements are a 5U2 sequence (SEQ ID NO:4) and a human growth hormone polyadenylation sequence (SEQ ID NO:5). In other specific embodiments, the nucleic acid encodes a protein with the amino acid sequence of SEQ ID NO: 1, the promoter is a UBC promoter (SEQ ID NO:3), and the regulatory elements are a 5U2 sequence (SEQ ID NO:4) and a synthetic 3' regulatory element sequence (SEQ ID NO:7).

In some embodiments, the pharmaceutically acceptable excipient is 1×PBS, (e.g., 0.154M NaCl, 0.056M $Na_2HPO_4$, and 0.0106 M $KH_2PO_4$) or DPBS (e.g., 0.337M NaCl, 0.027 M KCl, 0.015M $Na_2HPO_4$, and 0.0015M $KH_2PO_4$).

In some embodiments, the viral vector is present at a concentration of $2.5 \times 10^{11}$ vg/mL, $7.5 \times 10^{11}$ vg/mL, or $2.5 \times 10^{12}$ vg/mL.

In some embodiments, the pH of the composition is 6.5 to 7.5; 7.0 to 7.5; 6.8 to 7.2. In some embodiments, the pH of the composition is 7.0 or 7.4.

The composition may further comprise empty capsids at a percentage of at most 95% cp/cp, preferably 50% cp/cp or less.

The invention also provides a method of treating Friedrich's Ataxia, comprising providing a pharmaceutical formulation comprising a viral vector (e.g., preferably an AAV vector such as, but not limited to an AAV5 vector), wherein the vector comprises a polynucleotide encoding a human frataxin protein and a pharmaceutically-acceptable excipient to at least one target site in the CNS of the subject in a dose of at least about $1 \times 10^9$ vg, $1 \times 10^{10}$ vg, $1 \times 10^{11}$ vg, or $1 \times 10^{12}$ vg, or more. In some embodiments, the dose is at least about $1 \times 10^{13}$ vg, $5 \times 10^{13}$ vg, $1.5 \times 10^{14}$ vg, or $5 \times 10^{14}$ vg.

In some embodiments, the target site is the CSF space; the subarachnoid space, (e.g., the cisterna magna); the brain, (e.g., the cerebroventricular space, the cerebellum, the cerebrum, the hippocampus, the interior cortex, the dorsal root ganglion, or caudate nucleus); or the spine (e.g., the lumbar spine, thoracic spine, cervical spine). In some embodiments, the active ingredient (e.g., vectors expressing frataxin, virions, viruses, rAAVs, etc.) is delivered in two injections: one in the right cerebellum and one in the left cerebellum. In some embodiments, these are two equal injections. In some embodiments, the active ingredient (e.g., vectors expressing frataxin, virions, viruses, rAAVs, etc.) are administered by injecting the cerebellum and also providing it systemically.

In embodiments of the methods, the pharmaceutical formulation may be administered intraparenchymally, intrathecally, intracerebroventricularly, systemically or a combination of these. In some embodiments, the pharmaceutical formulation is administered by intrathecally in equal portions to the cisterna magna and the lumbar spine.

In some embodiments of the method, the dose is an amount of at least $3.7 \times 10^{10}$ vg/g, $1.11 \times 10^{11}$ vg/g, or $3.7 \times 10^{11}$ vg/g on a brain weight basis. In some embodiments, the pharmaceutical formulation comprises a vector concentration of at least $2 \times 10^{12}$ vg/mL, $7 \times 10^{12}$ vg/mL, or $2 \times 10^{13}$ vg/mL.

In some embodiments of the method, the pharmaceutical formulation is administered as a single bolus injection of 0.1 mL to 5 mL (e.g., 3 mL or 2 mL). In other embodiments, the pharmaceutical formulation is delivered as an infusion at a rate of 0.001 mL/min to 1 mL/min, (e.g., 0.01 mL/min).

The invention also provides a method of treating Friedreich's Ataxia in a subject in need thereof. In some embodiments, the method comprises administering to a subject a therapeutically effective amount of a pharmaceutical composition of a virus of the invention comprising a virion to express frataxin, in a pharmaceutical carrier. The recombinant virions transduce the cells in the subject, and the nucleic acid molecule is expressed by the transduced cells at a level sufficient to ameliorate at least one symptom of Friedreich's Ataxia in the subject.

The symptoms of Friedreich's Ataxia may be one or more selected from the group consisting of loss of coordination in the arms and/or legs; fatigue, vision impairment, hearing loss, slurred speech, aggressive scoliosis, diabetes mellitus, hypertrophic cardiomyopathy and cardiac arrhythmia.

In some embodiments, frataxin is expressed in the mitochondria. In some embodiments, frataxin is expressed in the cerebellum. In some embodiments, frataxin is expressed in the hippocampus. In some embodiments, frataxin is expressed in the anterior cortex. In some embodiments, frataxin is expressed in the dorsal root ganglion.

In some embodiments of the method of the invention, frataxin is expressed in said subject at a level of greater than 25% of normal levels of frataxin. In other embodiments, frataxin is expressed in said subject at a level of greater than 30% of normal levels of frataxin. In still other embodiments, frataxin is expressed in said subject at a level of greater than 40% of normal levels of frataxin. In still other embodiments, frataxin is expressed in said subject at a level of greater than 50% of normal levels of frataxin.

In certain embodiments, a gene switch which inducibly regulates (in a dose-dependent manner) expression of frataxin is incorporated into the polynucleotide to express frataxin. The gene switch may be, for example, a RHEO-SWITCH THERAPEUTIC SYSTEM® (RTS®) gene switch.

BRIEF DESCRIPTION OF THE DRAWINGS

FIG. 1A shows pg yield of FXN per μg of total protein. FIG. 1B shows fold-expression levels over mock-transfected cells. See Table 1 for construct composition.

FIG. 2A shows pg yield of FXN per μg of total protein. FIG. 2B shows fold-expression levels over mock-transfected cells. See Table 1 for construct composition.

FIGS. 3A-3B show the Tier 2 results for selected constructs employing the UBC promoter in undifferentiated SY5Y, along with the Green Fluorescent Protein (GFP), CMV and Mock controls. FIG. 3A shows pg yield of FXN per μg of total protein. FIG. 3B shows fold-expression levels over mock-transfected cells. See Table 1 for construct composition.

FIG. 4A shows pg yield of FXN per μg of total protein. FIG. 4B shows fold-expression levels over mock-transfected cells. See Table 1 for construct composition.

FIG. 5A shows pg yield of FXN per μg of total protein. FIG. 5B shows fold-expression levels over mock-transfected cells. See Table 1 for construct composition.

FIG. 6A shows pg yield of FXN per μg of total protein. FIG. 6B shows fold-expression levels over mock-transfected cells. See Table 1 for construct composition.

(FIG. 7A) nuclei stained with DAPI, (FIG. 7B) mitochondria stained with MitoTracker, (FIG. 7C) expressed human frataxin stained with anti-human frataxin (Abcam #ab11038), and (FIG. 7D) co-localization of human frataxin with nuclei and mitochondria.

(FIG. 8A) nuclei stained with DAPI, (FIG. 8B) mitochondria stained with MitoTracker, (FIG. 8C) expressed human frataxin stained with anti-human frataxin (Abcam #ab11038), and (FIG. 8D) co-localization of human frataxin with nuclei and mitochondria.

FIGS. 9A-9B show a western blot of FA (3816) Day 21 neurons were transduced with AAV5-human frataxin (026) at 500,000 genome copies/cell at days 5 and 7 post transduction (FIG. 9A) and at days 10 and 14 post transduction (FIG. 9B). Human frataxin was detected with an anti-human frataxin antibody (Abcam #ab11038) using standard Western blot techniques. Molecular weight markers were loaded to confirm the size of the mature frataxin protein (14.2 kDa). FA+: transduced cells; FA: non-transduced cells; Ctrl: control cells.

FIG. 16 shows a Normal Human Frataxin Precursor Deduced Amino Acid Sequence SEQ ID NO: 1). The underlined sequence is a peptide necessary for transportation of the frataxin protein precursor to the mitochondria. The italicized peptide must be removed to activate the protein. The fully processed, canonical frataxin protein (in bold) has 130 amino acids. The sequence is from the UniProt database: Identifier #: Q16595-1. The UniProt consortium comprises the European Bioinformatics Institute (EBI), the Swiss Institute of Bioinformatics (SIB), and the Protein Information Resource (PIR).

FIGS. 19A-19C show a Nucleotide sequence of an AAV5-hFXN-vector: gene insert: ITR to ITR-Annotated (SEQ ID NO:19).

FIGS. 20A-20B show a Nucleotide sequence of a pAAV5-hFXN plasmid (SEQ ID NO:20).

DETAILED DESCRIPTION OF THE INVENTION

Figure 1A:
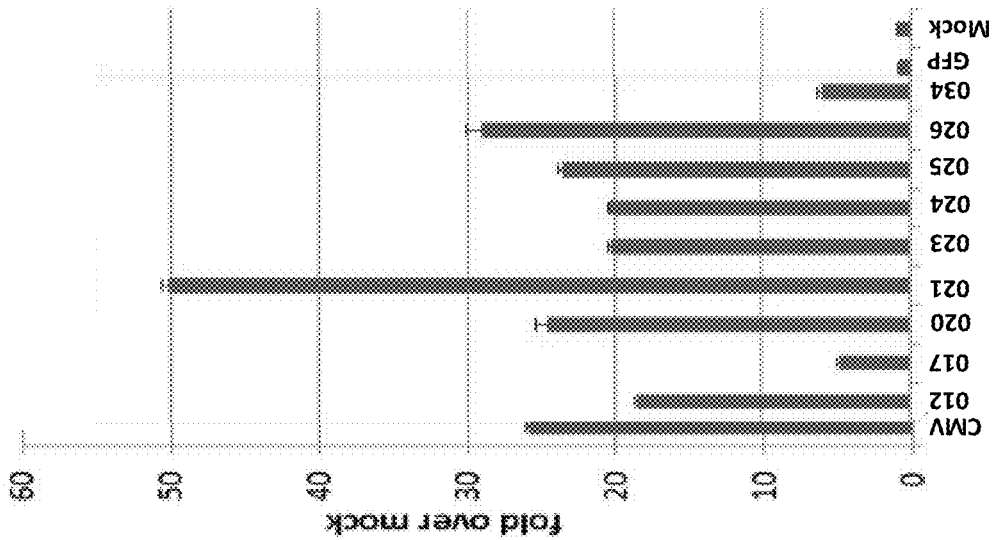
FIGS. 1A-1B show the Tier 1 results for selected constructs employing the UBC promoter in undifferentiated SY5Y, along with the Green Fluorescent Protein (GFP), CMV and Mock controls.

The present invention relates to the expression of human frataxin in cells and the treatment of Friedreich's Ataxia in patients in need thereof.

For the methods described herein, various protocols that could be used are disclosed in reference manuals such as: Current Protocols in Molecular Biology (eds. Ausubel et al., Wiley, 2004 edition.) and MOLECULAR CLONING: A LABORATORY MANUAL (Sambrook and Russell (Cold Spring Harbor Laboratory Press, 2001, third edition). Immunoreagent-containing methods such as western blots, ELISAs, and immunoprecipitations are performed as described in: USING ANTIBODIES: A LABORATORY MANUAL (Harlow and Lane Cold Spring Harbor Laboratory Press, 1999). Each of these references is incorporated herein in its entirety.

When the terms "one," "a," or "an" are used in this disclosure, they mean "at least one" or "one or more," unless otherwise indicated.

The term "AAV virus" shall mean a complete virus particle, for example a wild-type (wt) AAV virus particle. An AAV virus has an AAV capsid protein coat encasing a linear, single-stranded AAV nucleic acid genome. An AAV virus is replication-incompetent (i.e., replication-defective or helper-dependent virus). An AAV virus is optionally derived from any adeno-associated virus serotype, including without limitation, AAV-1, AAV-2, AAV-3, AAV-4, AAV-5, or AAVX7. AAV viruses can have one or more of the AAV wild-type genes deleted in whole or part, preferably the rep and/or cap genes, but retain functional flanking ITR sequences. Examples of AAV viruses include, but are not limited to, AAV viruses that are available from the American Type Culture Collection ("ATCC") under Accession Numbers 53222, 53223, 53224, 53225 and 53226. For a description of AAV viruses and their uses see, e.g., Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich et al. (1993) *Human Gene Therapy* 4:461-476.

As used herein, a "virion" is a polynucleotide comprising a viral nucleic acid backbone with a gene of interest to be expressed (e.g., frataxin) and at least on regulatory element to control expression of the gene of interest.

The term "recombinant AAV," a "rAAV," a "recombinant AAV vector," or a "rAAV vector" shall mean an infectious but replication-defective virus composed of an AAV protein shell (i.e., a capsid) encapsulating a viral vector with a gene insert different from the wild-type AAV DNA.

The term "inverted terminal repeat" or "ITR" shall mean a symmetrical nucleic acid sequence at either end of the genetic material of a virus. Without being bound by theory, literature reports show that ITRs aid the efficient multiplication of the AAV genome. Literature also reports ITRs ability to form a hairpin, which contributes to self-priming that allows primase-independent synthesis of a second nucleic acid strand. ITRs were also shown to aid both integration of AAV DNA into a host cell genome. ITRs need not be the wild-type nucleotide sequences, and may be altered, for example, by the insertion, deletion or substitution of nucleotides, so long as the sequences provide for functional rescue, replication and packaging. Optional nucleotide sequences of AAV ITR regions are known. See, e.g., Kotin, R. M. (1994) "Human Gene Therapy" 5:793-801; Berns, K. I. "Parvoviridae and their Replication" in *Fundamental Virology*, 2nd Edition, (B. N. Fields and D. M. Knipe, eds.)

The term "gene insert" shall mean a nucleic acid molecule, including a portion that encodes a polypeptide.

The term "gene therapy" shall mean a treatment of a subject comprising the introduction, to a subject, of a normal copy of one or more defective or missing genes.

The term "FXN gene therapy" or "frataxin gene therapy" shall mean a treatment of a subject comprising the introduction of a normal copy of an FYXNgene to a subject that has a defective FXN gene, is missing an FXN gene, has insufficient expression of an FXN Gene, or produces inadequate quantities of frataxin.

The term "subject," "individual," or "patient" shall be used interchangeably and shall mean a mammal, preferably a human in need of therapy. A subject may be any age. A subject may be an adult. A subject may be an adult aged about 18 years to about 60 years. A subject may be a child. A subject may be a minor child aged about 17 years or less. A subject may be a minor child aged about 10 years or less. A subject may be a minor child aged about 3 years or less.

The term "capsid" shall mean a protein coat or shell of a virus. A capsid optionally comprises one or more oligomeric structural subunits comprising proteins, optionally referred to as protomers. A capsid may optionally be surrounded by a lipid bilayer and glycoprotein envelope. In one embodiment, a capsid is an adeno-associated virus (AAV) capsid. In one embodiment, the capsid is a recombinant adeno-associated virus (rAAV) serotype-5 capsid.

The term "empty capsid" shall mean a virus protein coat that does not contain a vector genome. An empty capsid can be a virus-like particle in that it reacts with one or more antibodies that react with intact (e.g., vector genome carrying) virus (e.g. adeno-associated virus, AAV). In a non-limiting example, an empty AAV5 capsid retains the ability to react with one or more antibodies that bind to an AAV, such as an AAV5 or another AAV serotype. For example, an empty AAV2 capsid retains the ability to react with one or more antibodies that bind to AAV8.

Empty capsids may sometimes be naturally found in AAV vector preparations. Such preparations can be used in accordance with the invention. Optionally, such preparations may be manipulated to increase or decrease the number of empty capsids. For example, the amount of empty capsid can be adjusted to an amount that would be expected to reduce the inhibitory effect of antibodies. Empty capsids can also be produced independently of vector preparations, and optionally (i) added to vector preparations, or (ii) administered separately to a subject. See F. Mingozzi et al., U.S. Patent Application Publication No. 2014/0336245 "Virus vectors for highly efficient transgene delivery."

The term "modified capsid" shall mean a content-modified capsid, or a capsid modified so that the capsid is unable to enter a cell.

The term "content-modified capsid" shall mean a capsid carrying a gene insert that is modified. Examples of gene inserts that are modified, include but are not limited to, non-coding nucleic acids.

The term "mutant empty capsid" shall mean an empty capsid comprising a mutation that disrupts virus receptor binding. In one embodiment, a mutant empty capsid is a non-infective mutant capsid. In another embodiment, an empty capsid can absorb an antibody but cannot enter a target cell. In another embodiment, an empty capsid can absorb a neutralizing antibody. See C. J. Aalbers, et al., "Empty Capsids and Macrophage Inhibition/Depletion Increase rAAV Transgene Expression in Joints of Both Healthy and Arthritic Mice," *Human Gene Therapy*, 2017 February; 28(2): 168-1781; and Ayuso E, et al. "High AAV vector purity results in serotype- and tissue independent enhancement of transduction efficiency." *Gene Ther* 2010; 17:503-510.

The term "FXN gene insert" shall mean a gene insert comprising a nucleic acid sequence encoding FAN. In one embodiment, gene insert comprises a nucleic acid sequence encoding human FXN (hFXN). In one embodiment, the nucleic acid sequence encoding hFXN is an unmodified FXN cDNA. In one particular embodiment, the nucleic acid sequence encoding hFXN is a cDNA corresponding to the sequence of normal human frataxin mRNA described in Reference Sequence: NM_000144.4. (See J J Carvajal et al., "The Friedreich's ataxia gene encodes a novel phosphatidylinositol-4-phosphate 5-kinase" *Nat. Genet.* 14 (2), 157-162 (1996).)

The term "vector genome" or "vg" shall be broadly understood to encompass gene insert-containing vectors or virions. For convenience, "vector genomes" shall include, but shall not be limited to, gene insert-containing vectors or virions encapsulated within capsids such as AAV viruses and rAAV vectors and gene inserts, that are not encapsulated by capsids. For convenience gene insert-containing vectors or virions, that are not encapsulated by capsids include isolated gene insert-containing vectors or virions. See U.S. Pat. No. 9,598,703 "Capsid-free AAV vectors, compositions, and methods for vector production and gene delivery."

For quantitative purposes, "vg" is calculated as a count of gene insert-containing vectors or virions. In one example, of a single "vector genome" or single "vg" is a single gene insert or a single capsid carrying a gene insert-containing vector or virion. In another example, one AAV5.hFXN vector particle shall mean "1 vg," while about $5 \times 10^{14}$ vg shall mean about $5 \times 10^{14}$ AAV5.hFXN vectors.

The term "capsid particle" or "cp" shall be broadly understood to encompass any capsid. For convenience, the capsids may be full (e.g., encapsulating a gene insert) or empty. Capsid particles include, but not limited to, capsids carrying vector genomes (e.g., AAV viruses, and rAAV vectors), empty capsids, modified capsids, content-modified capsids, and mutant empty capsids.

For quantitative purposes, "cp" is calculated as a count of the total number of combined capsids carrying vector genomes (e.g., AAV viruses, and rAAV vectors, virions), empty capsids, modified capsids, content-modified capsids, and mutant empty capsids. In one example, "1 cp" shall mean one empty capsid, while about $1.76 \times 10^{12}$ cp shall mean about $1.76 \times 10^{12}$ empty capsids. In another example, a pharmaceutical formulation comprising 50% cp/cp empty capsids comprises 50 empty capsid particles per 100 total capsid particles (full and empty). In another example, a pharmaceutical formulation comprising 10% empty capsids can comprise a total of about $5.5 \times 10^{14}$ cp capsid particles, wherein the pharmaceutical formulation comprises about $5 \times 10^{14}$ vg AAV5.hFXN vectors and about $5 \times 10^{13}$ cp empty capsids.

The term "transduction" shall mean the transport of a gene to a cell by using a virus particle.

The term "effective amount" or "therapeutically effective amount" is an amount sufficient to affect a therapeutically beneficial or therapeutically desired result. A therapeutically effective amount can be administered in one or more administrations, applications or dosages.

The term "target point" or "target site" shall mean a location in the central nervous system (CNS) of a subject where the pharmaceutical formulation is administered. In one aspect, the target site is the cerebrospinal fluid (CSF) space. In one embodiment, the target site is the subarachnoid space. In another embodiment, the target site is the cerebroventricular space. In one embodiment, the target site is the brain. In another embodiment, the target site is the spine. In another embodiment, the target site is the cauda equina. A target site may optionally be the cerebrum, cerebellum, hippocampus, interior cortex, dorsal root ganglion, dentate nucleus, caudate nucleus, or cisterna magna. A target site may optionally be the sacral, lumbar, thoracic or cervical spine. The pharmaceutical formulation may be administered to one or more target sites.

The term "plasmid construct" shall mean a circular nucleic acid molecule that is used in combination with at least one other plasmid, to transfect a cell line in vitro to produce capsid particles. In one embodiment, the plasmid construct comprises: a nucleic acid sequence encoding hFXN (e.g., Human FXN cDNA); a Human Ubiquitin C (UBC) promoter; 5U2, which is a synthetic 5' regulatory element derived from the second intron of the canine sarcoplasmic/endoplasmic reticulum calcium ATPase gene and the 5' untranslated region of the bovine casein gene (U.S. Pat. No. 8,835,621); a Human Growth Hormone Poly A(hGH-Poly A); two AAV2 inverted terminal repeats (ITRs) flanking the AAV2 gene elements; and an antibiotic resistance gene.

As used herein, "nucleic acid," "nucleic acid molecule," "nucleic acid sequence," "oligonucleotide," "oligonucleotide sequence," "nucleotide sequence," "polynucleotide," and "polynucleotide sequence" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

As used herein, a "recombinant DNA molecule" is a DNA molecule that has undergone a molecular biological manipulation. DNA includes but is not limited to cDNA, genomic DNA, plasmid DNA, synthetic DNA, and semi-synthetic DNA.

As used herein, the term "fragment" used in connection with a polynucleotide sequence (e.g. "polynucleotide fragment") refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, polynucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, the term "chimeric" means comprised of fragments that are not contiguous in their natural state. For example, a chimeric polynucleotide means a polynucleotide comprising fragments that are not contiguous in their natural state.

As used herein, the term "synthetic" used in connection with a polynucleotide sequence is a non-natural polynucleotide (or portion of a polynucleotide) that differs from a wild-type polynucleotide sequence. For example, a synthetic gene (or portion of a gene) may contain one or more nucleic acid sequences not contiguous in nature (chimeric sequences), and/or may encompass substitutions, insertions, and deletions and combinations thereof.

As used herein, "gene" refers to a polynucleotide comprising nucleotides that encode a functional molecule (e.g., a polypeptide or RNA), and includes cDNA or genomic DNA nucleic acids. It is generally understood that genomic DNA encoding for a polypeptide or RNA includes non-coding regions (i.e. introns) that are spliced from mature mRNA, and are therefore not present in cDNA encoding for the same polypeptide or RNA. "Gene" may comprise a nucleic acid fragment that expresses a specific RNA, protein or polypeptide. The "gene" may further comprise regulatory sequences preceding (5' non-coding sequences) and following (3' non-coding sequences) the coding sequence. The "gene" may also comprise triplex-forming oligonucleotides (TFOs). "Native gene" refers to a gene as found in nature with its own regulatory sequences. "Chimeric gene" or "recombinant gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism.

A "foreign" gene or "exogenous" gene or "heterologous" gene or "transgene" refers to a gene not normally found in the host cell or organism, but that is introduced into the host cell or organism by gene transfer. Transgenes can comprise native genes inserted into a non-native organism, or chimeric or synthetic genes. A transgene may also be a cDNA version of an endogenous gene. A transgene gene may also be an unmutated version of an endogenous mutated gene or a mutated version of an endogenous unmutated gene. A transgene gene may also be a therapeutic gene or an experimental gene such as a reporter. A transgene can be directly introduced into the target cells of a host organism, or indirectly introduced by the transfer of transformed cells, e.g. autologous cells, into the host organism.

As used herein, the "5' untranslated region" or "5'UTR" of a gene is to be understood as that part of a gene which is transcribed into a primary RNA transcript (pre-mRNA) and which part is located upstream of the coding sequence. The primary transcript is the initial RNA product, containing introns and exons, produced by transcription of DNA. Many primary transcripts must undergo RNA processing to form the physiologically active RNA species. The processing into a mature mRNA may comprise trimming of the ends, removal of introns, capping and/or cutting out of individual rRNA molecules from their precursor RNAs. The 5'UTR of an mRNA is thus that part of the mRNA which is not translated into protein and which is located upstream of the coding sequence. In a genomic sequence, the 5'UTR is typically defined as the region between the transcription initiation site and the start codon. The 5' untranslated regions (5'UTRs) of vertebrate mRNAs may be a few tens of bases to several hundred bases in length (Crowe et al., 2006 BMC Genomics 7:16). A "synthetic 5'UTR" is a non-natural 5'UTR that differs from a wild-type 5'UTR polynucleotide sequence. A synthetic 5'UTR may contain one or more nucleic acid sequences not contiguous in nature (chimeric sequences), and/or may encompass substitutions, insertions, and deletions and combinations thereof.

As used herein, a "splice junction," "intron-exon splice junction," or "splice site" are regions at the boundaries of an intron in eukaryotic pre-mRNAs recognized by the cell's splicing apparatus where two neighboring exons are joined and the intron is deleted. Splice sites are represented by conserved sequences at the 5' and 3' intron/exon boundaries. For the vast majority of introns, the most conserved sequences are GU flanking the 5' end of the intron and AG flanking at the 3' end. However, exceptions to these consensus sequences are also known such as introns with AU-AC splice sites. The 5' splice site at an intron-exon boundary is known as a "splice donor" site. The 3' splice site at an intron-exon boundary is known as a "splice acceptor" site. A "spliceosome" is a large ribonucleoprotein complex that serves as the cell's splicing apparatus. The spliceosome is comprised of small nuclear ribonucleoproteins (snRNP) subunits that assemble on a pre-mRNA substrate. The snRNPs are themselves comprised of small nuclear RNAs (snRNAs) and several protein subunits. During the splicing reaction, recognition of splice sites within the pre-mRNA is performed through base-pairing with snRNAs.

As used herein, "heterologous" DNA refers to DNA not naturally located in the cell, or in a chromosomal site of the cell. Therefore, the heterologous DNA includes a gene foreign to the cell. "Heterologous" DNA may also include a gene naturally existing in the cell, but located in a non-native location. Furthermore, a "heterologous" DNA molecule may be a DNA molecule containing a non-host DNA segment, operably linked to a host DNA segment, for example, a transcription promoter. Conversely, a heterologous DNA molecule may comprise an endogenous gene operably linked with an exogenous promoter. Further, "heterologous" may refer to a DNA molecule or fragment that is derived from a gene that does not share a common evolutionary origin with a reference DNA molecule or fragment.

As used herein, the term "genome" includes chromosomal as well as mitochondrial, chloroplast and viral DNA or RNA.

As used herein, the term "probe" refers to a single-stranded nucleic acid molecule that can base pair with a complementary single stranded target nucleic acid to form a double-stranded molecule.

As used herein, a DNA "coding sequence" refers to a double-stranded DNA sequence that encodes a polypeptide and can be transcribed and translated into a polypeptide in a cell in vitro or in vivo or outside a cell, e.g., in a tube, when placed under the control of appropriate regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic, eukaryotic, or chimeric sequences, cDNA from mRNA, genomic DNA sequences, and even synthetic DNA sequences.

As used herein, "open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

As used herein, the term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription. The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

As used herein, the term "chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, the terms "restriction endonuclease" and "restriction enzyme" are used interchangeably and refer to an enzyme that binds and cuts within a specific nucleotide sequence within double stranded DNA.

As used herein, the terms "polypeptide," "peptide," and "protein" are used interchangeably and refer to a polymeric compound comprised of covalently linked amino acid residues.

As used herein, "polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase.

As used herein, the term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments. As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., (1987) *Cell* 50:667). Such proteins (and their encoding genes) have sequence homology, as reflected by their high degree of sequence similarity. However, in common usage and in the present application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., (1987) Cell 50:667). In one embodiment, two DNA sequences are "substantially homologous" or "substantially similar" when at least about 21% (preferably at least about 50%, and most preferably at least about 75%, 90%, 95%, 96%, 97%, 98%, or 99%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, infra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. MOLECULAR CLONING. A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a Tm of 55° C., can be used, e.g., 5×SSC, 0.1% SDS, 0.25% milk, and no formamide; or 300/% formamide, 5×SSC, 0.5% SDS. Moderate stringency hybridization conditions correspond to a higher Tm, e.g., 40% formamide, with 5× or 6×SSC. High stringency hybridization conditions correspond to the highest Tm, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In one embodiment, polynucleotides are detected by employing hybridization conditions comprising a hybridization step at Tm of 55° C., and utilizing conditions as set forth above. In another embodiment, the Tm is 60° C.; in certain embodiments, the Tm is 63° C. or 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. Another example of stringent conditions uses higher temperatures in which the washes are identical to those above except for the temperature of the final two 30 min washes in 0.2×SSC, 0.5% SDS was increased to 60° C. Still another example of highly stringent conditions uses two final washes in 0.I1×SSC, 0.1°% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In certain embodiments, the hybridization conditions comprise 2×SSPE and 63° C. for both the hybridization and washing steps.

The length for a hybridizable nucleic acid is, for example, at least about 10 nucleotides. A minimum length for a hybridizable nucleic acid may be at least about 15 nucleotides; at least about 20 nucleotides; or at least 30 nucleotides. Furthermore, the skilled artisan will recognize that the temperature and wash solution salt concentration may be adjusted as necessary according to factors such as length of the probe.

Substantially similar nucleic acid fragments of the present invention are those nucleic acid fragments whose DNA sequences are at least 70% identical to the DNA sequence of the nucleic acid fragments reported herein. Nucleic acid fragments of the present invention include those nucleic acid fragments whose DNA sequences are at least 80%, 900/%, 95%, 96%, 97%, 98%, and 99% identical to the DNA sequence of the nucleic acid fragments reported herein.

As used herein, the term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

As used herein, a "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., J. Mol. Biol. 215:403 410 (1993)); BLAST is publicly available on the World Wide Web. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20 to 30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 to 15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, the term "percent similarity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); BIOCOMPUTING: INFORMATICS AND GENOME PROJECTS (Smith, D. W., ed.) Academic Press, New York (1993); COMPUTER ANALYSIS OF SEQUENCE DATA, PART I (Griffin, A. M., and Griffin, H. G., eds.) Humana Press, N.J. (1994); SEQUENCE ANALYSIS IN MOLECULAR BIOLOGY (von Heinje, G., ed.) Academic Press (1987); and SEQUENCE ANALYSIS PRIMER (Gribskov, M. and Devereux, J., eds.) Stockton Press, New York (1991). Methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins et al., CABIOS. 5:151 153 (1989)) with the default parameters (GAP PENALTY=IO, GAP LENGTH PENALTY=IO). Default parameters for pairwise alignments using the Clustal method may be selected: KTUPLE 1, GAP PENALTY=3, WINDO W=5 and DIAGONALS SAVED=5.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., J. Mol. Biol. 215:403 410 (1990)), and DNASTAR (DNASTAR, Inc. 1228 S. Park St., Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

As used herein, the terms "expression" or "gene expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Factors (e.g., transcription factors) that are involved in up-regulation or down-regulation are often called "activators" and "repressors," respectively. For the purposes of the invention, a target gene may be down-regulated "post-transcriptionally" (i.e. at the level of the RNA transcript) through specific interaction with a down-regulating RNA molecule.

As used herein, the term "Transcriptional and translational control sequences" refer to DNA regulatory sequences, such as promoters, enhancers, terminators, and the like, that provide for the expression of a coding sequence in a host cell.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain. Examples of ecdysone-responsive systems are described in U.S. Pat. Nos. 7,091,038 and 6,258,603. In one embodiment, the system is the RHEOSWITCH THERAPEUTIC SYSTEM® (RTS®), which contains two fusion proteins, the DEF domains of a mutagenized ecdysone receptor (EcR) fused with a Gal4 DNA binding domain and the EF domains of a chimeric RXR fused with a VP16 transcription activation domain, expressed under a constitutive promoter.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and non-viral vehicles for introducing the nucleic acid into a host cell in vitro, ex vivo or in vivo. The term "vector" may also include minicircle DNAs. For example, the vector may be a plasmid without bacterial DNA sequences. The removal of bacterial DNA sequences which are rich in CpG regions has been shown to decrease transgene expression silencing and result in more persistent expression from plasmid DNA vectors (see e.g., Ehrhardt, A. et al. (2003) *Hum. Gene Ther.* 10: 215-25; Yet, N. S. (2002) *Mol. Ther.* 5: 731-38; Chen, Z. Y. et al. (2004) *Gene Ther.* 11: 856-64). The term "vector" may also include transposons such as Sleeping Beauty (Izsvak et al. (2000) *J. Mol. Biol.* 302:93-102), or artificial chromosomes.

A large number of vectors known in the art may be used to manipulate nucleic acids, incorporate response elements and promoters into genes, etc., or transfer a nucleic acid into a host cell. Possible vectors include, for example, plasmids or modified viruses including, for example bacteriophages such as lambda derivatives, or plasmids such as pBR322 or pUC plasmid derivatives, or the Bluescript vector. Larger vectors such as artificial chromosomes (bacteria (BAC), yeast (YAC), or human (HAC)) may be used to accommodate larger inserts. For example, the insertion of the DNA fragments corresponding to response elements or promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells transfected or transformed with the vector. A recombinant vector comprising a polynucleotide according to the invention may include one or more origins for replication in the cellular hosts in which their amplification or their expression is sought, markers or selectable markers.

As used herein, the term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify or select a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

As used herein, the term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), fluorescent proteins such as green fluorescent protein (GFP), chloramphenicol acetyltransferase (CAT), beta-galactosidase (LacZ), beta-glucuronidase (Gus), and the like. Selectable marker genes may also be considered reporter genes.

As used herein, the term "plasmid" refers to an extrachromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, a "cloning vector" refers to a "replicon," which is a unit length of a nucleic acid, e.g., DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). The term "expression vector" refers to a vector, plasmid or vehicle designed to enable the expression of an inserted nucleic acid sequence following transformation into a host cell. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the host cell are numerous and familiar to those skilled in the art.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, pCMV-EGFP available from Clontech. Many other vectors are well-known and commercially available.

For example, useful vectors, which comprise molecular insertion pivots for rapid insertion and removal of elements of gene programs, are described in U.S. Published Patent Application No. 2004/0185556, U.S. patent application Ser. No. 11/233,246 and International Published Application Nos. WO 2005/040336 and WO 2005/116231.

As used herein, the terms "promoter" and "promoter sequences" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions.

Promoters that cause a gene to be expressed in most cell types at most times are commonly referred to as "constitutive promoters." Promoters that cause a gene to be expressed in a specific cell type are commonly referred to as "conditional promoters." Non-limiting examples of conditional promoters are "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." Non-limiting examples of the inducible promoters are a TetO inducible promoter, heat shock protein promoter, metallothionein promoter, growth hormone promoter, and MMTV-LTR promoter. It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

Termination control regions, i.e., terminator or polyadenylation sequences, may also be derived from various genes native to the preferred hosts. Optionally, a termination site may be unnecessary, however, it can be included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

As used herein, the term "transfection" refers to the uptake of exogenous or heterologous RNA or DNA by a cell. A cell has been "transfected" by exogenous or heterologous RNA or DNA when such RNA or DNA has been introduced inside the cell. The transfected RNA or DNA can be integrated (covalently linked) into chromosomal DNA making up the genome of the host cell. "Transformation" refers to the transfer of a nucleic acid fragment into the genome of a host organism, resulting in genetically stable inheritance.

As used herein, the terms "modulate" and "modulates" mean to induce, reduce or inhibit nucleic acid or gene expression, resulting in the respective induction, reduction or inhibition of protein or polypeptide production.

As used herein, "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell.

"Stuffer sequences" comprised of non-coding polynucleotides ranging from 1001 to 3000 bp to ensure optimal genome packaging size for AAV, may be incorporated into the viral vectors of the invention.

The invention provides polynucleotides comprising a nucleic acid sequence encoding a frataxin protein. As used herein, a "frataxin protein" refers to a polypeptide that has the biological activity of frataxin and has an amino acid sequence that is at least 80% identical to the human frataxin sequence shown in SEQ ID NO: 1. In some embodiments, the polypeptide has an amino acid sequence that is at least 85% identical to SEQ ID NO: 1. In other embodiments, the polypeptide has an amino acid sequence that is at least 90% identical to SEQ ID NO: 1. In other embodiments, the polypeptide has an amino acid sequence that is at least 95% identical to SEQ ID NO:1. In other embodiments, the polypeptide has an amino acid sequence that is at least 96%, 97%, 98%, or 99% identical to SEQ ID NO: 1. In some embodiments, the polypeptide has the amino acid sequence of SEQ ID NO:1. The nucleic acids encoding the frataxin protein may be that shown in SEQ ID NO:2 or any sequence that encodes SEQ ID NO: 1 that differs from SEQ ID NO:2 due to the degeneracy of the genetic code. Nucleic acids that encode the variants of the frataxin protein may be a nucleic acid that encodes a polypeptide has an amino acid sequence that is at least 80%, 85%, 90%, 91%, 92%, 93%, 940%, 95%, 96%, 97%, 98%, or 99% identical to SEQ ID NO:1.

Nucleic Acid Molecules

Frataxins

Friedreich's Ataxia (FRDA) is linked to a deficiency of frataxin (FXN), a mitochondrial protein involved in iron-sulfur cluster synthesis. The frataxin proteins that are useful in the invention are full-length frataxin proteins, functional truncations, functional variants and functional analogues. By "functional" it is meant that the frataxin used in the invention retains frataxin activity sufficient to alleviate at least one symptom of Friedreich's ataxia. The frataxin protein sequence preferably contains a portion at the N-terminus that directs the protein for translocation into the mitochondria. Mitochondrial localization sequences (also called "transit peptides") are known in the art. The frataxin localization sequence is amino acids 1-41 of SEQ ID NO:1. This sequence could be substituted by other mitochondrial translocators whose sequences are known in the art. SEQ ID NO:1 shows the frataxin preproprotein for which amino acids 1-41 constitute the transit peptide, amino acids 42-210- constitute the proprotein, and amino acids 56-210 constitute the mature protein.

In a detailed study of the frataxin protein, Faraj et al. investigated the structural-functional relationship of the C-terminal region (CTR) or frataxin and the effect of alterations on the stability of the frataxin protein (Faraj, S. E. et al. (2014) *FEBS J.* 281(15):3397-3419) (incorporated by reference herein in its entirety). Faraj et al. found that a certain mutant with a L198R mutation or a complete truncation from 81-193 was sufficient to cause Friedreich's ataxia. Other mutants such as a L203C mutation increased the stability of the protein. In another study for her Master's Thesis for Texas A&M University (2013), Melissa Thorstad found that FXN β4 and β5 sheets residues Q153, W155, and R165 were implicated as vital for SDU binding, and residues N146, Q148, Q153, and W155 appeared to be essential for SDU activation. Thus, functional frataxin proteins of use in the invention include those that maintain the structure and stability of the frataxin CTR, one example being the L203C variant. In general, the frataxin protein that is useful in the invention has an amino acid sequence is at least 80%, 85%, 90%, 91%, 92%, 93%, 94%, 95%, 96%, 97%, 98%, 99% or 100%/6 identical to that of SEQ ID NO: 1 provided that certain residues, including a transit peptide and pro-sequence (amino acids 42-55 of SEQ ID NO:1), and Q153, W155, R165, N146, Q148, Q153, and W155, are included. Such frataxin proteins may be determined by one of skill in the art using the methods of Faraj et al. and assessing stability and structure of the CTR, and maintaining critical residues as described by Faraj and Thorstad.

Promoters

Promoters, which are useful to drive expression of a nucleic acid in the desired host cell are numerous and familiar to those skilled in the art. Virtually any promoter capable of driving expression of the polynucleotide encoding frataxin can be used in an expression vector, including but not limited to, viral promoters, bacterial promoters, animal cell promoters, mammalian cell promoters, synthetic promoters, constitutive promoters, tissue-specific promoters, pathogenesis or disease related promoters, developmental specific promoters, inducible promoters, and light regulated promoters. Animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK1) promoter, a ubiquitin (UBC) promoter, an albumin promoter, the regulatory sequences of the mouse metallothionein-L promoter and transcriptional control regions, the ubiquitous promoters (HPRT, vimentin, (x-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as myelin basic protein gene control region active in oligodendrocyte cells in the brain, myosin light chain-2 gene control region active in skeletal muscle. In addition, these expression sequences may be modified by addition of enhancer or regulatory sequences and the like. In the polynucleotides of the invention, the frataxin gene is operably linked to a promoter to drive transcription of the frataxin gene. The promoter may be any known promoter that has the effect of driving transcription of the frataxin gene. In certain specific examples of such promoters include, but are not limited to a CMV promoter, a UBC promoter, an EF1α promoter, a PGK1 promoter and a minimal frataxin promoter. In specific embodiments, the polynucleotide encoding frataxin is operably linked to a UBC promoter, such as, for example that shown in SEQ ID NO:3.

5' Regulatory Elements

In the polynucleotide comprising a frataxin gene, the polynucleotide preferably comprises at least a portion of a 5' untranslated region (5'UTR) operably linked to the frataxin gene wherein the 5'UTR may be from any mammalian species. Non-limiting 5'UTRs which could be used include the 5'UTR from a human frataxin gene, a bovine frataxin gene, a mouse frataxin gene, a rat frataxin gene, a sheep frataxin gene, a monkey frataxin gene, a goat frataxin gene, a horse frataxin gene, a pig frataxin gene, a camel frataxin gene, a cat frataxin gene, or a dog frataxin gene.

In certain embodiments, at least a portion of a non-frataxin 5'UTR is used. Examples of non-frataxin 5'UTRs include, but are not limited to a glyceraldehyde 3-phosphate dehydrogenase 5' regulatory element (GAPDH) (e.g., SEQ ID NO: 15), a synthetic 5' regulatory element (such as those described in U.S. Pat. No. 8,835,621, which is incorporated by reference herein in its entirety, including 5U2 (SEQ ID NO:4)), a 60S ribosomal protein L5 5' regulatory element (RPL6-5' Splice) (e.g., SEQ ID NO:16), and a Ferritin heavy chain 5' regulatory element (FTH1-5'UTR) (e.g., SEQ ID NO: 14).

In some embodiments, the 5'UTR may be at least about 25 nucleotides in length. In other embodiments, the 5'UTR may be at least about 30, 35, 40, 45, 50, 55, 60, 65, 70, 75, 85, 90, 95, 100, 105, 110, 115, 120, 125, 130, 135, 140, 145, 150, 155, 160, 165, 170, 175, 185, 190, 195, 200 or more nucleotides in length. In another embodiment, the polynucleotide fragment comprising a frataxin gene 5'UTR may represent at least about 50% of the natural 5'UTR sequence. In other embodiments, the polynucleotide fragment comprising a frataxin gene 5'UTR may represent at least about 55%, 60%, 65%, 70%, 75%, 80%, 85%, 90%, 95%, 98% or more of the natural 5'UTR sequence. In another embodiment, the polynucleotide fragment comprising a frataxin gene 5'UTR may represent the entire natural 5' UTR sequence.

3' Regulatory Elements

In the polynucleotide comprising a frataxin gene, the polynucleotide preferably comprises a 3' regulatory region operably linked to the frataxin gene, wherein the 3' regulatory region may be from any mammalian species. In certain embodiments, the polynucleotide comprising a frataxin gene additionally comprises a 3' regulatory element such as a human growth hormone polyadenylation signal (hGHpA) (e.g., SEQ ID NO:5), a Simian virus 40 early polyadenylation region (SV40 early) (e.g., SEQ ID NO:8), a Simian virus 40 late polyadenylation region (SV40 late) (e.g., SEQ ID NO:9), and a synthetic 3' regulatory element (such as SEQ ID NO:7).

Vectors

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, and the like.

A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the invention is the ULTRAVECTOR® Production System (Intrexon Corp., Blacksburg, Va.) as described in WO 2007/038276. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in both cells and animals. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., (1992) *J. Biol. Chem.* 267:963; Wu et al., (1988) *J. Biol. Chem.* 263:14621; and Hartmut et al., Canadian Patent Application No. 2,012,311).

A polynucleotide according to the invention can also be introduced in vivo by lipofection. (Feigner et al., (1987) *Proc. Natl. Acad. Sci. USA* 84:7413; Mackey et al., (1988) *Proc. Natl. Acad. Sci. USA* 85:8027; and Ulmer et al. (1993) *Science* 259:1745; Feigner et al. (1989) *Science* 337:387). Various lipid compounds and other compositions for transfer of nucleic acids are known in the art, including, but not limited to those described in PCT Publication Nos. WO 95/18863, WO 96/17823, U.S. Pat. No. 5,459,127, WO 95/21931, WO 96/25508, and WO 95/21931.

It is also possible to introduce a vector in vivo as a naked DNA plasmid as described in U.S. Pat. Nos. 5,693,622, 5,589,466 and 5,580,859.

In certain embodiments, the polynucleotides of the invention may be incorporated into a viral vector for deliver to a subject. Non-limiting examples of viral vectors include adenoviral vectors, retroviral vectors, lentiviral vectors, herpesvirus vectors and adeno-associated virus (AAV) vectors.

In particular embodiments, the polynucleotides of the invention are provided in adeno-associated viral (AAV) vectors. The adeno-associated viral vector may be AAV1, AAV2, AAV3, AAV4, AAV5, AAV6, AAV7, AAV8, AAV9, AAVrh10 or any other serotypes of AAV that can infect humans. In certain specific embodiments, the Adeno-associated viral vector is AAV5.

AAV vectors are vectors derived from an adeno-associated virus serotype. AAV vectors can have one or more of the AAV wild-type genes deleted in whole or part, preferably the rep and/or cap genes, but retain functional flanking ITR sequences. AAV vectors include at least those sequences required in cis for replication and packaging (e.g., functional ITRs) of the virus. The nucleotide sequences of AAV ITR regions are known (Kotin, R M (1994) *Hum. Gene Ther.* 5(7):793-801; Berns, K I "Parvoviridae and their Replication" in V IROLOGY, 2nd Edition, (Fields, B N and Knipe, DM, eds.) New York: Raven Press; 1990b: 1743-1763). The ITRs may be derived from different serotypes so long as they are functional. The AAV expression vectors of the invention may be constructed by any means known in the art to operatively link components in the direction of transcription, (i.e., control elements including promoter, 5'UTR, the frataxin gene, and 3' regulatory element (such as a transcriptional termination region)).

In one particular aspect, the invention is directed to a vector comprising AAV serotype 5 (AAV5) and a FXN gene insert. In one embodiment, the vector is a AAV5-hFXN vector comprising an rAAV5 capsid, and a complementary DNA (cDNA) sequence encoding hFXN.

Figure 15:
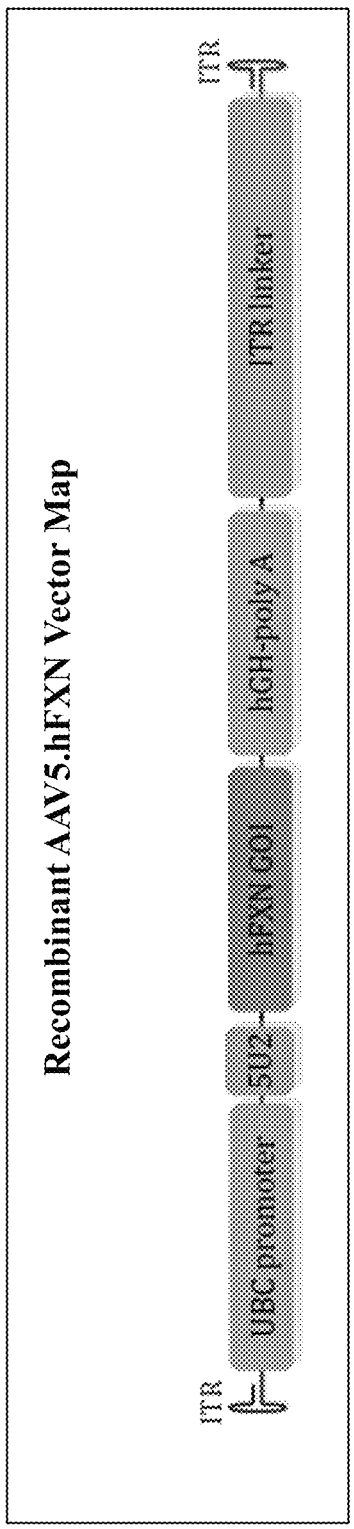
FIG. 15 shows a Recombinant AAV5.hFXN Vector Map. Ubiquitin C promoter (UBC promoter), a 5' regulatory element (5U2), unmodified hFXN cDNA (hFXN GOI), a human growth hormone polyadenylation 3' regulatory element (hGH-poly A), and an ITR linker. The entire sequence is flanked by AAV Inverted Terminal Repeats (ITR).
Figure 17:
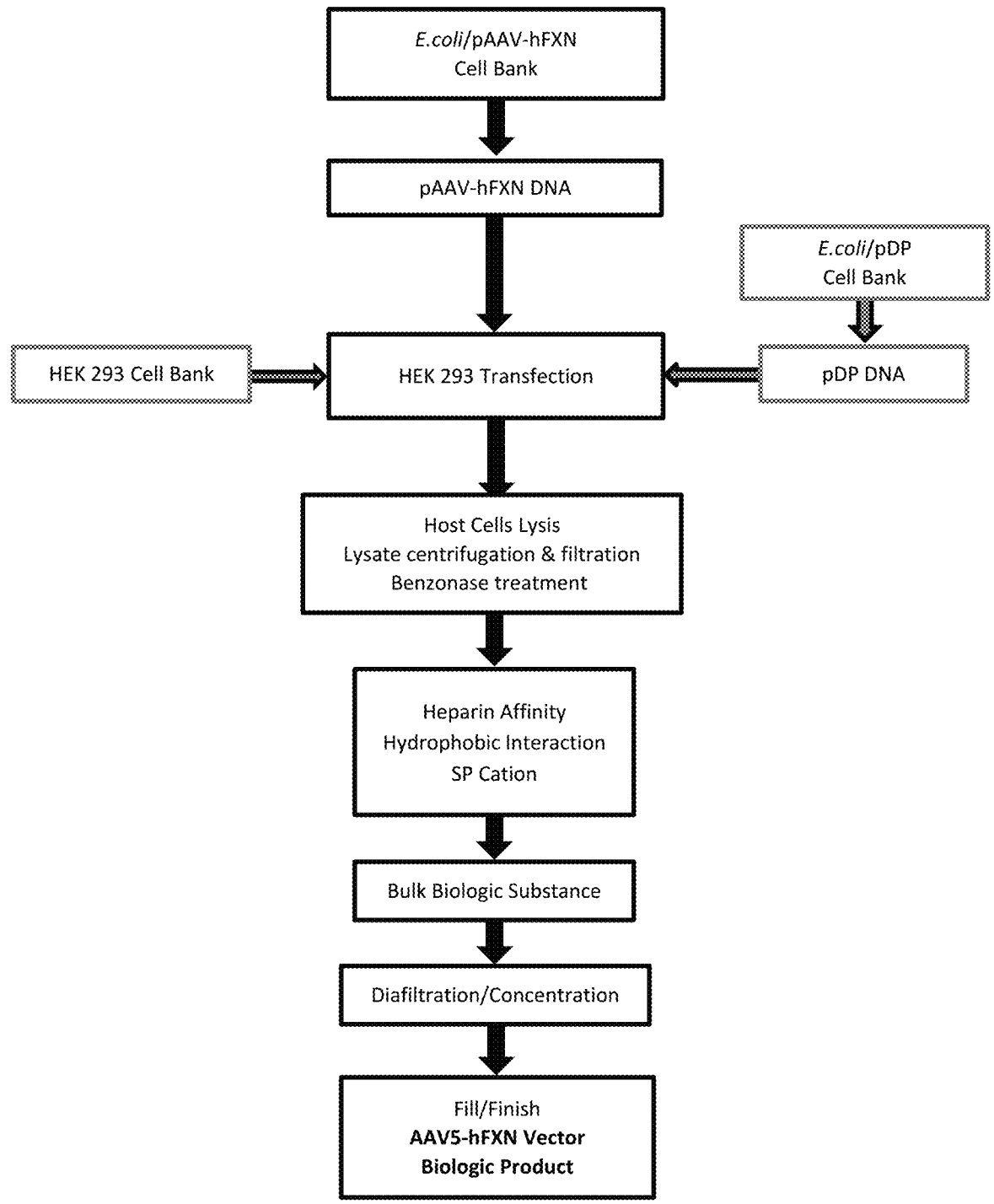
FIG. 17 shows a Schematic Overview of an AAV5.hFXN Vector Manufacturing Process.
Figure 18:
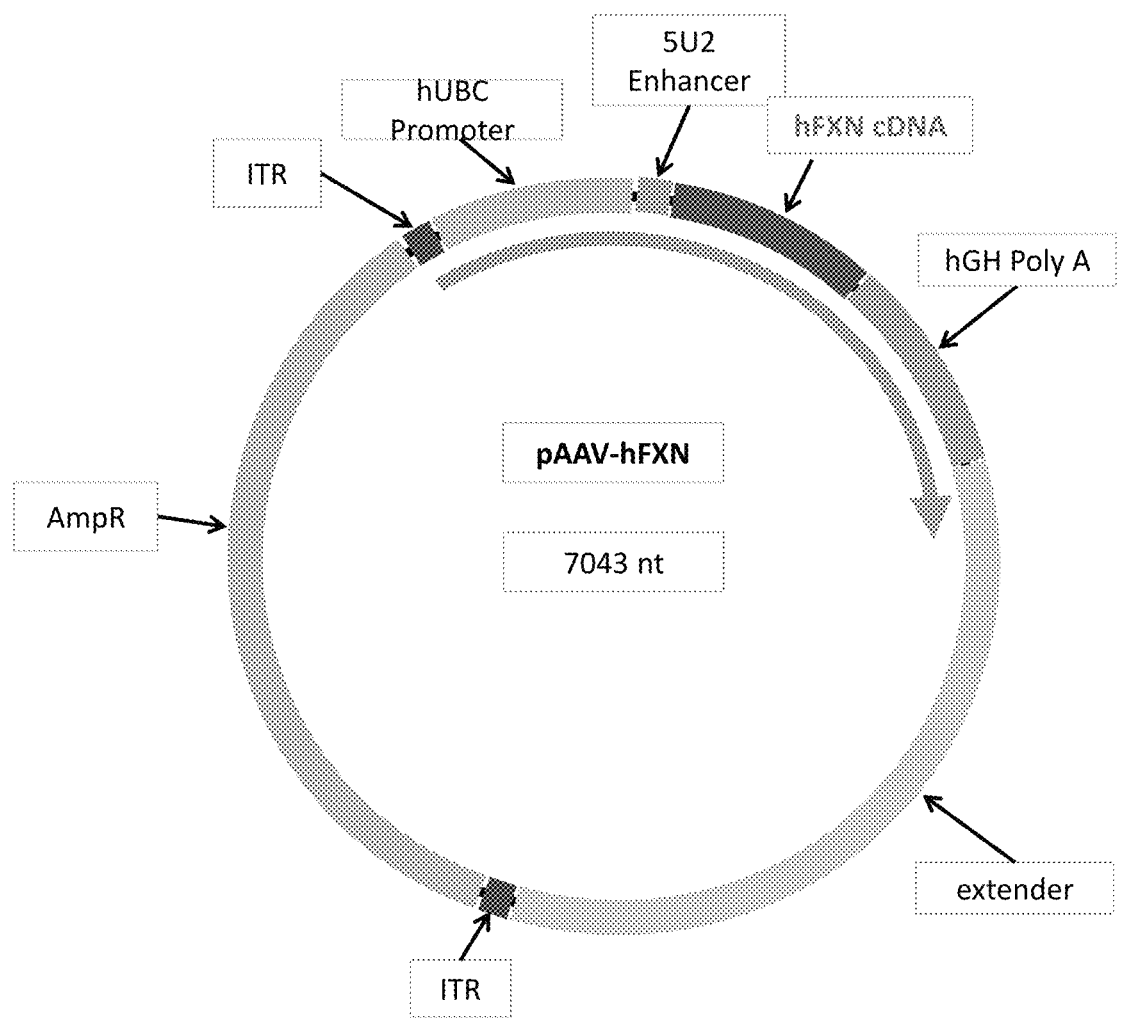
FIG. 18 shows a Schematic Plasmid Map of pAAV5-hFXN DNA.

An example of an AAV5.hFXN vector with gene insert is shown in FIG. 15.

//-ITR-UBC-5U2-hFXN GOI-hGH-Poly A-ITR Linker-ITR-//

ITR=AAV2 inverted terminal repeat,
UBC=Human Ubiquitin C (UBC) promoter
5U2=Synthetic 5' regulatory element
hFXN GOI=Human FXN cDNA
hGH-Poly A=Human Growth Hormone Poly A Recombinant viruses comprising the frataxin constructs may be produced by any technique known in the art, including but not limited to transfecting packaging cells (e.g., PA317 cells, PsiCRIP cells, GPenv+ cells, 293 cells) or transient transfection with helper plasmids or viruses. Description and protocols for making replication-defective recombinant viruses may be found, for example, in WO 94/19478, WO 95/14785, WO 96/22378, U.S. Pat. Nos. 5,882,877, 6,013,516, 4,861,719, and 5,278,056.

In a specific embodiments of the invention, the polynucleotide comprises a nucleic acid encoding a Frataxin protein having the amino acid sequence of SEQ ID NO:1 operably linked to a UBC promoter (SEQ ID NO:3) and a 5U2 5'UTR (SEQ ID NO:4) and a synthetic 3' regulatory element (SEQ ID NO:7). In another specific embodiments of the invention, the polynucleotide comprises a nucleic acid encoding a Frataxin protein having the amino acid sequence of SEQ ID NO:1 operably linked to a UBC promoter (SEQ ID NO:3) and a 5U2 5'UTR (SEQ ID NO:4) and an hGHpA 3' regulatory element (SEQ ID NO:5). In certain embodiments of the invention, each of these two polynucleotides is incorporated into an AAV5 vector, thereby making two types of AAV5 vectors to express frataxin. In other particular embodiments, each of these types of AAV5 vectors to express frataxin is packaged into virions, making two types of rAAV5s for expressing frataxin, each of which may optionally be formulated into compositions of the invention.

Pharmaceutical Formulation

Optionally, the AAV5.hFXN vector is formulated in phosphate buffered saline (PBS), 1×PBS, 2×PBS, 10×PBS, Dulbecco's PBS (DPBS), or DPBS which does not comprise Magnesium or Calcium.

In one embodiment, the pharmaceutical formulation comprises a AAV5.hFXN vector, and 1×PBS. In another embodiment, the pharmaceutical formulation comprises a AAV5.hFXN vector, 1×DPBS, and about 200 mM NaCl.

In one aspect, the pharmaceutical formulation has a pH substantially similar to the pH of human cerebral spinal fluid. In one embodiment, the pharmaceutical formulation has a pH from about 6.5 to about 7.5. In another embodiment, the pharmaceutical formulation has a pH from about 6.8 to about 7.2. In another embodiment, the pharmaceutical formulation has a pH from about 7.0 to about 7.5. In another embodiment, the pharmaceutical formulation has a pH of about 7. In another embodiment, the pharmaceutical formulation has a pH of about 7.1. In another embodiment, the pharmaceutical formulation has a pH of about 7.2. In another embodiment, the pharmaceutical formulation has a pH of about 7.2. In another embodiment, the pharmaceutical formulation has a pH of about 7.4.

In one particular embodiment, the pharmaceutical formulation comprises AAV5.hFXN vector, 0.154M NaCl, 0.056M $Na_2HPO_4$, and 0.0106 M $KH_2PO_4$. In another particular embodiment, the pharmaceutical formulation comprises AAV5.hFXN vector, 0.337M NaCl, 0.027 M KCl, 0.015M $Na_2HPO_4$, and 0.0015M $KH_2PO_4$.

Examples of pharmaceutical formulations include, but are not limited to, the pharmaceutical formulations shown in Table 2.

TABLE 2

Example AAV5.hFXN Formulations

| Component | Formulation 1 | Formulation 2 |
|---|---|---|
| AAV5-hFXN | $2.5 \times 10^{11}$ vg/mL | $2.5 \times 10^{12}$ vg/mL |
| Excipients | PBS | Dulbecco's PBS (no Mg, no Ca) + 200 mM NaCl |
| pH | 7.4 | 7.0 |

In one aspect, the pharmaceutical formulation comprises empty capsids at a percentage of at most about 25% to about 95% cp/cp. In some embodiments, the pharmaceutical formulation comprises empty capsids at a percentage of at most about 50% cp/cp to about 75% cp/cp. In other embodiments, the pharmaceutical formulation comprises empty capsids at a percentage of at most about 25% cp/cp to about 50% cp/cp. In some embodiments, the pharmaceutical formulation comprises empty capsids at a percentage of at most about 95% cp/cp. In some embodiments, the pharmaceutical formulation comprises empty capsids at a percentage of 0% to at most about 25% cp/cp. The ranges herein include all whole numbers between the stated numbers (e.g., 25% to 50%, includes 25%, 26%, 27%, 28%, etc., up to and including 50/o). In some embodiments, the pharmaceutical formulation is substantially free of empty capsids. As used herein, "substantially free" means refers to a formulation that has little or no amount of the component. "Substantially free of empty capsids" refers to a formulation that has 1% to 0% empty capsids.

Route of Administration; Delivery of Pharmaceutical Formulation:

In one aspect, the pharmaceutical formulation is administered by intrathecal (IT) delivery. In another aspect, the pharmaceutical formulation is administered by intracerebroventricular (ICV) delivery. In another aspect, the pharmaceutical formulation is administered by intraparenchymal delivery.

In one embodiment, the pharmaceutical formulation is administered by intraparenchymal delivery to the brain. In one embodiment, the pharmaceutical formulation is administered by intraparenchymal delivery to the cerebellum. In another embodiment, the pharmaceutical formulation is administered by intraparenchymal delivery to the cerebrum. In another embodiment, the pharmaceutical formulation is administered by intraparenchymal delivery into the dentate nucleus. In another embodiment, the pharmaceutical formulation is administered by intraparenchymal delivery into the dorsal root ganglion.

The pharmaceutical formulation may be administered using any suitable delivery device including, but not limited to, needle, catheter or related device. The pharmaceutical formulation may be administered using any suitable techniques known in the art, including, but not limited to, stereotactic injection (see Davidson et al., "Recombinant adeno-associated virus type 2, 4, and 5 vectors: Transduction of variant cell types and regions in the mammalian central nervous system" PNAS 97:3428-3432, 2000; and Alisky et al., "Gene therapy for amyotrophic lateral sclerosis and other motor neuron diseases" Hum. Genre Ther. 11:2315-2329, 2000).

In one embodiment, the pharmaceutical formulation is administered using a single bolus injection. In another embodiment, the pharmaceutical formulation is administered using a continuous infusion. In another embodiment, the pharmaceutical formulation is administered using multiple injections. In another embodiment, the pharmaceutical formulation is administered using one injection, two injections, three injections, or four injections.

In one embodiment, the pharmaceutical formulation is administered bilaterally. In another embodiment, the pharmaceutical formulation is administered bilaterally. In one particular embodiment, the pharmaceutical formulation is administered as a bilateral injection to the cerebellum.

The pharmaceutical formulation can be delivered by manual injection, by an infusion pumps or by an osmotic pump. Non-manual injection includes, but in not limited to, convection enhanced delivery (CED). Reference is made to L. Samaranch et al., "MR-guided parenchymal Delivery of Adeno-Associated Viral Vector Serotype 5 in Non-Human Primate Brain" *Gene Therapy* (2017) 24, 253-261; and U.S. Pat. No. 9,701,984 "CNS targeting AAV Vectors and Methods of use Thereof." Both osmotic and infusion pumps are commercially available from a variety of suppliers, for example Alzet Corporation, Hamilton Corporation, Alza, Inc., Palo Alto, Calif. One non-limiting example of a syringe pump is a Pump 11 Elite Series, Harvard Pump, Harvard Apparatus Holliston, Mass. One non-limiting example of a syringe pump is a Legato™ Syringe Pump, KD Scientific Inc. Holliston, Mass.

Any suitable Cannulas or needle may be used. Any suitable tip style may be used. The cannula or needle may optionally include one or more tapered regions. In various embodiments, the cannula or needle may be beveled.

Example Spinal Needles include, but are not limited to, Pencil-Point (Pencan®—Braun; Reganesth®—Sarstedt AG; Whitacre; Sprotte) and Quincke (Spinocan®—Braun) type bevel needles.

Any suitable dimensions of cannula or needle may be used. Dimensions may depend on the site for implantation. For example, the width of the epidural space is only about 3-5 mm for the thoracic region and about 5-7 mm for the lumbar region. Examples of lengths of the cannula or needle may include, but are not limited to, from about 15 to 150 mm in length, for example, about 65 mm for epidural pediatric use, about 85 mm for a standard adult and about 110 mm for an obese adult patient. Example thicknesses of the cannula or needle, include, but is not limited to, from about 0.05 mm to about 2 mm.

Any suitable gauge of cannula or needle may be used. Examples include but are not limited to, about 14G to about 22G. In some embodiments, the gauge of the needle or cannula is about 18 to about 22G.

Examples of ICV access devices include but are not limited to, Ommaya and Rickham reservoirs. Reference is made to J. L. Cohen-Pfeffer et al., "Intracerebroventricular Delivery as a Safe, Long-Term Route of Drug Administration" *Pediatric Neurology*, Volume 67, February 2017, Pages 23-35; "Safety of Ommaya reservoirs in children with brain tumors: a 20-year experience with 5472 intraventricular drug administrations in 98 patients" *J Neurooncol.*, 120

(2014), pp. 139-145; A. Desi et al., "Gibaldi's Drug Delivery Systems In Pharmaceutical Care," American Society of Health-System Pharmacists, 2007; and Cook A M, et al., Intracerebroventricular administration of drugs. Pharmacotherapy. 2009 July; 29(7):832-45.

In one another embodiment, the pharmaceutical formulation is administered by Intrathecal delivery via lumbar puncture into the CSF using the Medtronic ASCENDA™ Intrathecal Catheter delivery system. In one particular embodiment, the pharmaceutical formulation is administered by inserting a catheter to the subarachnoid space and administering ½ the dose of the pharmaceutical formulation to the lumbar and ½ the dose of the pharmaceutical formulation to the cisterna *magna*.

In one embodiment, the ASCENDA™ 8781 Intrathecal Catheter delivery system kit includes, but is not limited to: Spinal segment with inserted guide wire, Pump segment with attached sutureless pump connector, Catheter connector with 2 attached collets, 16 T-gauge introducer needle (11.4 cm). Anchor with anchor dispenser. Length: Total catheter 139.7 cm, Spinal segment 66.0 cm, Pump segment 73.7 cm. Spinal segment: Outer diameter 1.2 mm (4 French), Inner diameter 0.5 mm, Interval marker 1 cm, Catheter tip Closed with 6 side holes. Pump segment: Outer diameter (catheter only) 1.2 mm (4 French), Inner diameter 0.5 mm (catheter only), Interval markerl cm interval. Catheter volume: 0.0022 mL/cm. Catheter connector: inner diameter 0.3 mm, Collet outer diameter 4.3 mm, Guide wire: outer diameter 0.5 mm, Introducer needle 16 T-gauge, 11.4 cm. Trimmable segments: Catheter connector ends of the spinal and pump segments Pump segment to spinal segment separation force >10.0 N. Sutureless pump connector to pump separation force: >10.0 N.

The pharmaceutical formulation is optionally delivered by catheter and infusion pump. Any catheter and pump combination suitable for CNS infusion is optionally used. One non-limiting example of a catheter and pump combination is the Medtronic ASCENDA™ Intrathecal Catheter delivery system. Examples of useful pumps include but are not limited to Medtronic SynchroMed®EL 18 mL, SynchroMed® II 20 mL, and SynchroMed® II 40 mL pumps.

In another embodiment, the pharmaceutical formulation is optionally delivered by Alcyone MEMS Cannula (AMC™, Alcyone Lifesciences, Inc., Lowel, Mass.), a dual-lumen, MR-compatible injection and aspiration neuro-ventricular cannula. In another embodiment, the pharmaceutical formulation is optionally delivered by Alcyone Pulsar intrathecal catheter.

Container:

In one embodiment, the pharmaceutical formulation is contained in a pharmaceutical-grade borosilicate glass container with a fluoropolymer lined plastic closure. Examples of fluoropolymers include, but are not limited to, polytetrafluoroethylene (PTFE) (Teflon®), polyethylenetetrafluoroethylene (ETFE). (Fluorotec®), and a copolymer of ethylene and tetrafluoroethylene (Tefzel®). In one embodiment, the closure is lined with polytetrafluoroethylene (PTFE) (Teflon®).

Dose:

Dosages of the vector depend upon factors, including but not limited to, the mode of administration, the individual subject's condition, and the particular vector delivered.

In one embodiment of the instant invention, the dose per subject ranges from about $1 \times 10^{10}$ vg to about $1 \times 10^{15}$ vg. In another embodiment, the dose is at least about $1 \times 10^{11}$ vg, at least about $1 \times 10^{12}$ vg, at least about $1 \times 10^{13}$ vg, at least about $1 \times 10^{14}$ vg, or at least about $1 \times 10^{15}$ vg.

In another embodiment, the dose is at least about $5 \times 10^{13}$ vg, at least about $1.5 \times 10^{14}$ vg, or at least about $5 \times 10^{14}$ vg.

In another embodiment, the dose is about $5 \times 10^{13}$ vg, about $1.5 \times 10^{14}$ vg, or about $5 \times 10^{14}$ vg.

In another embodiment, the dose is an amount of about $3.7 \times 10^{10}$ vg/g on a brain weight basis, about $1.11 \times 10^{11}$ vg/g on a brain weight basis, or about $3.7 \times 10^{11}$ vg/g on a brain weight basis.

The dose is a total dose per subject per administration over all target sites.

For one non-limiting example, a total dose per subject of about $5 \times 10^{13}$ vg includes two injections of about $2.5 \times 10^{13}$ vg (i.e., one $2.5 \times 10^{13}$ vg injection in the right half of the cerebellum and one $2.5 \times 10^{13}$ vg injection left half of the cerebellum). For another non-limiting example, a total dose per subject of about $1.5 \times 10^{14}$ vg includes two injections of about $7.5 \times 10^{13}$ vg (i.e., one $7.5 \times 10^{13}$ vg injection in the right half of the cerebellum and one $7.5 \times 10^{13}$ vg injection in the left half of the cerebellum). For another non-limiting example, a total dose per subject of about $5 \times 10^{14}$ vg includes two injections of about $2.5 \times 10^{14}$ vg (i.e., one $2.5 \times 10^{14}$ vg injection in the right half of the cerebellum and one $2.5 \times 10^{14}$ vg injection left half of the cerebellum).

For another non-limiting example, a total dose per subject of about $5 \times 10^{13}$ vg includes two injections of about $2.5 \times 10^{13}$ vg (i.e., one $2.5 \times 10^{13}$ vg injection at the Lumbar and one $2.5 \times 10^{13}$ vg injection at the cisterna magna). For another non-limiting example, a total dose per subject of about $1.5 \times 10^{14}$ vg includes two injections of about $7.5 \times 10^{13}$ vg (i.e., one $7.5 \times 10^{13}$ vg injection at the Lumbar and one $7.5 \times 10^{13}$ vg injection at the cisterna magna). For another non-limiting example, a total dose per subject of about $5 \times 10^{14}$ vg includes two injections of about $2.5 \times 10^{14}$ vg (i.e., one $2.5 \times 10^{14}$ vg injection at the Lumbar and one $2.5 \times 10^{14}$ vg injection at the cisterna magna).

Reference is made to D. J. Schuster, "Supraspinal gene transfer by intrathecal adeno-associated virus serotype 5." *Front. Neuroanat.* (2014b), 8:66; S. J. Gray. "Global CNS gene delivery and evasion of anti-AAV-neutralizing antibodies by intrathecal AAV administration in non-human primates." *Gene Ther.* 2013; 20(4):450-459.: T. Federici, et al., "Robust spinal motor neuron transduction following intrathecal delivery of AAV9 in pigs," *Gene Ther,* 19(8):852, 2012; and B. Snyder, et al., "Comparison of adeno-associated viral vector serotypes for spinal cord and motor neuron gene delivery," *Hum. Gene Ther,* 22(9): 1129, 2011.

Dose Volume:

In one embodiment, the pharmaceutical formulation is delivered at a dose volume ranging from about 0.1 mL to about 10 mL per target site. In another embodiment, the pharmaceutical formulation is delivered at a dose volume ranging from about 1 mL to about 5 mL per target site. In another embodiment, the pharmaceutical formulation is delivered at a dose volume ranging from about 1 mL to about 3 mL per target site. In another embodiment, the pharmaceutical formulation is delivered at a dose volume ranging from about 1.5 mL to about 2.5 mL per target site. In another embodiment, the pharmaceutical formulation is delivered at a dose volume ranging from about 1 mL to about 2 mL per target site. In one particular embodiment, the pharmaceutical formulation is delivered at a dose volume of about 1 mL per target site. In another particular embodiment, the pharmaceutical formulation is delivered at a dose volume of about 2 mL per target site. In another particular embodiment, the pharmaceutical formulation is delivered at a dose volume of about 3 mL per target site.

Dose Concentration:

In one embodiment, the pharmaceutical formulation comprises an AAV5.hFXN vector concentration of about $1\times10^9$ to about $2\times10^{13}$ vg/mL. In some embodiments, the AAV5.hFXN vector concentration is about $1\times10^{10}$ to about $2\times10^{13}$. In other embodiments, the AAV5.hFXN vector concentration is about $1\times10^{11}$ to about $2\times10^{13}$. In other embodiments the AAV5.hFXN vector concentration is about $1\times10^{12}$ to about $2\times10^{13}$ vg/mL. In another embodiment, the AAV5.hFXN vector concentration is about $2.5\times10^{12}$ to about $2\times10^{13}$ vg/mL. In other embodiments, the AAV5.hFXN vector concentration is about $5\times10^{12}$ to about $2\times10^{13}$ vg/mL. In still further embodiments, the AAV5hFXN vector concentration is about $7\times10^{12}$ to about $2\times10^{13}$ vg/mL.

In certain embodiments, the AAV5.hFXN vector concentration is at least about $1\times10^9$, at least about $1\times10^{11}$, at least about $2.5\times10^{11}$, at least about $5\times10^{11}$, at least about $1\times10^{12}$, at least about $2\times10^{12}$, at least about $2.5\times10^{12}$, at least about $5\times10^{12}$, at least about $7\times10^{12}$, at least about $1\times10^{13}$, or at least about $2\times10^{13}$ vg/mL.

In one embodiment, the pharmaceutical formulation comprises a AAV5.hFXN vector concentration of concentration of about $1\times10^9$ vg/mL, about $1\times10^{10}$ vg/mL, about $1\times10^{11}$ vg/mL, about $1\times10^{12}$ vg/mL, about $1\times10^9$ vg/mL, about $2.5\times10^{11}$ vg/mL, about $5\times10^{11}$ vg/mL, about $2\times10^{12}$ vg/mL, about $2.5\times10^{12}$ vg/mL, about $5\times10^{12}$ vg/mL, about $7\times10^{12}$ vg/mL, about $1\times10^{13}$ vg/mL, or about $2\times10^{13}$ vg/mL.

Rate of Administration:

In one embodiment, the pharmaceutical formulation is delivered as a single bolus injection over about one minute to about 10 minutes. In one embodiment, the pharmaceutical formulation is delivered as a single bolus injection over about 1 minute, to about 5 minutes.

In one embodiment, the pharmaceutical formulation is delivered at a rate ranging from of about 0.001 mL/min to about 10 mL/min. In another embodiment, the pharmaceutical formulation is delivered at a rate ranging from of about 0.01 mL/min to about 1 mL/min. In another embodiment, the pharmaceutical formulation is delivered at a rate ranging from of about 0.01 mL/min to about 0.1 mL/min. In another embodiment, the pharmaceutical formulation is delivered at a rate ranging from of about 1 mL/min to about 10 mL/min. In another embodiment, the pharmaceutical formulation is delivered at a rate ranging from of about 1 mL/min to about 2 mL/min.

In one embodiment, the pharmaceutical formulation is delivered at a rate of about 0.1 mL/min, about 0.2 mL/min, about 0.3 mL/min, about 0.4 mL/min, about 0.5 mL/min, about 0.6 mL/min, about 0.7 mL/min, about 0.8 mL/min, about 0.9 mL/min, or about 1.0 mL/min.

In one embodiment, the pharmaceutical formulation is delivered at a rate of about 0.01 mL/min, about 0.02 mL/min, about 0.03 mL/min, about 0.04 mL/min, about 0.05 mL/min, about 0.06 mL/min, about 0.07 mL/min, about 0.08 mL/min, about 0.09 mL/min, or about 0.1 mL/min.

In one embodiment, the pharmaceutical formulation, comprising a AAV5.hFXN vector concentration of $1\times10^{12}$ vg/mL, is delivered to at a dose volume of about 1 mL per target site at a rate of about 0.001 mL/min.

The physician of ordinary skill in the art will be able to adjust the dose either higher or lower and determine an appropriate dose/dose regimen depending upon factors such as route of administration (e.g., a systemic dose may be as much as a 2-3 log increase), timing of doses, symptom improvement (i.e., efficacy), or the individual needs of the particular patient.

Outcome Measures:

Reference is made to M. Patel et al., "Progression of Friedreich ataxia: quantitative characterization over 5 years," Annals of Clinical and Translational Neurology, 2016; 3(9): 684-69; D. Lynch et al. "Friedreich ataxia: effects of genetic understanding on clinical evaluation and therapy" Arch. Neurol, 2002, 59:743-747; C. Wilson et al., "Quality of life in Friedreich ataxia: what clinical, social and demographic factors are important?" Eur. J Neurol. 200714 (9): 1040-1047; G. Rance et al., "Speech perception ability in individuals with Friedreich ataxia." Brain. 2008131: 2002-2012; A. Koeppen, "Friedreich's ataxia: Pathology, pathogenesis, and molecular genetics." J. Neurol. Sci. 2011, 303(1-2): 1-12; and S. R. Regner et al. "Friedreich ataxia clinical outcome measures: natural history evaluation in 410 participants" J. Child Neurol. 2012, 27(9):1152-8.

Efficacy data is collected at 1, 3, 6 and 12 months post study drug administration. Efficacy is evaluated in subjects using diffusion tensor imaging and various functional outcomes (including but not limited to FARS total and FARS Neuro; evaluation of a 25-foot walk test; evaluation on a GAITRite Walkway System; evaluation using a Biodex Balance System SD; evaluation using the 9-hole peg test). Diffusion tensor imaging may be measured, for example, by T2 relaxometry of dentate nucleus and DRG and/or NAA levels and iron levels by Magnetic Resonance Imaging (MRS).

Pharmaceutical excipients for in vivo use, the active ingredients (e.g., vectors expressing frataxin, virions, viruses, rAAVs, etc.) described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the active ingredient. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intraparenchymal, intramuscular, intravenous, intratumoral, intradermal, intrathecal intraventricular, and epidural), intravitreal, and by naso-gastric tube. In certain embodiments, the route of administration is to the CSF space; the subarachnoid space, (e.g., the cisterna magna); the brain, (e.g., the cerebroventricular space, the cerebellum, the cerebrum, the hippocampus, the interior cortex, the dorsal root ganglion, or caudate nucleus); or the spine (e.g., the lumbar spine, thoracic spine, cervical spine). In some embodiments, the active ingredient (e.g., vectors expressing frataxin, virions, viruses, rAAVs, etc.) is delivered in two injections: one in the right cerebellum and one in the left cerebellum. In some embodiments, these are two equal injections. In some embodiments, the active ingredient (e.g., vectors expressing frataxin, virions, viruses, rAAVs, etc.) are administered by injecting the cerebellum and also providing it systemically. It will be understood by those skilled in the art that the route of administration will depend upon the condition being treated and may vary with factors such as the condition of the recipient.

The polynucleotides of the invention for expressing frataxin (e.g., virons, AAVs, vectors, viruses, etc.) may be used to treat Friedreich's Ataxia. Administration of the polynucleotides, virions and/or compositions of the invention to a subject in need thereof ameliorates at least one symptom of Friedreich's ataxia. The symptoms of Friedreich's ataxia that can be ameliorated include, but are not limited to loss of coordination in the arms and/or legs, fatigue, vision impairment, hearing loss, slurred speech, aggressive scoliosis, diabetes mellitus, hypertrophic cardiomyopathy and cardiac arrhythmia.

Treatment of Friedreich's Ataxia using the constructs and compositions of the invention allow expression of frataxin in a subject at a level of at least 25% of normal expression of frataxin or greater up to normal levels (including levels that exceed normal levels, provided it causes no untoward effects). In some embodiments, the level will be at least 30% of normal. In other embodiments, the level will be at least, or greater than 35%, 40%, 45%, 50%, 55%, 60%, 65%, 70%, 75%, 80%, 85%, 90%, 95%, or 98%, of normal levels of frataxin. In other embodiments, normal levels of frataxin are achieved.

Using the compositions and methods of the invention, frataxin is expressed in the mitochondria. Preferably, frataxin is expressed in the mitochondria of at least one tissue selected from the group consisting of the cerebellum, the hippocampus, the anterior cortex, and the dorsal root ganglion.

Gene Switch Systems

The gene switch may be any gene switch that regulates gene expression by addition or removal of a specific ligand. In one embodiment, the gene switch is one in which the level of gene expression is dependent on the level of ligand that is present. Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.). In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595.

In one embodiment, the gene switch comprises a single transcription factor sequence encoding a ligand-dependent transcription factor complex under the control of a therapeutic switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

A. Ecdysone-Based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

```
Protein Sequence of the ecdysone receptor of Drosophila melanogaster
                          (SEQ ID NO: 10)

1 MKRRWSNNGG FMRLPEESSS EVTSSSNGLV LPSGVNMSPS SLDSHDYCDQ DLWLCGNESG

61 SFGGSNGHGL SQQQQSVITL AMHGCSSTLP AQTTIIPING NANGNGGSTN GQYVPGATNL

121 GALANGMLNG GFNGMQQQIQ NGHGLINSTT PSTPTTPLHL QQNLGGAGGG GIGGMGILHH

181 ANGTPNGLIG VVGGGGGVGL GVGGGGVGGL GMQHTPRSDS VNSISSGRDD LSPSSSLNGY
```

-continued

Protein Sequence of the ecdysone receptor of Drosophila melanogaster
(SEQ ID NO: 10)

```
241 SANESCDAKK SKKGPAPRVQ EELCLVCGDR ASGYHYNALT CEGCKGFERR SVTKSAVYCC

301 KFGRACEMDM YMRRKCQECR LKKCLAVGMR PECVVPENQC AMKRREKKAQ KEKDKMTTSP

361 SSQHGGNGSL ASGGGQDFVK KEILDLMTCE PPQHATIPLL PDEILAKCQA RNIPSLTYNQ

421 LAVIYKLIWY QDGYEQPSEE DLRRIMSQPD ENESQTDVSF RHITEITILT VQLIVEFAKG

481 LPAFTKIPQE DQITLLKACS SEVMMLRMAR RYDHSSDSIF FANNRSYTRD SYKMAGMADN

541 IEDLLHFCRQ MFSMKVDNVE YALLTAIVIF SDRPGLEKAQ LVEAIQSYYI DTLRIYILNR

601 HCGDSMSLVF YAKLLSILTE LRTLGNQNAE MCFSLKLKNR KLPKFLEEIW DVHAIPPSVQ

661 SHLQITQEEN ERLERAERMR ASVGGAITAG IDCDSASTSA AAAAQHQPCQ PQPQPQPSSL

721 TQNDSQHQTQ PQLQPQLPPQ LQGQLQPQLQ PQLQTQLQPQ IQPQPQLLPV SAPVPASVTA

781 PGSLSAVSTS SEYMGGSAAI GPITPATTSS ITAAVTASST TSAVPMGNGV GVGVGVGGNV

841 SMYANAQTAM ALMGVALHSH QEQLIGGVAV KSEHSTTA
```

In one embodiment, the ecdysone receptor ligand binding domain is selected from the group consisting of an invertebrate ecdysone receptor ligand binding domain, an Arthropod ecdysone receptor ligand binding domain, a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm Choristoneura fumiferana EcR ecdysone receptor ligand binding domain, a beetle Tenebrio molitor ecdysone receptor ligand binding domain, a Manduca sexta ecdysone receptor ligand binding domain, a Heliothis virescens ecdysone receptor ligand binding domain, a midge Chironomus tentans ecdysone receptor ligand binding domain, a silk moth Bombyx mori ecdysone receptor ligand binding domain, a squinting bush brown Bicyclus anynana ecdysone receptor ligand binding domain, a buckeye Junonia coenia ecdysone receptor ligand binding domain, a fruit fly Drosophila melanogaster ecdysone receptor ligand binding domain, a mosquito Aedes aegypti ecdysone receptor ligand binding domain, a blowfly Lucilia capitata ecdysone receptor ligand binding domain, a blowfly Lucilia cuprina ecdysone receptor ligand binding domain, a blowfly Calliphora vicinia ecdysone receptor ligand binding domain, a Mediterranean fruit fly Ceratitis capitata ecdysone receptor ligand binding domain, a locust Locusta migratoria ecdysone receptor ligand binding domain, an aphid Myzus persicae ecdysone receptor ligand binding domain, a fiddler crab Celuca pugilator ecdysone receptor ligand binding domain, an ixodid tick Amblyomma americanum ecdysone receptor ligand binding domain, a whitefly Bamecia argenlifoli ecdysone receptor ligand binding domain and a leafhopper Nephotelix cincticeps ecdysone receptor ligand binding domain.

In another embodiment, the ecdysone receptor ligand binding domain is the Choristoneura fumiferana ecdysone receptor ligand binding domain, for which the amino acid sequence is set forth in SEQ ID NO: 11.

In another embodiment, the ecdysone receptor ligand binding domain is an analog of the Choristoneura fumiferana ecdysone receptor ligand binding domain that retains at least 80%, 85%, 90%, 95%, 96%, 97%, 98% 99% or 100% of the in vitro Choristoneura fumiferana ecdysone receptor ligand binding activity of the Choristoneura fumiferana ecdysone receptor ligand binding domain. In vitro ecdysone receptor ligand binding assays are well known to those of ordinary skill in the art. For example, see WO 02/066612.

In another embodiment, the ecdysone receptor ligand binding domain analog is an ecdysone receptor ligand binding domain disclosed in WO 02/066612, US 2006/0100416, WO 05/108617 and 2005/0266457. In another embodiment, the ecdysone receptor ligand binding domain analog is the V1071/Y127E substitution mutant of the Choristoneura fumiferana ecdysone receptor which is set forth in SEQ ID NO: 12.

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises an AD, a DBD that recognizes a response element associated with the therapeutic protein or therapeutic polynucleotide whose expression is to be modulated; and a Group H nuclear receptor LBD. In certain embodiments, the Group H nuclear receptor LBD comprises a substitution mutation.

The DNA binding domain can be any DNA binding domain (DBD) with a known response element, including synthetic and chimeric DNA binding domains, or analogs, combinations, or modifications thereof. In one embodiment, the DNA binding domain is selected from the group consisting of a GAL4 DBD, a LexA DBD, a transcription factor DBD, a Group H nuclear receptor member DBD, a steroid/thyroid hormone nuclear receptor superfamily member DBD, a bacterial LacZ DBD, an EcR DBD, a GAL4 DBD and a LexA DBD.

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), or an analog, combination, or modification thereof.

Figure 2A:
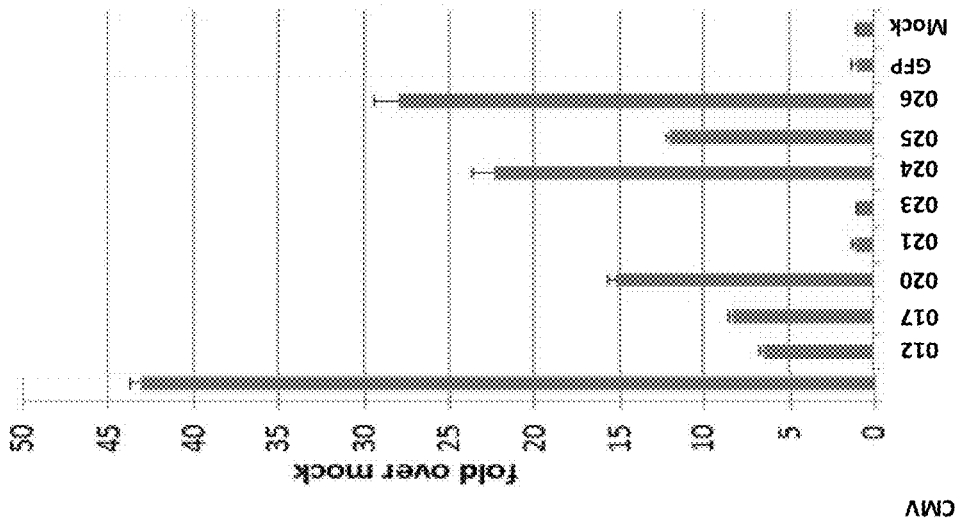
FIGS. 2A-2B show the Tier 1 results for selected constructs employing the UBC promoter in FA patient fibroblasts, along with the Green Fluorescent Protein (GFP), CMV and Mock controls.
Figure 2B:
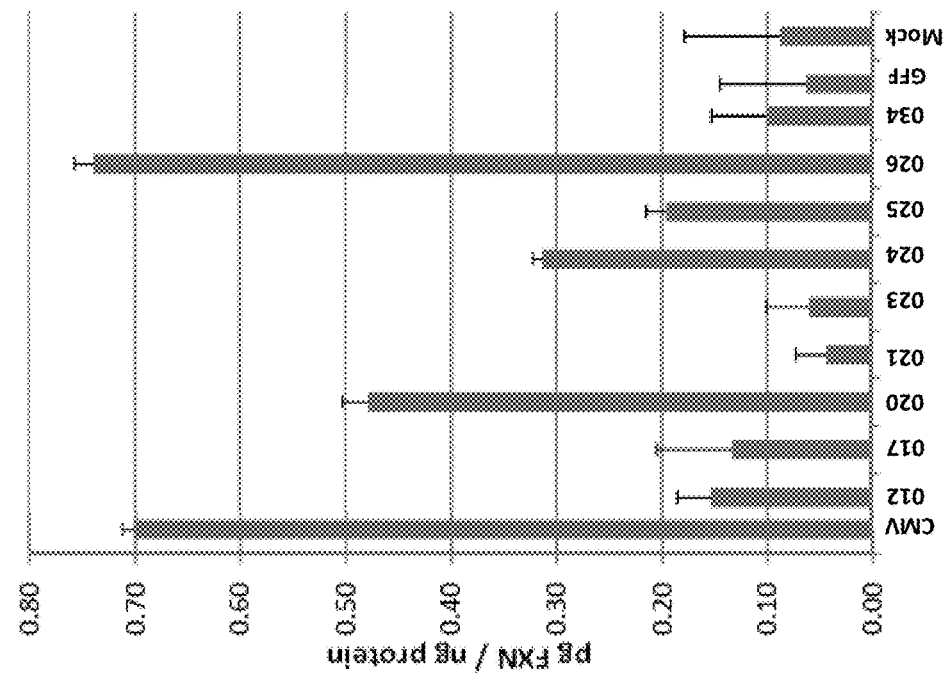

In another embodiment, the gene switch comprises a first transcription factor sequence, e.g., a CAP, under the control of a first therapeutic switch promoter (TSP-1) and a second transcription factor sequence, e.g., a LTF, under the control of a second therapeutic switch promoter (TSP-2), wherein the proteins encoded by said first transcription factor sequence and said second transcription factor sequence interact to form a protein complex (LDTFC), i.e., a "dual switch"- or "two-hybrid"-based gene switch. The first and second TSPs may be the same or different. In this embodiment, the presence of two different TSPs in the gene switch that are required for therapeutic molecule expression enhances the specificity of the therapeutic method (see FIG. 2 of WO 2011/119773). FIG. 2 of WO 2011/119773 also demonstrates the ability to modify the therapeutic gene switch to treat any disease, disorder, or condition simply by inserting the appropriate TSPs.

Figure 1B:
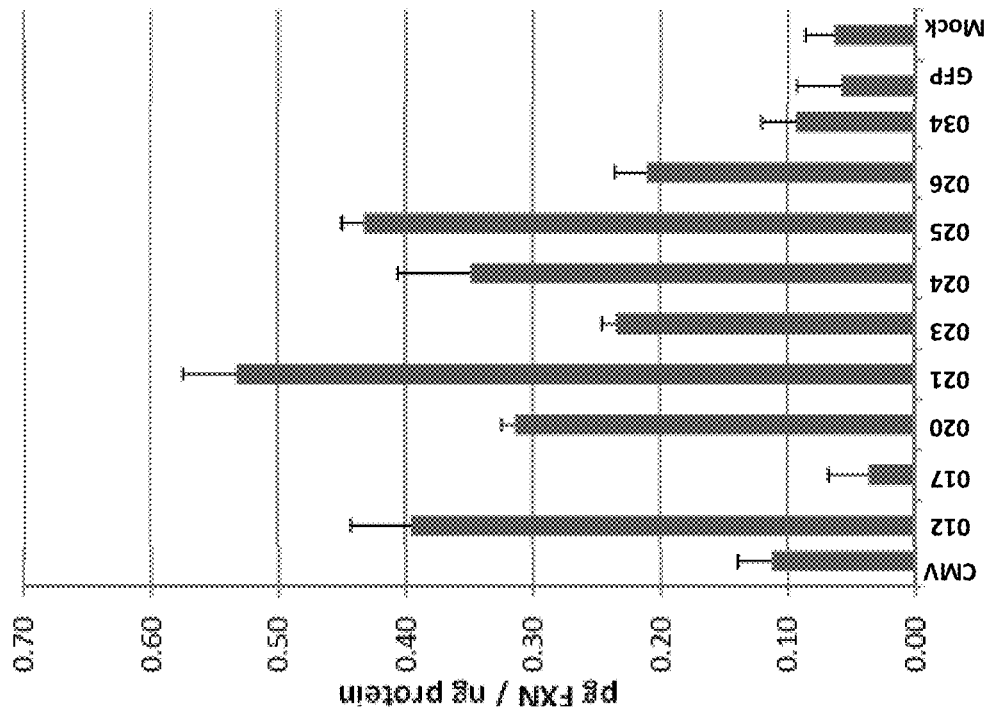

In a further embodiment, both the first and the second transcription factor sequence, e.g., a CAP or a LTF, are under the control of a single therapeutic switch promoter (e.g. TSP-1 in FIG. 1 of WO 2011/119773). Activation of this promoter will generate both CAP and LTF with a single open reading frame. This can be achieved with the use of a transcriptional linker such as an IRES (internal ribosomal entry site). In this embodiment, both portions of the ligand-dependent transcription factor complex are synthesized upon activation of TSP-1. TSP-1 can be a constitutive promoter or only activated under conditions associated with the disease, disorder, or condition.

Figure 4B:
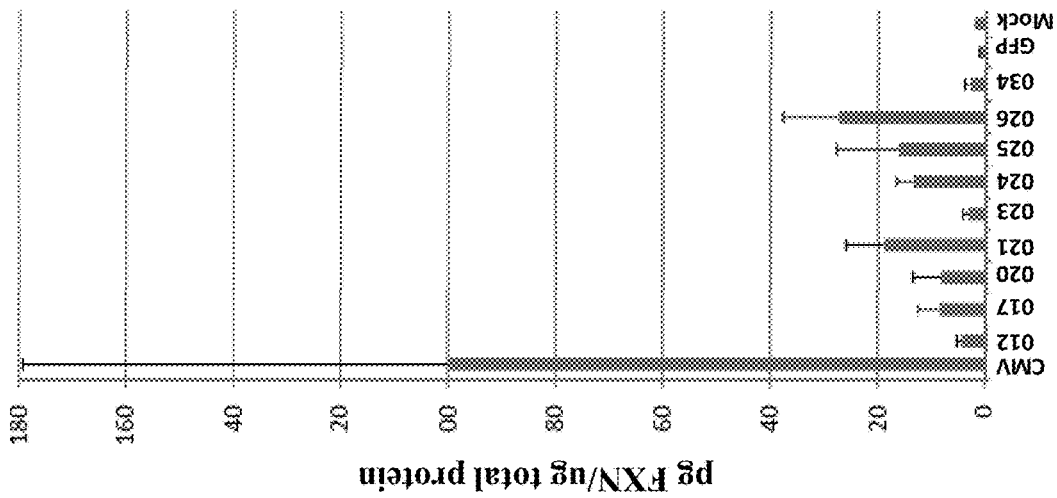
FIGS. 4A-4B show the Tier 2 results for selected constructs employing the UBC promoter in FA patient fibroblasts, along with the Green Fluorescent Protein (GFP), CMV and Mock controls.
Figure 4A:
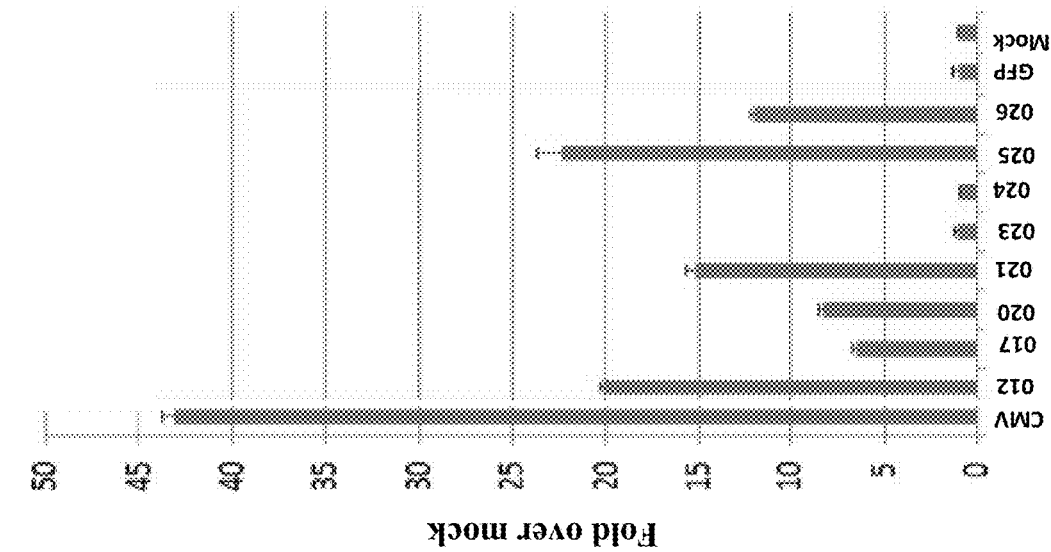

In a further embodiment, one transcription factor sequence, e.g. a LTF, is under the control of a therapeutic switch promoter only activated under conditions associated with the disease, disorder, or condition (e.g., TSP-2 or TSP-3 in FIG. 4 in WO 2011/119773) and the other transcription factor sequence, e.g., CAP, is under the control of a constitutive therapeutic switch promoter (e.g., TSP-1 in FIG. 4 in WO 2011/119773). In this embodiment, one portion of the ligand-dependent transcription factor complex is constitutively present while the second portion will only be synthesized under conditions associated with the disease, disorder, or condition.

In another embodiment, one transcription factor sequence, e.g., CAP, is under the control of a first TSP (e.g., TSP-1 in FIG. 3 in WO 2011/119773) and two or more different second transcription factor sequences, e.g., LTF-1 and LTF-2 are under the control of different TSPs (e.g., TSP-2 and TSP-3 in FIG. 3 in WO 2011/119773). In this embodiment, each of the LTFs may have a different DBD that recognizes a different factor-regulated promoter sequence (e.g., DBD-A binds to a response element associated with factor-regulated promoter-1 (FRP-1) and DBD-B binds to a response element associated with factor-regulated promoter-2 (FRP-2). Each of the factor-regulated promoters may be operably linked to a different therapeutic gene. In this manner, multiple treatments may be provided simultaneously.

In one embodiment, the first transcription factor sequence encodes a polypeptide comprising an AD, a DBD that recognizes a response element associated with the therapeutic product sequence whose expression is to be modulated; and a Group H nuclear receptor LBD, and the second transcription factor sequence encodes a transcription factor comprising a nuclear receptor LBD selected from a vertebrate retinoid X receptor (RXR), an invertebrate RXR, an ultraspiracle protein (USP), or a chimeric nuclear receptor comprising at least two different nuclear receptor ligand binding domain polypeptide fragments selected from a vertebrate RXR, an invertebrate RXR, and a USP (see WO 01/70816 A2 and US 2004/0096942 A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the therapeutic product sequence whose expression is to be modulated, and a second transcription factor sequence encoding a second polypeptide comprising an AD and a nuclear receptor LBD, wherein one of the nuclear receptor LBDs is a Group H nuclear receptor LBD. In one embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimerization partner and an AD (a "CAP") and the second transcription factor sequence encodes a protein comprising a DBD and a LBD (a "LTF").

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, or a USP (see WO 01/70816 A2, International Patent Application No. PCT/US02/05235, US 2004/0096942 A1 and U.S. Pat. No. 7,531,326, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat Rattus *norvegicus*, chicken Gallus *gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, or a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment. Such chimeric RXR LBDs are disclosed, for example, in WO 2002/066614.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element of a FRP associated with a therapeutic product sequence, provides external temporal regulation of expression of the therapeutic product sequence. The binding mechanism or the order in which the various components of this invention bind to each other, that is, for example, ligand to LBD, DBD to response element, AD to promoter, etc., is not critical.

In a specific example, binding of the ligand to the LBD of a Group H nuclear receptor and its nuclear receptor LBD partner enables expression of the therapeutic product sequence. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors. Another advantage of two-hybrid systems is that they allow choice of a promoter used to drive the gene expression according to a desired end result. Such double control may be particularly important in areas of gene therapy, especially when cytotoxic proteins are produced, because both the timing of expression as well as the cells wherein expression occurs may be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The DNA binding domain of the first hybrid protein binds, in the presence or absence of a ligand, to the DNA sequence of a response element to initiate or suppress transcription of downstream gene(s) under the regulation of this response element.

The functional LDTFC, e.g., an EcR complex, may also include additional protein(s) such as immunophilins. Additional members of the nuclear receptor family of proteins, known as transcriptional factors (such as DHR38 or betaFlZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al., Mol Endocrinol. 10:1167 (1996)). These cofactors may either be endogenous within the cell or organism, or may be added exogenously as transgenes to be expressed in either a regulated or unregulated fashion.

B. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises:

(a) a first polynucleotide encoding a first chimeric protein which binds to rapamycin or an analog thereof and which comprises at least one FKSO6-binding protein (FKBP) domain and at least one protein domain heterologous thereto, wherein the FKBP domain comprises a peptide sequence selected from:

(1) a naturally occurring FKBP (2) a variant of a naturally occurring FKBP in which up to 10 amino acid residues have been deleted, inserted, or replaced with substitute amino acids, and (3) an FKBP encoded by a DNA sequence which selectively hybridizes to a DNA sequence encoding an FKBP of (1) or (2);

(b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:

(4) a naturally occurring FRB domain, (5) a variant of a naturally occurring FRB domain in which up to 10 amino acid residues have been deleted, inserted, or replaced with substitute amino acids, and (6) an FRB domain encoded by a DNA sequence which selectively hybridizes to a DNA sequence encoding an FRB of (4) or (5).

In this gene switch system, each of the first polynucleotide and the second polynucleotide are under the control of one or more therapeutic switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757; 6,649,595; 6,509,152; 6,479,653; and 6,117,680.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

C. Prokaryotic Repressor/Operator based Gene Switch System

In one embodiment, the present invention provides gene switch system comprising (a) a first polynucleotide coding for a transactivator fusion protein comprising a prokaryotic tetracycline ("tet") repressor and a eukaryotic transcriptional activator protein domain; and (b) a second polynucleotide coding for a frataxin polypeptide, wherein said second polynucleotide is operably linked to a minimal promoter and at least one tet operator sequence. The first polynucleotide coding for a transactivator fusion protein may comprise therapeutic switch promoter as described elsewhere herein.

In another embodiment, the gene switch system comprises the lactose ("Lac") repressor-operator systems from the bacterium Escherichia coli. The gene switch system of the present invention may also comprise (a) a first polynucleotide coding for a transactivator fusion protein comprising a prokaryotic tetracycline ("tet") repressor and a eukaryotic transcriptional activator protein domain; and (b) a second polynucleotide coding for a frataxin polypeptide, wherein said second polynucleotide is operably linked to a gene switch promoter. In the Lac system, a lac operon is inactivated in the absence of lactose, or synthetic analogs such as isopropyl-b-D-thiogalactoside.

Additional gene switch systems include those described in the following: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. Nos. 7,304,162; 7,304,161; MX234742; KR10-0563143; AU765306; AU2002-248500; and AU2002-306550.

D. Combination of the Gene Switch Systems

The present invention provides nucleic acid compositions, modified cells, and bioreactors comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more interleukin polypeptides, upon binding to one or more ligands. Within the scope of the present invention are any numbers of and/or combinations of gene switch systems.

In one embodiment, the present invention provides a nucleic acid composition comprising a gene switch system which comprises:
  i. a first gene expression cassette comprising a polynucleotide encoding a first hybrid polypeptide which comprises:
    1. a transactivation domain, which activates a promoter operably associated with a polynucleotide encoding a frataxin polypeptide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a frataxin polypeptide; and
    2. a ligand binding domain; and
  iii. a third gene expression cassette comprising a polynucleotide encoding a frataxin polypeptide, said third gene expression cassette comprising:
    1. an inducible promoter, which is activated by the transactivation domain of the second hybrid polypeptide; and,
    2. a polynucleotide encoding said frataxin polypeptide.

In certain embodiments, the combination of two or more gene switch systems may be (1) a dual-switch ecdysone receptor based gene expression system and (2) a single-switch ecdysone receptor based gene switch. In other embodiments, the combination may be (1) a single- or dual-switch ecdysone receptor based gene switch and (2) a rapamycin based gene switch. Alternatively, the combination of gene switch systems may be two identical rapamycin based gene switch systems disclosed above. Any possible combinations of the gene switch systems are within the scope of the invention. Examples of dual-switch ecdysone systems can be found, for example, in WO 2002/29075 and US 2002/0110861.

E. Other Gene Switches

In another aspect of the invention, gene expression cassettes of the invention incorporate a cumate switch system, which works through the CymR repressor that binds the cumate operator sequences with high affinity. (SparQ™ Cumate Switch, System Biosciences, Inc.). The repression is alleviated through the addition of cumate, a non-toxic small molecule that binds to CymR. This system has a dynamic inducibility, can be finely tuned and is reversible and inducible.

In another aspect of the invention, gene expression cassettes of the invention incorporate a riboswitch, which is a regulatory segment of a messenger RNA molecule that binds an effector, resulting in a change in production of the proteins encoded by the mRNA. An mRNA that contains a riboswitch is directly involved in regulating its own activity in response to the concentrations of its effector molecule. Effectors can be metabolites derived from purine/pyrimidine, amino acid, vitamin, or other small molecule co-factors. These effectors act as ligands for the riboswitch sensor, or aptamer. Breaker, R R. Mol Cell. (2011) 43(6): 867-79.

In another aspect of the invention, gene expression cassettes of the invention incorporate the biotin-based gene switch system, in which the bacterial repressor protein TetR is fused to streptavidin, which interacts with the synthetic biotinylation signal AVITAG that is fused to VP16 to activate gene expression. Biotinylation of the AVITAG peptide is regulated by a bacterial biotin ligase BirA, thus enabling ligand responsiveness. Weber et al. (2007) *Proc. Natl. Acad. Sci. USA* 104, 2643-2648; Weber et al. (2009) Metabolic Engineering, 11(2):117-124.

Additional gene switch systems which may be used as part of the present invention are well known in the art, including but not limited to those described in Auslander and Fussenegger, *Trends in Biotechnology* (2012), 31(3):155-168, incorporated herein by reference.

Gene Switch Ligands

As used herein, the term "ligand," as applied to gene switches (e.g., EcR based gene switches), describes small and soluble molecules having the capability of activating a gene switch to stimulate expression of a polypeptide encoded therein. The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroyl-hydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxy-cholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, published as US 2009/0163592, and PCT Appl. No. PCT/US2008/006757, both of which are incorporated herein by reference in their entireties.

For example, a ligand for the ecdysone receptor based gene switch may be selected from any suitable ligands. Both naturally occurring ecdysone or ecdysone analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 B1, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethyl-benzoyl)-N'-(3,5-dimethylbenzoyl)-N-tert-butyl-hydrazine) as ligands for an ecdysone-based gene switch. Also included in the present invention as a ligand are other dibenzoylhydrazines, such as those disclosed in U.S. Pat. No. 5,117,057 B1. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkyl-N'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I

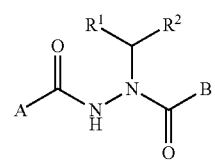

Formula I wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

or pharmaceutically acceptable salts, hydrates, crystalline forms or amorphous forms thereof.

In another embodiment, the ligand may be enantiomerically enriched compounds of Formula II

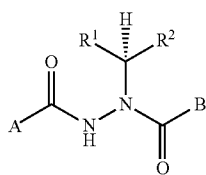

Formula II wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S;

or pharmaceutically acceptable salts, hydrates, crystalline forms or amorphous forms thereof.

In certain embodiments, the ligand may be enantiomerically enriched compounds of Formula III

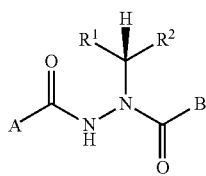

Formula III wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$, wherein the absolute configuration at the asymmetric carbon atom bearing $R^1$ and $R^2$ is predominantly R;

or pharmaceutically acceptable salts, hydrates, crystalline forms or amorphous forms thereof.

In one embodiment, a ligand may be (R)-3,5-dimethylbenzoic acid N-(1-tert-butyl-butyl)-N'-(2-ethyl-3-methoxybenzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a frataxin polypeptide of the present invention. See U.S. application Ser. No. 12/155,111, published as US 2009/0163592, filed May 29, 2008, which is fully incorporated by reference herein.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. No. 6,649,595 B2 and U.S. Pat. No. 6,187,757. See also U.S. Pat. Nos. 7,276,498 and 7,273,874.

The ligands described herein may be administered alone or as part of a pharmaceutical composition comprising a pharmaceutically acceptable carrier. In one embodiment, the pharmaceutical compositions are in the form of solutions, suspensions, tablets, capsules, ointments, elixirs, or injectable compositions.

Certain embodiments of the invention will now be described with reference to particular examples which are provided solely to illustrate the invention and should not be construed to be limiting in any way.

EXAMPLES

Certain aspects of the invention will now be described, but shall not be construed as limiting of the invention.

Materials and Methods Used in the Examples

A. Matrix Design and Design of Experiments

The initial Frataxin design cycle was carried out in three phases. First, parts were selected based on historical data and expert consideration and literature precedence for in vivo target cell type (DRGs). Second, the full factorial matrix was formulated. Third, D-optimal experimental design was carried out on the full factorial. This resulted in a subset of the matrix that uncovers the maximal variance and leads most rapidly to the development of a predictive model.

A constitutive expression matrix of ~80 constructs, with variations in the promoter and 5'/3' regulatory elements was designed and analyzed using Design of Experiment algorithms to reduce the number of constructs needed to adequately test for "high" and "medium" levels of FXN expression (potentially representing super-physiological and physiological levels, respectively). The FXN minimal essential 1,255 bp promoter as described in Greene et al. (2005) was included in the matrix to provide potentially physiological levels of FXN expression. Other constitutive promoters included EF1a, UBC, and PGK1. Fifty constructs were generated from the original matrix of 80.

The matrix was reduced to 50 vectors with additional positive, super-physiological expression controls included in the expression screen: CAG-FXN-hGHpA and CMV-5U2-FXN-hGHpA. The CMV promoter, known to be a very strong promoter, was not included in the matrix as it is known to be silenced over time in vivo (McCown et al. (1996) *Brain Res.* 713:99-107; Klein et al. (1998) *Exp. Neurol.* 150:183-194; Paterna et al. (2000) *Gene Ther.* 7, 1304-1311; Tenenbaum et al. (2004) *J. Gene Med.* 6(Suppl. 1), S212-S222). The CAG-FXN-hGHpA construct with the CAG (chicken beta-actin hybrid) promoter, also a strong promoter, was included as a comparator. The CAG promoter also contains the CMV early enhancer and the first exon and the first intron of chicken beta-actin gene, and the 5' splice acceptor of the rabbit beta-globin gene. This hybrid promoter and other variations of it, is routinely used in AAV gene therapy applications (e.g., Flotte et al. (2011) *Hum. Gene Ther.* 22:1239-1247; Maclachlan et al. (2011) *Mol. Ther.* 19:326-334; Perdomini et al. (2014) *Nature Med.* 20:542-547).

The 50 matrix vectors and controls were constructed using standard cloning techniques. The matrix vectors and controls were generated into an AAV backbone where the expression cassette was inserted between the two AAV inverted terminal repeat (ITR) sequences which are essential for packaging the genome into the selected AAV capsid serotype. Constructs also included non-coding "stuffer" sequences ranging from 1,001 bp to 2,500 bp to bring the genome size to the ~4.2 kb which is optimal for capsid packaging. Constructs were fully sequence verified using next generation sequencing technologies, including the Nextra XT DNA preparation kit from Illumina with some modifications. A subset of these is presented herein and is listed in Table 1.

B. Transfection Procedures, Assays, and Analysis

On day 0, frozen SY5Y cells (European Collection of Cell Cultures, ECACC operated by Public Health England), Sigma Cat #94030304; Lot #13C014) were seeded in an original flask and incubated at 37° C., 5% $CO_2$, saturating humidity. Separately, frozen FA fibroblasts (Coriell; Cat #GM03816) were seeded in an original flask and incubated at 37° C., at 5% $CO_2$, saturating humidity.

On day 3, when the SY5Y and fibroblasts were at 75% confluence, the media of each flask was aspirated, and the cells were rinsed once with 10 mL DPBS (Gibco, without Calcium, Magnesium, Cat #14190), prior to resuspending them in 3 mL Trypsin-EDTA (0.25%, Gibco Cat #25200) and incubating them for 3 minutes at RT. 5 mL of media was added to neutralize trypsin in each flask. Cells were collected from each of the T75 flasks into 15 mL Falcon tubes and centrifuged at 1000 rpm in a Sorval table-top centrifuge for 5 minutes at RT. The supernates were discarded and the cells were resuspended in 2 mL of fresh medium. The cells were agitated gently to break up any clumps. Cells were then split 1:2 and 1 mL of the cell suspensions were added to 4 T75 flasks each.

C. Transfection

On day 0, $4.0\times10^4$ live SY5Y and FA fibroblast cells were plated in 0.4 mL medium/well of four 48-well tissue-culture treated plates. Cells were collected by aspirating and discarding the media, rinsing each flask once with 10 mL DPBS, aspirating and discarding the DPBS, resuspending the cells in 3 mL Trypsin-EDTA and incubating them for 3 minutes at RT. 5 mL of media was then added to neutralize trypsin in each flask and the cells were collected into 15 mL Falcon tubes and centrifuged at 1000 rpm in a Sorval table-top centrifuge for 5 minutes at RT. The supernates were discarded and the cells were resuspended in 2 mL fresh fibroblast medium and the cells from each of the 2 cell types were pooled (fibroblasts separately from SY5Y). The cells were agitated gently to break up any clumps.

Cells were counted by adding 10 µL of cell suspension to 90 µL diluted trypan blue and mixed gently before loading cells on a hemacytometer to count the cells. We obtained Live/Dead: $6.5\times10^6$ cells/mL of SY5Y and $1.8\times10^6$ cells/mL of FA fibroblasts wherein viability: 83/85=97.6% for SY5Y and 82/85=96.5% for FA fibroblasts.

Then $4.0\times10^4$ SY5Y cells and FA fibroblasts were plated into each of the wells of the 48 well plates containing 0.4 mL of fresh DMEM/F12 medium (Gibco, Cat #11320-033, supplemented with 10%° heat inactivated fetal bovine serum (FBS)(Atlanta Bio, Cat #S11550H). The plates were rocked side to side and forward and backward to evenly distribute cells. The plates were incubated overnight at 37° C., at 5% $CO_2$, saturating humidity.

For FA fibroblasts, on Day 1, cells were observed for confluency and general appearance. DNA:TransfeX (1:1) complexes for FA fibroblasts were prepared. One tube for each plasmid was labeled and there were 3 tubes for each of the plasmids. The TransfeX, plasmid DNA, and Opti-MEM I Reduced-Serum Medium (Gibco, Cat #31985-062, with L-Glutamine, w/HEPES, w/2.4 g/L NaBicarb) were warmed to room temperature and swirled gently to mix. 50 µL of Opti-MEM I Reduced-Serum Medium was pipetted into sterile microcentrifuge tubes. Appropriate volumes of plasmid DNA (0.75 µg DNA) were added per tube and mixed thoroughly by gentle pipetting. Then, 0.75 µL of TransfeX Reagent (ATCC, Cat #ACS-4005) was added to the diluted DNA mixture in each of the tubes. The TransfeX:DNA complexes were mixed thoroughly by pipetting followed by flicking the tubes. The TransfeX:DNA complexes were incubated at room temperature for 15 minutes. The tubes were centrifuged (short spin) to force all liquid to bottom of Eppendorf tubes. To add the transfection complexes to the FA fibroblasts, the complexes were distributed to the cells by adding the complexes drop-wise to different areas of the wells (50 µL of mixture to each of three triplicate wells). The culture vessels were gently rocked back and forth and from side to side to evenly distribute the TransfeX:DNA complexes and incubated for ~72 hrs.

For the SY5Y cells, on Day 1, DNA:Fugene 6 (1:3) complexes were prepared. One tube for each plasmid was labeled and there were 3 tubes for each of the plasmids. The FuGene 6, plasmid DNA, and Opti-MEM I Reduced-Serum Medium were warmed to room temperature and swirled gently to mix. 50 µL of Opti-MEM I Reduced-Serum Medium was pipetted into sterile microcentrifuge tubes. Then 2.25 µL Fugene 6 Reagent (Promega, Cat #2692) was added to the media in each of the tubes and the incubated for 5 minutes. Appropriate volumes of plasmid DNA (0.75 µg DNA) were added per tube and mixed thoroughly by gentle pipetting. The transfection reagent/media/DNA complexes were mixed thoroughly by pipetting followed by flicking the tubes. The complexes were incubated at room temperature for 15 minutes. The tubes were centrifuged (short spin) to force all liquid to bottom of Eppendorf tubes. To add the transfection complexes to the SY5Y cells, the complexes were distributed to the cells by adding the complexes drop-wise to different areas of the wells (50 µL of mixture to each of three triplicate wells). The culture vessels were gently rocked back and forth and from side to side to evenly distribute the transfection complexes and incubated for ~72 hrs.

On Day 4, the GFP fluorescence signal was verified (visually) and cells were lysed in cell lysis buffer (for each 10 mL of cell lysis buffer: 200 µL (50× cell extraction enhancer)+2 mL (5× cell extraction buffer)+7.8 mL (DI water, Gibco, Cat #A12873)+1 tablet Protease inhibitor/EDTA (Roche, Cat #04693159001). Briefly, supernatants from each of the wells of the four 48 well plates was aspirated and the cells were washed twice with chilled 1×PBS (all steps of the procedure performed on ice). Chilled Lysis buffer was added at 150 L/well. The cells in each well were scraped to ensure cell lysis using the bottom of a P1000 tip. The plates with cells in lysis buffer were incubated at 4° C. on a shaker for 30 minutes. Cell lysates were collected by pipetting up and down without forming foam and add to a microfuge tube. The lysates were centrifuged at 4° C., 18,000 rpm for 20 min. The cell lysates were then transferred to a new microfuge tube and stored at −800 C until ready to use in the Frataxin ELISA (see below).

On Day 5, total protein concentrations of the SY5Y and the FA fibroblast cell lysates transfected with the F×N matrix was determined using the Micro BCA Assay Protocol (Pierce, Cat #23235; Lot #PK 207908) per manufacturer's instructions.

On Day 6, FXN contents in the F×N matrix transfected SY5Y and FA fibroblast samples was determined using the FXN ELISA (FRATAXIN Human Simple Step ELISA, Abcam ab176112) according to the manufacturer's recommendation with the exception that all the samples and Standards were diluted in 1×PBS. Briefly, reagents, working standards, and samples were prepared according to the Abcam Kit's manufacturer instructions. All materials and reagents were equilibrated to room temperature prior to use. All standards, controls and samples were run in duplicates.

A 50 µL aliquot of each sample or standards was added to appropriate wells. SY5Y cell lysates were diluted 1:150 and the FA Fibroblasts were diluted 1:50 based on the total protein concentration data obtained from the micro BCA assay (Pierce, Cat #23235; Lot #PK 207908) per the manufacturer's instructions. A50 µL aliquot of the Antibody Cocktail (1X Capture Antibody plus lX Detector Antibody provided in Frataxin ELISA kit and prepared per manufacturer's instructions) was to each well. The plate was sealed and incubated for 1 hour at room temperature on a plate shaker set to 400 rpm. Each well was washed with 3×350 µL 1× Wash Buffer PT (buffer provided in Frataxin ELISA kit and prepared per manufacturer's instructions) by aspirating or decanting from wells then dispensing 350 µL 1× Wash Buffer PT into each well. After the last wash, the plate was inverted and blotted against clean paper towels to remove excess liquid. 100 µL of TMB Substrate was added to each well and incubated for 10 minutes in the dark on a plate shaker set to 400 rpm. 100 µL of Stop Solution was then added to each well. The plate was shaken on a plate shaker for 1 minute to mix. OD at 450 nm of each well was recorded as an endpoint reading.

Plasmids: Construct description in Table 1. All constructs contain a stuffer ranging from 1001 to 3000 bp to ensure optimal genome packaging size for AAV.

TABLE 1

Selected Constructs

| No./ name | Composition* | | |
|---|---|---|---|
| | Promoter | 5' Reg | 3' Reg |
| CMV | CMV (SEQ ID NO: 13) | 5U2 (SEQ ID NO: 4) | hGHpA (SEQ ID NO: 5) |
| 012 | UBC (SEQ ID NO: 3) | FTH1-5'UTR (SEQ ID NO: 14) | SV40 early (SEQ ID NO: 8) |
| 017 | UBC (SEQ ID NO: 3) | FTH1-5'UTR (SEQ ID NO: 14) | SV40 late (SEQ ID NO: 9) |
| 020 | UBC (SEQ ID NO: 3) | GAPDH (SEQ ID NO: 15) | Other |
| 021 | UBC (SEQ ID NO: 3) | RPL6-5'Splice (SEQ ID NO: 16) | Other |
| 023 | UBC (SEQ ID NO: 3) | GAPDH (SEQ ID NO: 15) | synthetic 3' regulatory element (SEQ ID NO: 7) |
| 024 | UBC (SEQ ID NO: 3) | 5U2 (SEQ ID NO: 4) | synthetic 3' regulatory element (SEQ ID NO: 7) |
| 025 | UBC (SEQ ID NO: 3) | RPL6-5'Splice (SEQ ID NO: 16) | synthetic 3' regulatory element (SEQ ID NO: 7) |
| 026 | UBC (SEQ ID NO: 3) | 5U2 (SEQ ID NO: 4) | hGHpA (SEQ ID NO: 5) |
| 034 | PGK1 (SEQ ID NO: 17) | GAPDH (SEQ ID NO: 15) | SV40 late (SEQ ID NO: 9) |

TABLE 1-continued

Selected Constructs

| No./ name | Composition* | | |
|---|---|---|---|
| | Promoter | 5' Reg | 3' Reg |
| GFP | CMV (SEQ ID NO: 13) | n/a | unknown |
| Mock | | | |

D. AAV5 Vector Manufacture

Viral particles, including but not limited to, viruses, vectors, virions, gene delivery vehicles, rAAVs, capsids and empty capsids, useful in the practice of the present invention, can be constructed using methods well known in the art of molecular biology. Viral vectors carrying transgenes can be assembled from polynucleotides encoding the transgene, suitable regulatory elements and elements necessary for production of viral proteins that mediate cell transduction.

The Biological Substance, AAV5.hFXN is a recombinant adeno-associated virus (rAAV) containing WT hFXN cDNA. The gene insert (e.g. 'transgene') codes for human frataxin protein precursor, the expression of which is intended to increase the amount of the mitochondrial frataxin in the treated subjects. The hFXN cDNA in the vector was chemically synthesized de novo to match the sequence of normal human frataxin mRNA described in Reference Sequence: NM_000144.4 (on the worldwide web at URL ncbi.nlm.nih.gov/nuccore/NM_000144).

Figure 21:
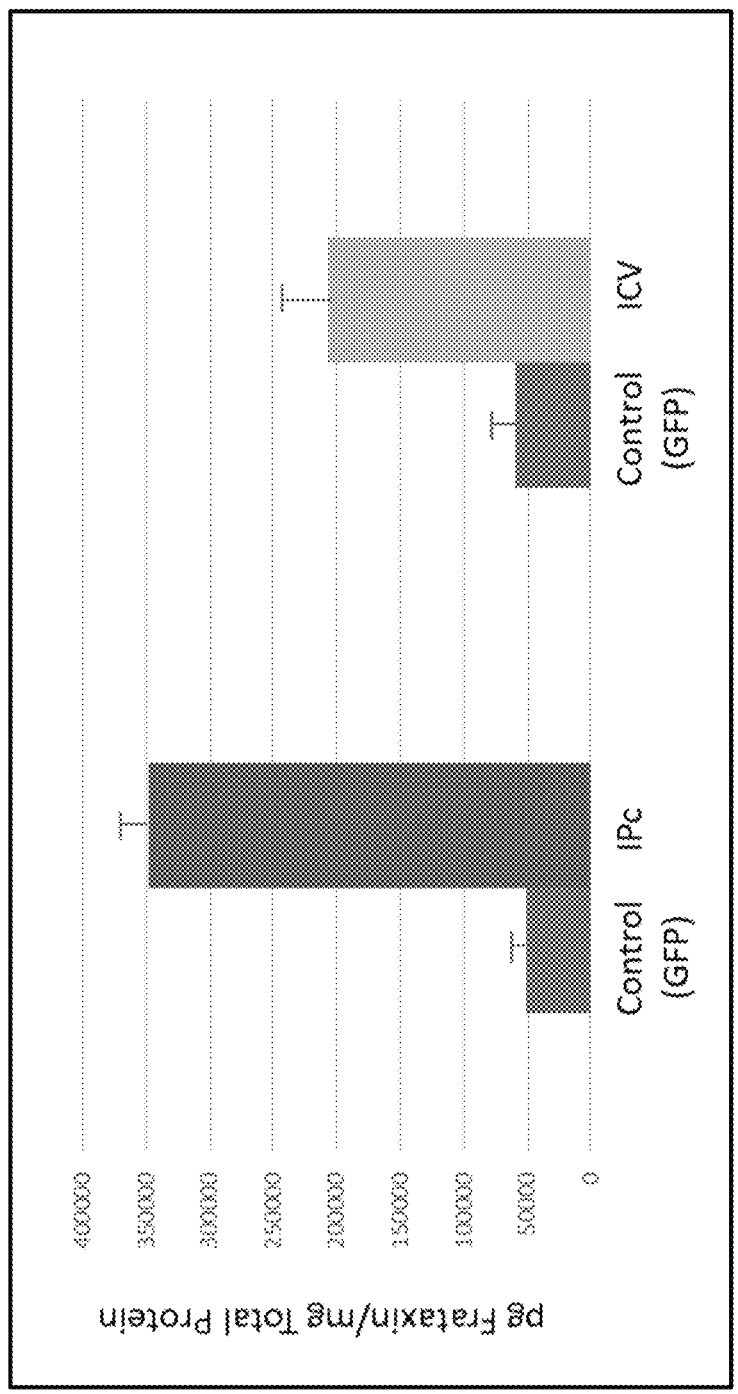
FIG. 21 shows a chart representing rAAV5-hFXN vector-Induced Expression of Human Frataxin in the Cerebellum of Sarsero Frataxin-Deficient Mice. rAAV5.hFXN (2 µL) was injected directly into the cerebellum (IPc, N=7 mice) or intracerebroventricular space (ICV, N=7) of FA mice at a dose of $7 \times 10^9$ vg/µL. Three FA mice were injected with AAV5.GFP (control, 2 µL) either in the cerebellum or ICV at a dose of $4 \times 10^9$ vg/µL. At 4 weeks post injection, the cerebellums were harvested. Cerebellar tissue from two untreated control mice was also harvested. Tissue lysates were analyzed for human frataxin as described above. The average expression for each treatment is shown.

Description of 026 construct: The major elements of the recombinant AAV5 single-stranded DNA vector are shown in FIG. 21. The vector elements are described in more detail in Table 3.

TABLE 3

Description of the Single-stranded DNA Vector Elements.

| Nucleotide Bases | Element Identifier | Description |
|---|---|---|
| 1-141 | ITR | AAV2 inverted terminal repeat |
| 142-191 | not shown | Restriction enzyme sites |
| 192-762 | UBC promoter | Human Ubiquitin C (UBC) promoter |
| 763-784 | not shown | Restriction enzyme sites |
| 785-964 | 5U2 | Synthetic 5' regulatory element |
| 965-970 | not shown | Restriction enzyme site |
| 971-1609 | hFXN GOI | Human FXN cDNA |
| 1610-1635 | not shown | Restriction enzyme sites |
| 1636-2262 | hGH-Poly A | Human Growth Hormone Poly A |
| 2263-2283 | not shown | Restriction enzyme sites |
| 2284-4533 | ITR linker | Synthetic linker |
| 4534-4451 | not shown | Restriction enzyme site |
| 4452-4691 | ITR | AAV2 inverted terminal repeat |

A representative example of a rAAV5.hFXN plasmid nucleotide sequence (SEQ ID NO: 20) is shown in FIG. 20. Embodiments of the present invention include, but are not limited to functional homologues of the rAAV5.hFXN plasmid nucleotide sequence (SEQ ID NO:20).

A representative example of a vector containing a gene insert is a nucleotide sequence nucleotide sequence (SEQ ID NO:19) is shown in FIG. 19. The sequence represents the pAAV5.hFXN plasmid from the beginning of the left ITR to the end of the right ITR. Embodiments of the present invention include, but are not limited to functional homologues of the nucleotide sequence (SEQ ID NO: 19).

Pharmaceutical Formulation

The biologic product, rAAV5.hFXN vector is formulated in a sterile, buffered solution suitable for intrathecal injection. Exemplary compositions of are shown in Table 4 and Table 5.

TABLE 4

Example Composition of AA5.hFXN Vector Product

| Component | Concentration | Function |
|---|---|---|
| AAV5.hFXN | $5 \times 10^{13}$ vg/mL | Active ingredient |
| NaCl | 7.01 gm/L | Diluent of active vector that mimics the major chemical ionic species, concentrations, and pH (7.3) of human cerebral spinal fluid |
| KCl | 0.208 gm/L | |
| CaCl$_2$ | 0.233 gm/L | |
| MgCl$_2$ | 0.029 gm/L | |
| Na$_2$HPO$_4$ | 1.10 gm/L | |
| NaH$_2$PO$_4$ | 0.329 gm/L | |
| H$_2$O | qs 1.0 L | |

TABLE 5

Example Composition of AA5.hFXN Vector Product

| Component | Concentration | Function |
|---|---|---|
| AAV5.hFXN | $2.5 \times 10^{11}$ vg/mL | Active ingredient |
| NaCl | 0.154M | pH (7.4) |
| Na$_2$HPO$_4$ | 0.056M | |
| KH$_2$PO$_4$ | 0.0106M | |

TABLE 7

Example Composition of AA5.hFXN Vector Product

| Component | Concentration | Function |
|---|---|---|
| AAV5.hFXN | $5 \times 10^{13}$ vg/mL | Active ingredient |
| NaCl | 0.337M | pH (7.0) |
| KCl | 0.027M | |
| Na$_2$HPO$_4$ | 0.015M | |
| KH$_2$PO$_4$ | 0.0015M | |

Example 1

(A) Tier 1 Screen

Transfections occurred in 48 well plates in duplicate. For each construct, the cells from the two wells were pooled, assayed for total protein levels (BCA), and then assayed for FXN levels by ELISA. FXN levels were normalized to total protein content, and error bars represent ELISA assay duplicates. Shown in FIG. 1 and FIG. 2, respectively, are the FXN expression levels in undifferentiated SY5Y cells and FA patient fibroblasts with constructs employing the UBC promoter. Panel A of FIG. 1 and FIG. 2 shows pg FXN/ng total protein. Panel B of FIG. 1 and FIG. 2 shows the fold FXN over mock. With only minimal exception, the UBC (SEQ ID NO:3) and EF1a (SEQ ID NO:18) promoters provided higher levels of FXN expression in SY5Y and in FA patient fibroblasts (FIG. 2).

(B) Tier 2 Screen

Transfections were performed in 48 well plates in triplicate, with separate DNA/lipid prep for each well. Shown in FIG. 3 and FIG. 4 are results from the Tier 2 screen. FXN expression from UBC and EF a promoter constructs (plus two minimum FXN promoter constructs not included in the first screen) were evaluated and the results grouped by 5' regulatory elements.

(C) Tier 3 Screen

Figure 5A:
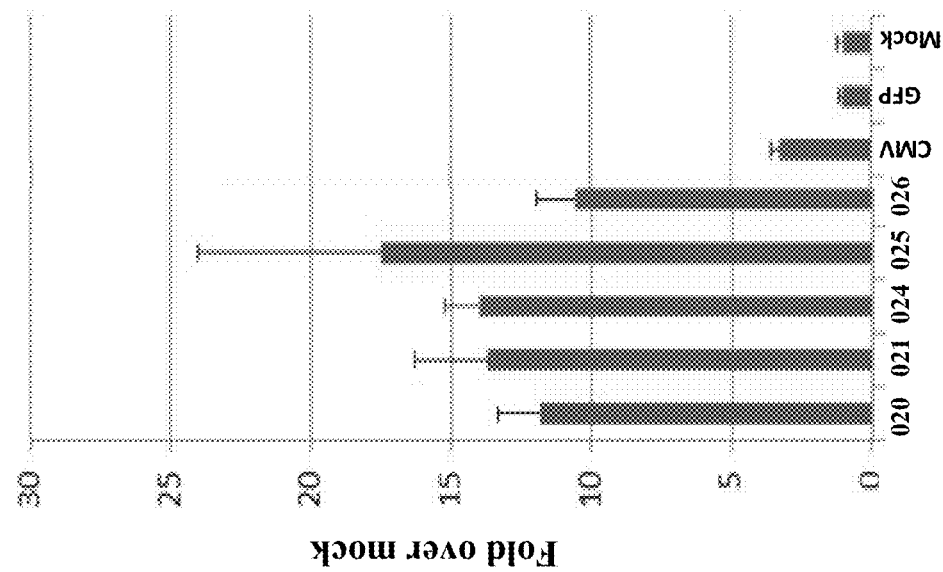
FIGS. 5A-5B show the Tier 3 results for selected constructs employing the UBC promoter in undifferentiated SY5Y, along with the Green Fluorescent Protein (GFP), CMV and Mock controls.
Figure 5B:
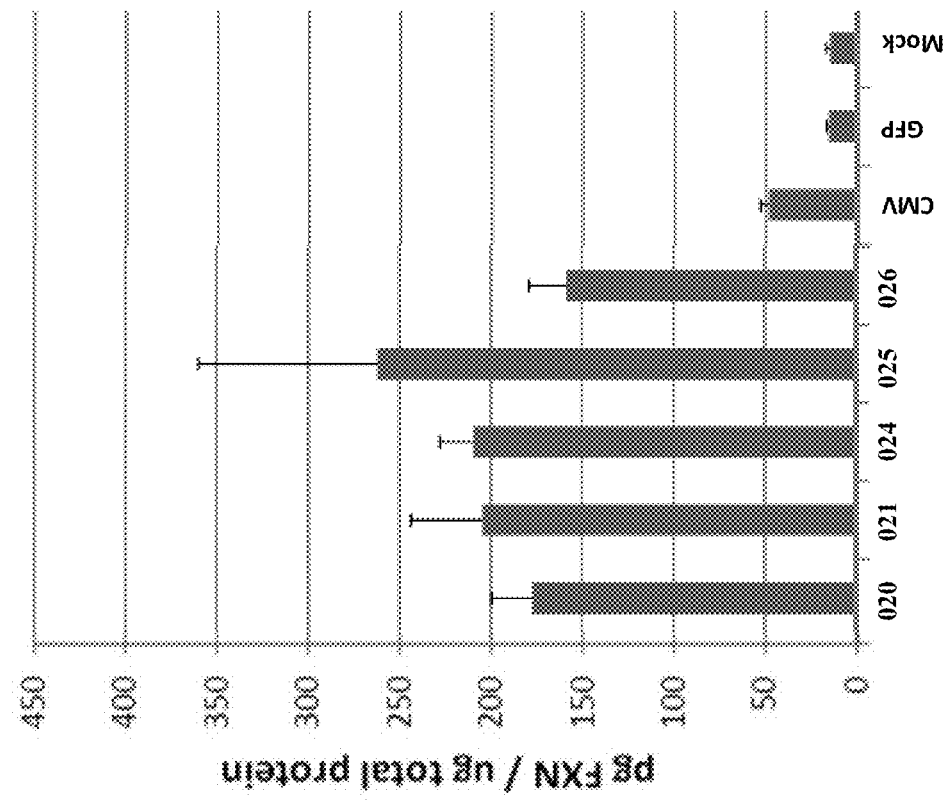
Figure 6A:
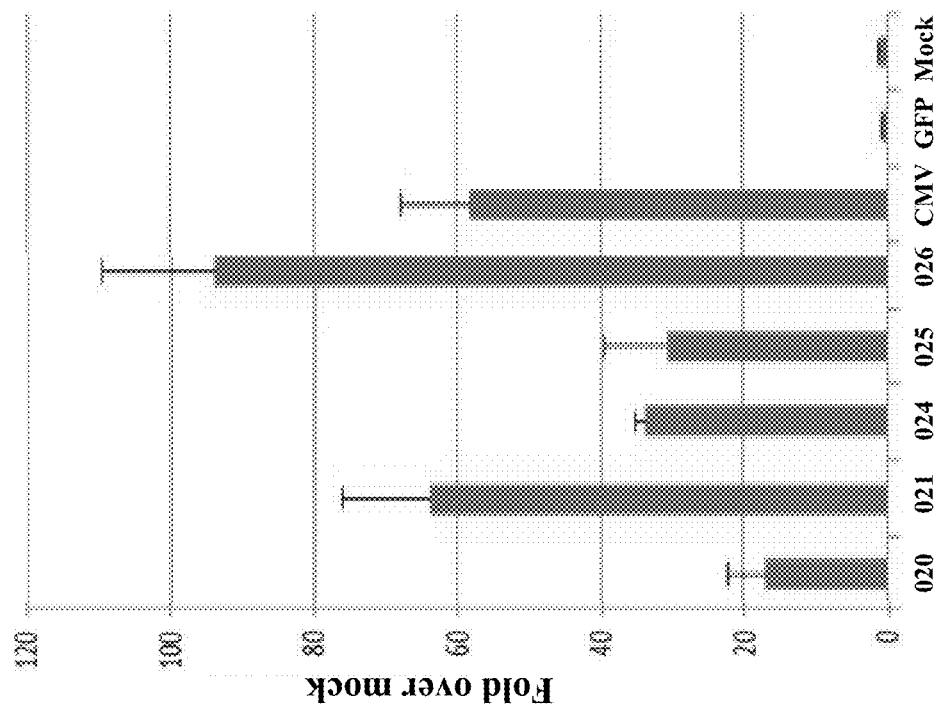
FIGS. 6A-6B show the Tier 3 results for selected constructs employing the UBC promoter in FA patient fibroblasts, along with the Green Fluorescent Protein (GFP), CMV and Mock controls.
Figure 6B:
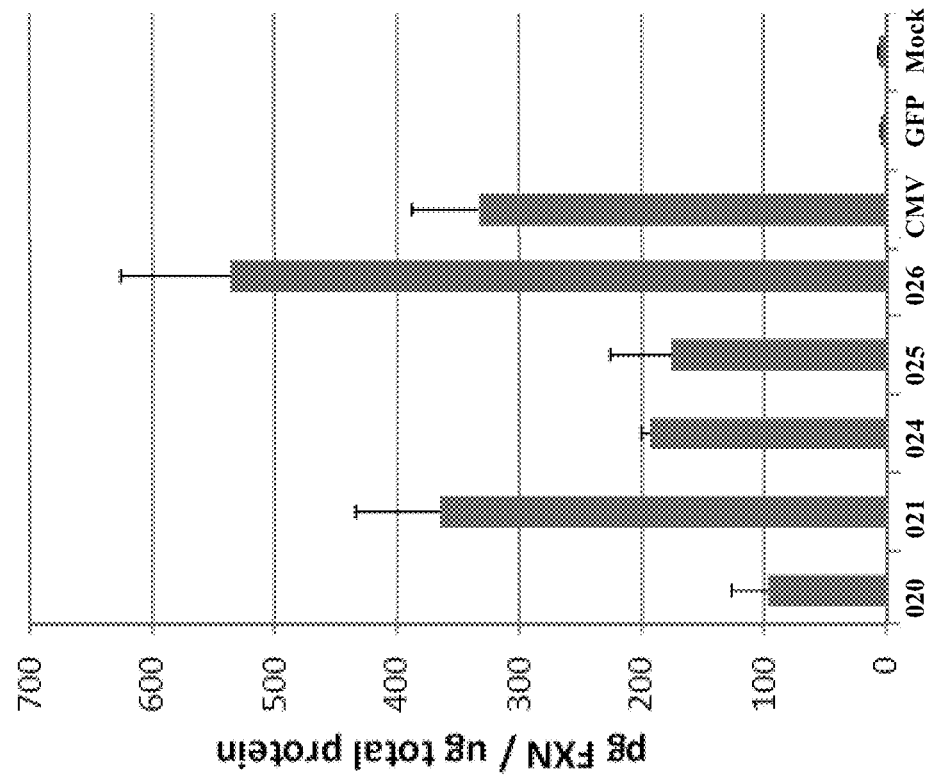

Based on the combined results from the primary (Tier 1) and secondary (Tier 2) screens, 14 FXN constructs were selected for further development. Results from the second run execution of the Tertiary (Tier 3) screen are shown below in FIG. 5 and FIG. 6 for both cell types.

Example 2

Figures 7A, 7B:
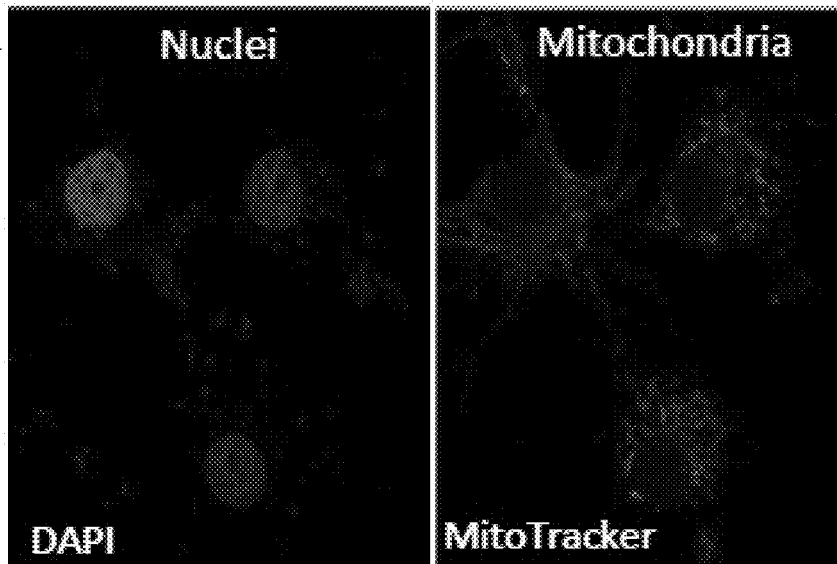
FIGS. 7A-7D show human frataxin being expressed and appropriately trafficked into the mitochondria by fluorescence images of African green monkey fibroblasts (COS-7) transfected with human Frataxin.
Figures 7C, 7D:
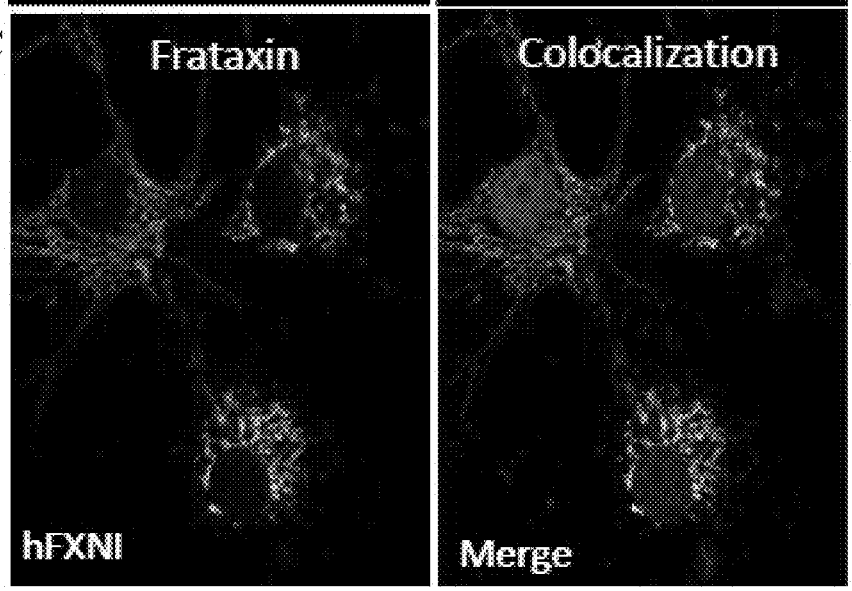
Figure 8A:
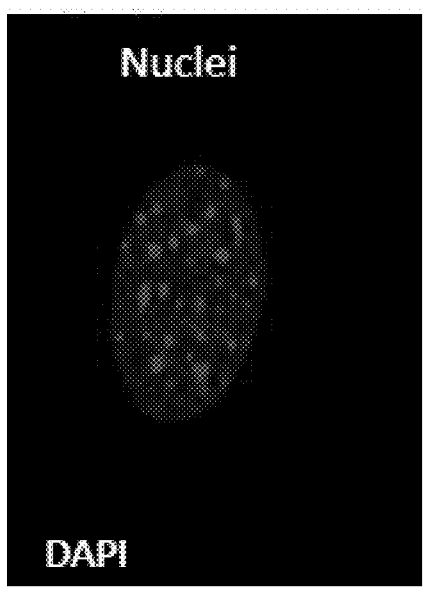
FIGS. 8A-8D show human frataxin being expressed and appropriately trafficked into the mitochondria by fluorescence images of murine fibroblasts (NC6) transfected with human Frataxin.
Figure 8B:
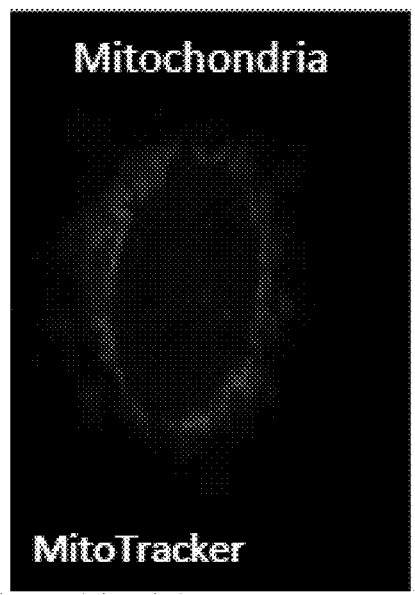
Figure 8C:
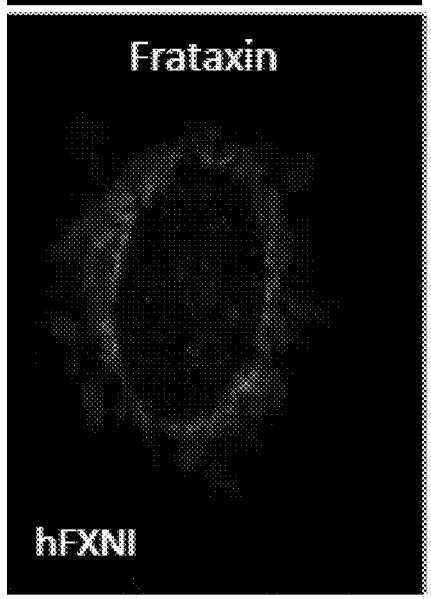
Figure 8D:
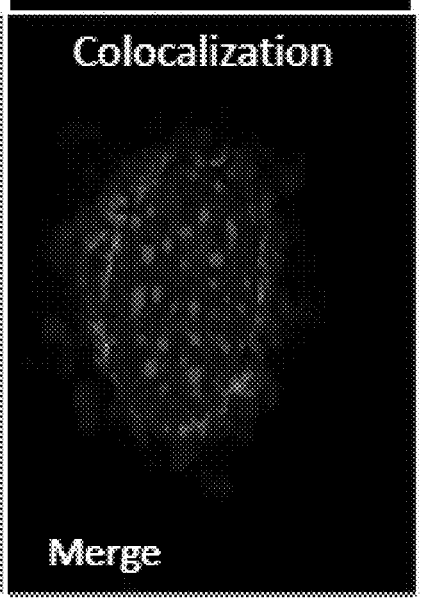

To demonstrate the site of expression of frataxin in cells, African green monkey fibroblasts (COS-7) or murine fibroblasts (NC6) were grown on glass coverslips under standard culture conditions. The culture medium was removed and the cells were fixed with 1 ml 3.7% formalin/phosphate buffered saline (PBS) at room temperature for 10 min. The cells were washed three times for 10 minute with 2 ml PBS and then were treated with blocking solution (1 ml 2% fetal bovine serum/0.2% Triton X-100/PBS) for 1 hour at room temperature. Following an overnight incubation at 40° C. with an anti-human frataxin antibody (1:500 dilution in blocking solution, Abcam #ab11038), the cells were washed three times for 10 minute with PBS-T (0.2% Tween 20/PBS). The cells were then incubated in the dark with 250 ul of secondary detection antibody (Alexa Fluor 488 Gt anti-Ms IgG, Thermo Fisher #A-11017) at 1:500 dilution in blocking buffer for 1 hour at room temperature. Following three 10 minute washes with PBS-T, the coverslips containing the cells were placed face-down onto microscope slides with one drop of VectaShield Hard Set with the nuclear counterstain, DAPI (Vector #H1500), and analyzed by confocal microscopy. In FIG. 7, Panel A, nuclei were stained with DAPI. In Panel B, mitochondria were stained with MitoTracker. Panel C shows staining with anti-human frataxin. The merged colocalization is shown in Panel D and demonstrates that Frataxin is being expressed in the mitochondria of the COS cells (FIG. 7) and NC6 cells (FIG. 8).

Example 3

To demonstrate that human frataxin is expressed and correctly processed in cells, the following experiment was conducted. Inducible pluripotent stem cells (iPSCs) derived from FA patients can be differentiated into cardiomyocyte and neuronal cell types, specific cell types which are affected in FA patients, and maintain reduced frataxin levels and triplet repeat instability (Liu et al. (2011) *Stem Cell Rev.* 7(3):703-713; Polak et al. (2012) *J. Vis. Exp.* 60:3416; Du et al. (2012) *J. Biol. Chem.* 287(35):29861-29872). The neuronal cells are referred to as FA-iPSCs. FA (3816) Day 21 neurons were transduced with AAV5-human frataxin (026) at 500,000 genome copies/cell. The neurons were harvested in passive lysis buffer (Promega #E1941) with proteinase inhibitors at days 5, 7, 10, and 14 post-transduction. Total protein from the cells was isolated using sonication. The protein concentration was calculated using the Bradford method. 30 ug total protein per lane was separated by SDS-PAGE (Thermo Fisher #NW04120BOX, 4-12% NuPage). Human frataxin was detected with an anti-human frataxin antibody (Abcam #ab11038) using standard Western blot techniques. Molecular weight markers were loaded to confirm the size of the mature frataxin protein (14.2 kDa). FIG. 9 Panel A shows day 21 neurons harvested at days 5 and 7 post-transduction (FA+) along with non-transduced cells (FA) and IPSCs derived from normal patients, which served as control cells (Ctrl). FIG. 9 Panel B shows day 21 neurons harvested at days 10 and 14 post-transduction (FA+) along with non-transduced cells (FA) and IPSCs derived from normal patients, which served as control cells (Ctrl). The results show that human frataxin is expressed and correctly processed in the FA-AAV5 transduced cells.

Figure 10:
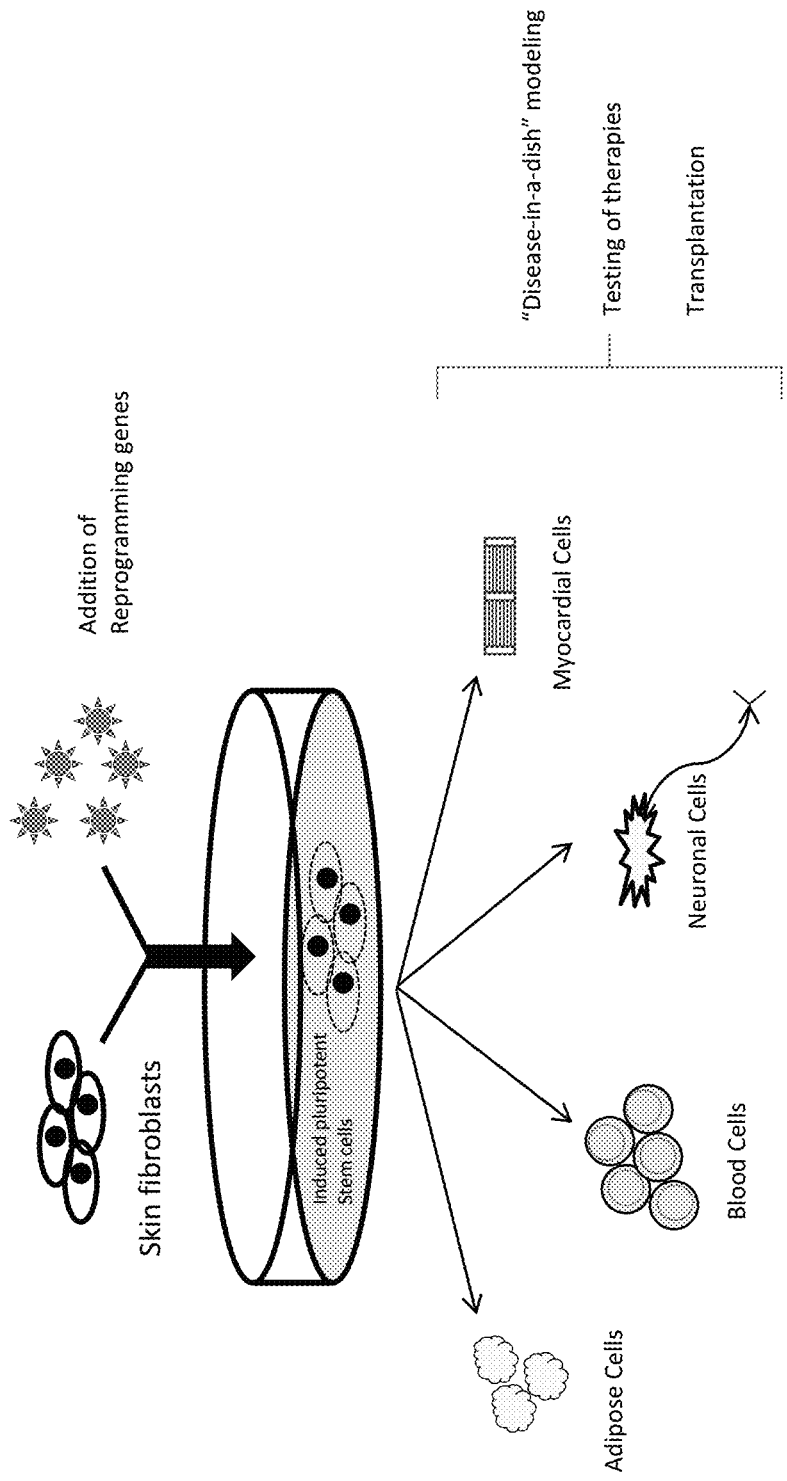
FIG. 10 shows a cartoon of the strategy of reprogramming fibroblasts to become pluripotent cells which can differentiate into various cell types for use in modeling, testing of therapies and for transplantation.

FIG. 10 shows a schematic of the uses of stem cell therapy (adapted from "Stem Cell Therapy: A Panacea or Perturbed Claim!" (Dec. 30, 2014) (source: stemcells.uct.ac.za).

Example 4

Figure 11:
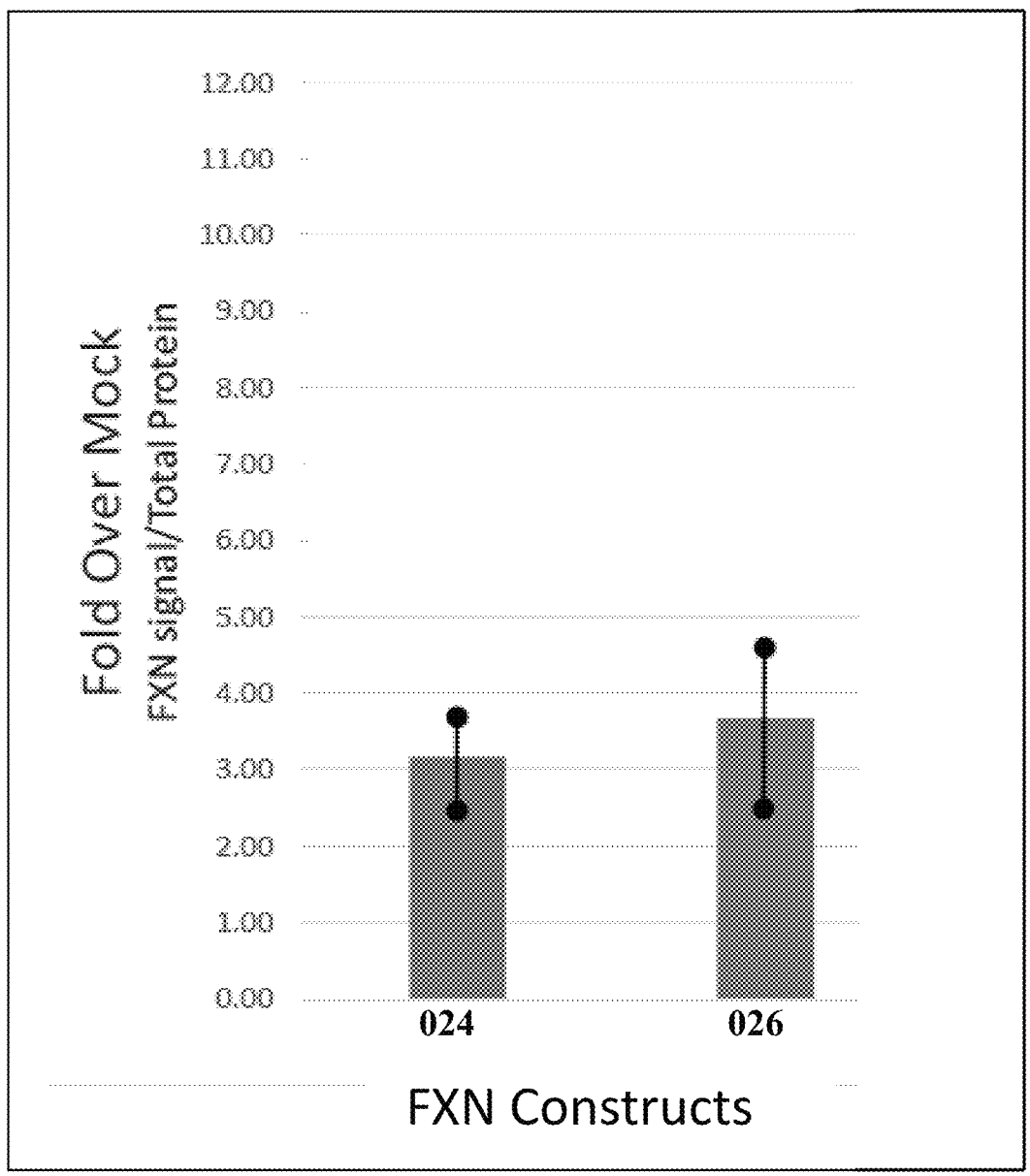
FIG. 11 shows the results of frataxin expression from iPSC-derived neuronal cells transformed by electroporation of a frataxin-expressing plasmid for the 024 and 026 constructs (see Table 1) as expressed by fold over mock (GFP-treated) cells.

Day 8 iPSCs were transfected with 2 μg DNA of the human frataxin DNA construct, 024 or 026, using the BioRad Gene Pulser Xcell electroporation system. Frataxin protein expression was determined after 4 days treatment (day 12 iPSCs) using the Frataxin Protein Quantity Dipstick Assay (AbCam #ab109881) and is expressed as frataxin antibody signal/mg total protein. The fold increase in the frataxin expression was calculated by dividing the mean frataxin concentration/signal in treated cells by the frataxin concentration/signal in mock control (GFP treated) cells. FIG. 11 shows that both 024 and 026 exhibited a mean frataxin concentration/signal of greater than 3 fold and 3.5 fold, respectively.

Example 5

Figure 12:
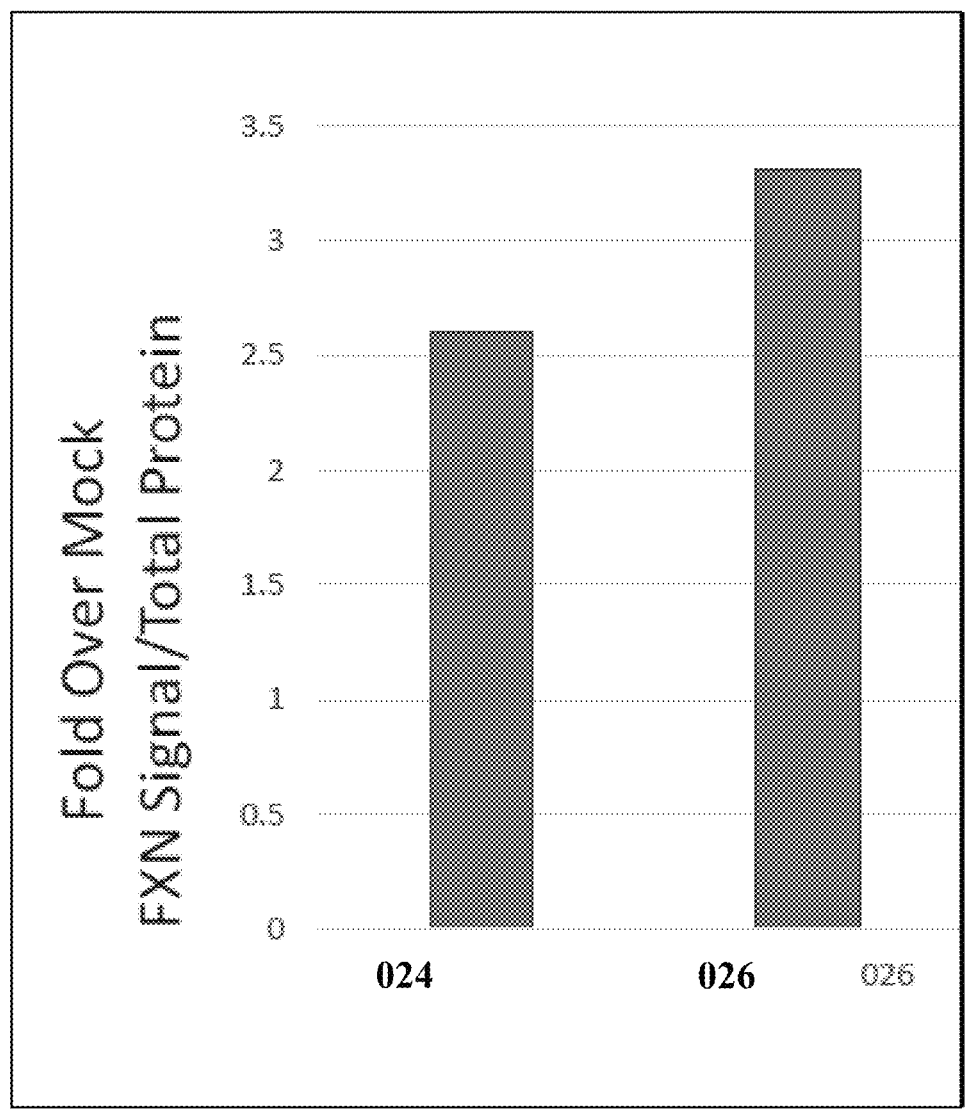
FIG. 12 shows the results of frataxin expression from iPSC-derived neuronal cells transduced with frataxin-expressing AAV for the 024 and 026 AAV constructs (see Table 1) as expressed by fold over mock (GFP-treated) cells.

Day 8 iPSCs were transduced with AAV5-human frataxin (AAV5-hFXN) 024 and 026 at a multiplicity of infection (MOI) of $3.75 \times 10^9$ vector genomes (vg)/cell. Frataxin protein expression was determined after 4 days treatment (day 12 iPSCs) using the Frataxin Protein Quantity Dipstick Assay (AbCam #ab109881) and is expressed as frataxin antibody signal/mg total protein. The fold increase in the frataxin expression was calculated by dividing the mean frataxin concentration/signal in treated cells by the frataxin concentration/signal in mock control (GFP treated) cells. FIG. 12 shows that both 024 and 026 exhibited a mean frataxin concentration/signal of greater than 2.5 fold and 3.5 fold, respectively.

Example 6

Figure 13:
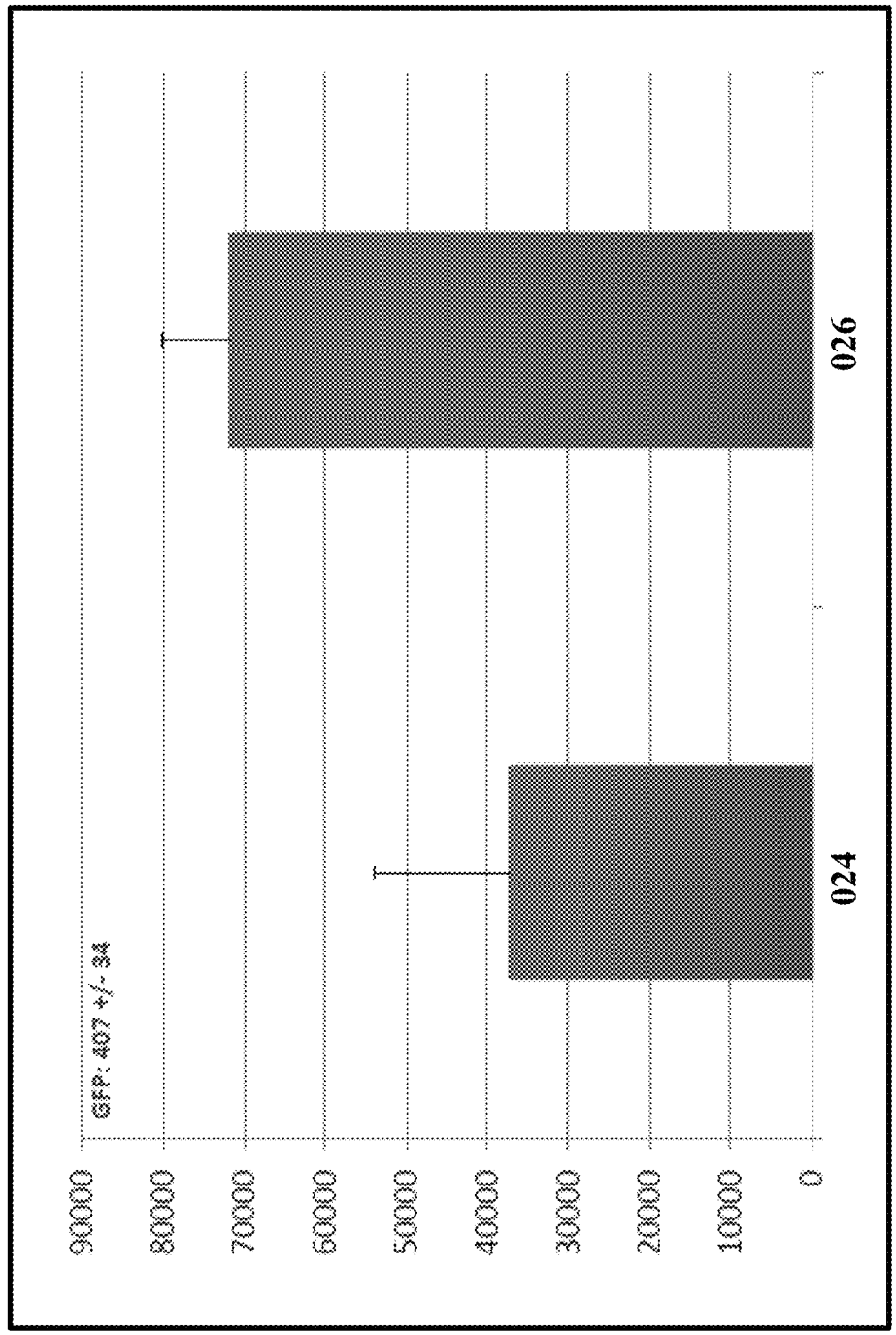
FIG. 13 shows expression of frataxin (pg FXN/mg protein) in the cerebellum of mice intraparenchymally administered AAV5-FXN-026.

AAV5-human frataxin vector was injected directly into the cerebellum (CB) of four normal wild-type (WT) mice at a dose of $7 \times 10^9$ vg in 3 μl. At 4 weeks post injection, the cerebellum was harvested from treated mice as well as two untreated mice. Tissue lysates were analyzed for human frataxin expression using the Human Frataxin Simple Step ELISA (Abcam #176112) and normalized to pg frataxin/mg total protein. FIG. 13 shows that greater than 30 ng and 70 ng of frataxin were detected for 024 and 026 cerebellar lysates, respectively. No expression of human frataxin was detected in the untreated animals (data not shown).

Example 7

Figure 14:
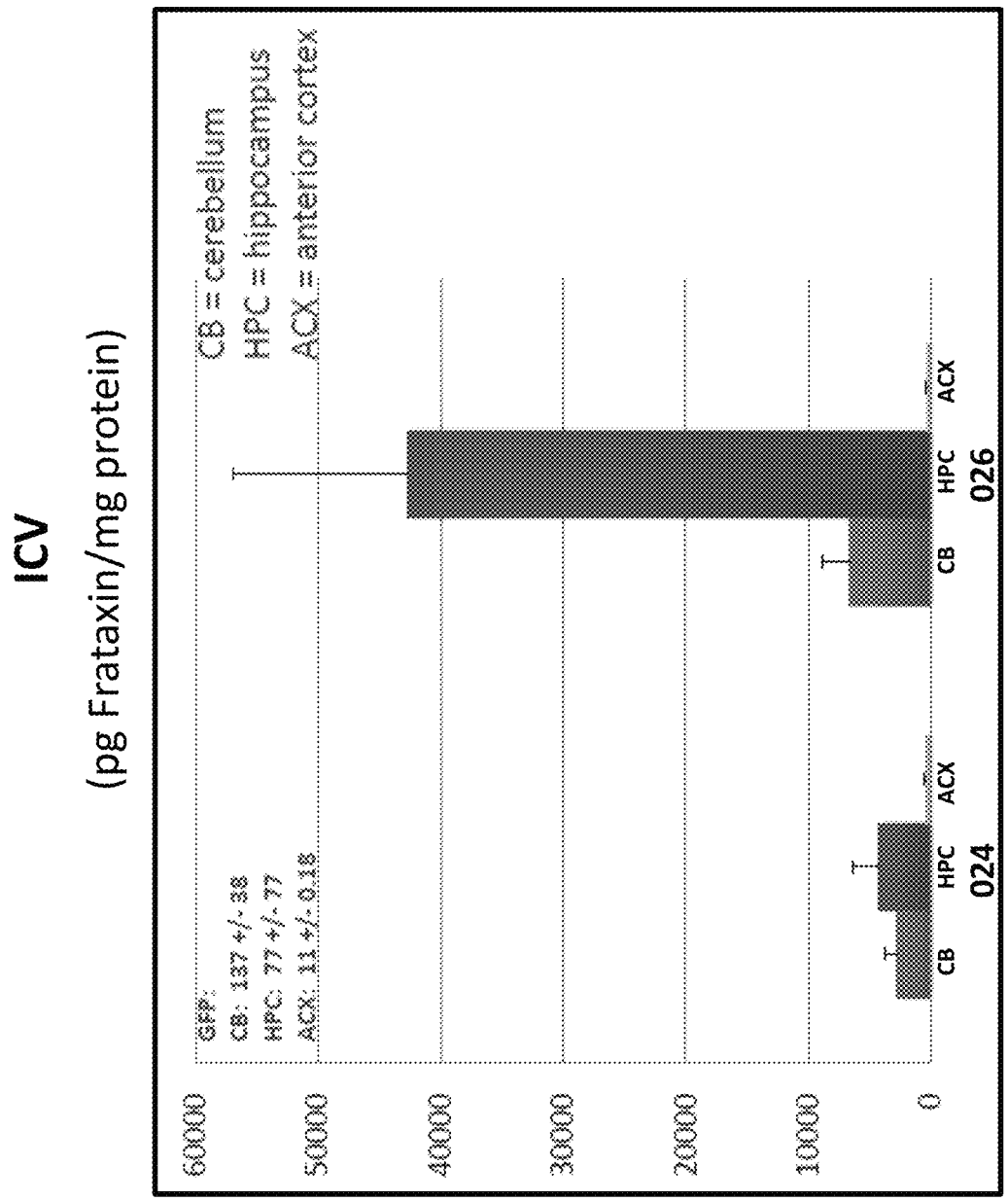
FIG. 14 shows expression of frataxin (pg FXN/mg protein) in the cerebellum (CB), hippocampus (HPC) and anterior cortex (ACX) of mice intraventricularly administered AAV5-FXN 026.

AAV5-human frataxin vector was administered by intracerebroventricular injection into four normal wild-type (WT) mice at a dose of $7 \times 10^9$ vg in 3 μl. At 4 weeks post injection, the cerebellum (CB), the hippocampus (HPC), and anterior cortex (ACX) were harvested from treated mice as well as from two untreated mice. Tissue lysates were analyzed for human frataxin expression using the Human Frataxin Simple Step ELISA (Abcam #176112) and normalized to pg frataxin/mg total protein. No expression of human frataxin was detected in the untreated animals (data not shown). FIG. 14 shows that the accumulation of frataxin was greatest in the hippocampus in both 024 and 026, however, 026 showed greater than 8 fold more frataxin in the hippocampus than 024.

Example 8

Clinical study of AAV5.hFXN vector gene therapy

AAV5.hFXN vector is formulated in a sterile solution containing standard compendial excipients. The vector is administrated by intrathecal (IT) injection. The total dose is of $5 \times 10^{13}$ vg to $5 \times 10^{14}$ vg in a maximum volume of 10 mL, which is approximately 5% of the average cerebrospinal fluid (CSF) volume in humans of approximately 200 mL (See D. Agamanolis 2013, *Neuropathology: An illustrated interactive course for medical students and residents*. Chapter 14: Cerebrospinal Fluid.; Brown et al., "Molecular Mechanisms of Cerebrospinal Fluid Production. Neuroscience." 2004, 129(4): 957-970.).

A Phase 1, 3+3 single ascending dose study evaluates the safety of AAV5.hFXN in adult patients with FA. A single dose of AAV5.hFXN pharmaceutical formulation is administered intrathecally to successive cohorts of 3 subjects each. Three ascending doses of AAV5.hFXN are administered, with a review of safety by an independent DSMB prior to enrollment of the next higher dose level. Safety and neurological evaluations are performed periodically for 24 months post dose. Functional assessments are performed.

A Medtronic Model 8781 ASCENDA™ Intrathecal Catheter System that can deliver parenteral drugs to the intrathecal space is used. The Catheter System components include a Medtronic pump and the catheter system—the catheter is implanted in a sterile surgical procedure performed under general or regional anesthesia. The Catheter System is inserted at the lumbar level, where half of the dose to be administered is injected, and then the catheter is threaded to the level of the cisterna magna using guided imaging, where the remaining half of the dose is injected.

Three optional doses are studied. The low dose tested in the clinical trial is $5 \times 10^{13}$ vg. The middle dose is $1.5 \times 10^{14}$ vg. The high dose is $5 \times 10^{14}$ vg. Non-limiting Exemplary doses are shown in Table 6.

TABLE 6

| Total Vector Dose (vg) | Total Dose - CSF Volume Basis (vg/mL) | Total Dose - Brain Weight Basis (vg/g) |
| --- | --- | --- |
| $5.0 \times 10^{13}$ | $2.5 \times 10^{11}$ | $3.7 \times 10^{10}$ |
| $1.5 \times 10^{14}$ | $7.5 \times 10^{11}$ | $1.11 \times 10^{11}$ |
| $5.0 \times 10^{14}$ | $2.5 \times 10^{12}$ | $3.7 \times 10^{11}$ |

Efficacy data is collected at 1, 3, 6 and 12 months post study drug administration. Efficacy is evaluated in subjects using diffusion tensor imaging and various functional outcomes (including but not limited to FARS total and FARS Neuro; evaluation of a 25-foot walk test; evaluation on a GAITRite Walkway System; evaluation using a Biodex Balance System SD; evaluation using the 9-hole peg test). Diffusion tensor imaging may be measured, for example, by T2 relaxometry of dentate nucleus and DRG and/or NAA levels and iron levels by Magnetic Resonance Imaging (MRS).

Example 9

Treatment of Friedrich's Ataxia with AAV5.hFXN Vector Gene Therapy Intracerebellar Administration A $5.0 \times 10^{13}$(vg) Total Vector Dose of AAV5.hFXN vector pharmaceutical formulation ($2.5 \times 10^{13}$ vg/mL with 1×PBS at a pH of 7.4) is administered to a 30-year-old patient with Friedreich's ataxia. The vector delivers hFXN gene into the central nervous system of the Fredrich ataxia patient. The pharmaceutical formulation is administered as a single bolus intracerebellar injection. The rate of injection is controlled by a Medtronic SynchroMed®EL 18-mL pump. The $5.0 \times 10^{13}$(vg) Total Vector Dose is administered at a rate of 0.001 mL/min and at a concentration of $2.5 \times 10^{13}$ vg/mL. Total volume=2 mL.

Improved function relative to natural disease progression is observed. The increases from baseline in FARS total and FARS Neuro score improve over time and achieve statistical significance by 6 months after the procedure. Integrated analyses of the patient's FARS total and FARS Neuro, 25-foot walk test, GAITRite Walkway System, Biodex Balance System SD, 9-hole peg test scores demonstrate statistically significant improvement in gross and fine motor skills as early as 6 months after gene therapy. A significant treatment benefit seen on motor skills generally continues to improve over time. After surgery, the patient demonstrates generally continuous increases in their FARS total and FARS Neuro, 25-foot walk test, GAITRite Walkway System, Biodex Balance System SD, 9-hole peg test scores. Safety and neurological evaluations are performed periodically for 24 months post dose. Functional assessments are performed. In conclusion, the present disclosure using AAV viral vectors to transfer hFXN genes for treating Friedrich's Ataxia is practical and effective.

Example 10

Treatment of Friedrich's Ataxia with AAV5.hFXN Vector Gene Therapy Intracerebellar Administration A $5.0 \times 10^{14}$(vg) Total Vector Dose of AAV5.hFXN vector pharmaceutical formulation ($2.5 \times 10^{14}$ vg/mL with 1×PBS at a pH of 7.4) is administered to a 30-year-old patient with Friedreich's ataxia. The vector delivers hFXN gene into the central nervous system of the Friedrich ataxia patient. The pharmaceutical formulation is administered as a single bolus intracerebellar injection. The rate of injection is controlled by a Medtronic SynchroMed®EL 18-mL pump. The $5.0 \times 10^{14}$(vg) Total Vector Dose is administered at a rate of 0.01 mL/min and at a concentration of $2.5 \times 10^{14}$ vg/mL. Total volume=2 mL.

Improved function relative to natural disease progression is observed. The increases from baseline in FARS total and FARS Neuro score improve over time and achieve statistical significance by 6 months after the procedure. Integrated analyses of the patient's FARS total and FARS Neuro, 25-foot walk test, GAITRite Walkway System, Biodex Balance System SD, 9-hole peg test scores demonstrate statistically significant improvement in gross and fine motor skills as early as 6 months after gene therapy. A significant treatment benefit seen on motor skills generally continues to improve over time. After surgery, the patient demonstrates generally continuous increases in their FARS total and FARS Neuro, 25-foot walk test, GAITRite Walkway System, Biodex Balance System SD, 9-hole peg test scores. Safety and neurological evaluations are performed periodically for 24 months post dose. Functional assessments are performed. In conclusion, the present disclosure using AAV viral vectors to transfer hFXN genes for treating Friedrich's Ataxia is practical and effective.

Example 11

Treatment of Friedrich's Ataxia with AAV5.hFXN Vector Gene Therapy Intracerebroventricular Administration A $3.5 \times 10^{12}$ vg Total Vector Dose of AAV5.hFXN vector pharmaceutical formulation ($7 \times 10^{12}$ vg/mL with DPBS at a pH of 7.0) is administered to a 25-year-old patient with Friedreich's ataxia. The vector delivers hFXN gene into the central nervous system of the Friedrich ataxia patient. The pharmaceutical formulation is administered as a single bolus intracerebroventricular injection to the CSF space of the patient. The rate of injection is controlled by a Medtronic SynchroMed®EL 18-mL pump. The $3.5 \times 10^{12}$ vg Total Vector Dose is administered at a rate of 0.001 mL/min and at a concentration of $7 \times 10^{12}$ vg/mL. Total volume=0.5 mL.

Improved function relative to natural disease progression is observed. The increases from baseline in FARS total and FARS Neuro score improve over time and achieve statistical significance by 6 months after the procedure. Integrated analyses of the patient's FARS total and FARS Neuro, 25-foot walk test, GAITRite Walkway System, Biodex Balance System SD, 9-hole peg test scores demonstrate statistically significant improvement in gross and fine motor skills as early as 6 months after gene therapy. A significant treatment benefit seen on motor skills generally continues to improve over time. After surgery, the patient demonstrates generally continuous increases in their FARS total and FARS Neuro, 25-foot walk test, GAITRite Walkway System, Biodex Balance System SD, 9-hole peg test scores. Safety and neurological evaluations are performed periodically for 24 months post dose. Functional assessments are performed. In conclusion, the present disclosure using AAV viral vectors to transfer hFXN genes for treating Friedrich's Ataxia is practical and effective.

Example 12

Treatment of Friedrich's Ataxia with AAV5.hFXN Vector Gene Therapy Intrathecal Administration A $5.0 \times 10^{14}$ (vg) Total Vector Dose of AAV5.hFXN vector pharmaceutical formulation ($2.5 \times 10^{14}$ vg/mL with 1×PBS at a pH of 7.4) is administered to a 30-year-old patient with Friedreich's ataxia. The vector delivers hFXN gene into the central nervous system of the Friedrich ataxia patient. The pharmaceutical formulation is administered as a single bolus intrathecal injection to the CSF space of the patient. Half of the dose is administered to the patient's lumbar, and half of the dose is administered to the patient's cisterna magna. A Medtronic Model 8781 ASCENDA™ Intrathecal Catheter System with 66 cm spinal segment is implanted in a sterile surgical procedure performed under general or regional anesthesia. The Catheter System is inserted at the lumbar level, where half of the dose to be administered is injected, and then the catheter is threaded to the level of the cisterna magna using guided imaging, where the remaining half of the dose is injected. The rate of injection is controlled by a Medtronic SynchroMed®EL 18-mL pump. The $5.0 \times 10^{14}$ (vg) Total Vector Dose is administered at a rate of 0.01 mL/min and at a concentration of $2.5 \times 10^{14}$ vg/mL. Total volume=2 mL (1 mL Lumbar+1 mL cisterna magna).

Improved function relative to natural disease progression is observed. The increases from baseline in FARS total and FARS Neuro score improve over time and achieve statistical significance by 6 months after the procedure. Integrated analyses of the patient's FARS total and FARS Neuro, 25-foot walk test, GAITRite Walkway System, Biodex Balance System SD, 9-hole peg test scores demonstrate statistically significant improvement in gross and fine motor skills as early as 6 months after gene therapy. A significant treatment benefit seen on motor skills generally continues to improve over time. After surgery, the patient demonstrates generally continuous increases in their FARS total and FARS Neuro, 25-foot walk test, GAITRite Walkway System, Biodex Balance System SD, 9-hole peg test scores. Safety and neurological evaluations are performed periodically for 24 months post dose. Functional assessments are performed. In conclusion, the present disclosure using AAV viral vectors to transfer hFXN genes for treating Friedrich's Ataxia is practical and effective.

Example 13

Sarsero Frataxin-Deficient Mouse Model

Reference is made to JP Sarsero et al., "Human BAC-mediated rescue of the Friedreich ataxia knockout mutation in transgenic mice," *Mamm. Genome*, 2004 May; 15(5):370-82. The FVB; B6.Tg(FXN); FXN-mouse model (#018299, The Jackson Laboratories) is hemizygous for the human FXN*500GAA transgene and homozygous for the frataxin knockout allele. Therefore, the mouse is null for murine frataxin and contains the human frataxin gene (with 500 GAA repeats in the first intron) inserted in Chromosome 5. The model expresses a low level of human frataxin (~10%) that rescues lethality in mice and is similar to the frataxin reduction in humans, but does not generate any disease phenotypes characteristic of FA.

A. Methods

Mice were anesthetized with isoflurane and placed in the stereotaxic apparatus (51725D Digital Just for Mice Stereotaxic Instrument, Stoelting, Wood Dale, Ill.). An incision was made sagittally over the middle of the cranium and the surrounding skin was pushed back to enlarge the opening. Burr holes were drilled in the skull using a Dremel drill and a dental bit under stereotaxic guidance. Mice received bilateral intracerebellar injections of either 2 L of AAV5-FXN-026 at a concentration of $7 \times 10^{12}$ vector genomes/mL (N=7) or AAV5-GFP (control) at a concentration of $4 \times 10^{12}$ vector genomes/mL (N=3) using a 10 μL Hamilton syringe with a 27-gauge blunt end needle/glass capillary. Virus was injected at 2.5 μL/min using a convention enhanced delivery method. The surgical incision was closed with nylon (Ethilon®) sutures. Alternatively, mice received bilateral intracerebroventricular injections of either 2 μL of AAV5-FXN-026 at a concentration of $7 \times 10^{12}$ vg/mL (N=7) or AAV5-GFP (control) at a concentration of $4 \times 10^{12}$ vg/mL (N=3) using a 10 μL Hamilton syringe. At 4 weeks post injection, the cerebellums were harvested. Cerebellar tissue from two untreated control mice was also harvested. Tissue lysates were analyzed for human frataxin expression using the Human Frataxin Simple Step ELISA (Abcam #176112), an assay that specifically detects human frataxin.

B. Results

Following different routes of administration of the AAV5-FXN-026 vector, the expression of frataxin protein in specific tissues was evaluated as shown in FIG. 21. The detectable level of endogenous frataxin protein in the cerebellum was the result of expression from the incorporated human frataxin transgene that rescues the null murine frataxin phenotype. After intraparenchymal (IPc) administration to the cerebellum, an approximately 7-fold increased expression of frataxin protein over control levels in the cerebellum was observed. Upon intracerebroventricular (ICV) administration, there was over a 4-fold increased expression of frataxin protein over control levels in the cerebellum.

C. Conclusions

AAV5-FXN-026 increased frataxin expression in the cerebellum of frataxin-deficient mice by approximately 4-fold via ICV administration and approximately 7-fold following IPc injection. The increased expression over control levels of human frataxin protein from AAV5-FXN-026 in a mouse model of FA, provides evidence that the promoter/regulatory elements in the DNA construct in AAV5-FXN-026 are functional in the complex in vivo environment. Assuming a 10% level of normal frataxin expression in this mouse model, the level of exogenous frataxin achieved following transduction would be 40-70% of normal and in a range that is asymptomatic in humans.

Example 14

Route of Administration Comparison Study in Pigs

Biodistribution of the test article, AAV5-FXN-026, was studied in swine using several delivery locations and devices. Five treatment groups of three male Yucatan swine underwent a surgical procedure in which the dosing site(s) (lumbar, lumbar and cisterna magna, or dentate nucleus) was accessed. The test article was administered on Day 0 via a spinal needle in the lumbar (Group 2), a Medtronic ASCENDA™ catheter in the lumbar and cisterna magna (Group 3), an Alcyone Pulsar catheter in the lumbar and cisterna magna (Group 4), a spinal needle in the dentate nucleus (Group 5), or an Alcyone MEMS cannula (AMC™) in the dentate nucleus (Group 6). The test article was administered at a dose level of $3 \times 10^3$ (Groups 2 to 4) or $3 \times 10^{12}$ (Groups 5 and 6) viral genomes (vg) and a dose volume of 2.2 to 2.3 or 0.12 to 0.146 mL, respectively. One animal served as the control and did not undergo a surgical procedure or treatment (Group 1). The animals were maintained for a 28±1 day recovery period.

Observations for morbidity, mortality, injury, and the availability of food and water were conducted twice daily for all animals. Clinical observations were conducted for all animals daily on Days −1 to 7 and weekly thereafter. Body weights were measured and recorded for all animals weekly, beginning during Week −1. Physical examinations were conducted for all animals pretest. At study termination, necropsy examinations were performed and selected tissues were analyzed for concentrations of the test article by qPCR analysis.

Biodistribution results were variable within and between each group. AAV5-FXN-026 levels in the area of the dentate nucleus of the cerebellum, was highest in those animals receiving direct infusion into the cerebellum (Groups 5 and 6).

A. Surgical Procedure

The test article was administered on Day 0 via a spinal needle in the lumbar (Group 2, 2.2 mL at $3 \times 10^{13}$ vg), a Medtronic ASCENDA catheter in the lumbar and cisterna magna (Group 3, 2.2 mL at $3 \times 10^{13}$ vg), an Alcyone Pulsar catheter in the lumbar and cisterna magna (Group 4, 2.2 to 2.3 mL at $3 \times 10^3$ to $3.14 \times 10^{11}$ vg), a spinal needle in the dentate nucleus (Group 5, 0.12 mL at $3 \times 10^{13}$ vg), or an Alcyone MEMS cannula (AMC™) in the dentate nucleus (Group 6, 0.13 to 0.146 mL at $2.71 \times 10^{12}$ to $3.04 \times 10^{12}$ vg). One animal served as the control and did not undergo a surgical procedure or treatment (Group 1). The animals were maintained for a 28±1 day recovery period.

(a). Group 2—Lumbar Injection (Spinal Needle)

Each animal was placed in ventral recumbency. An incision was made in the skin just caudal to L2-L3. A 14G spinal needle was advanced into the intrathecal space at L2-L3. Placement was verified by fluoroscopic imaging and/or hanging drop technique as well as back flow of cerebral spinal fluid (CSF). A fluoroscopic image of the needle placement was taken, and catheter placement was verified with a contrast injection of Omnipaque-300. The needle was flushed with 1.5 mL of saline. The test article (2.2 mL) was drawn up into a 3 cc syringe and dosed over 48 to 72 seconds. A dwell time of at least 1 minute was allowed after completion of the injection. The needle was removed, and the incision was closed in standard fashion using any combination of absorbable sutures, skin staples, or skin glue.

(b). Group 3—Lumbar and Cisterna Magna Injection (Medtronic ASCENDA™, Model 8780 Catheter)

Each animal was placed in ventral recumbency. An incision was made in the skin just caudal to L3-L4. A 16G introducer needle was advanced into the intrathecal space at L3-L4. Placement was verified by fluoroscopic imaging and/or hanging drop technique as well as back flow of CSF. A fluoroscopic image of the needle placement was taken, and catheter placement was verified with a contrast injection of Omnipaque-300. The Medtronic ASCENDA™ catheter was advanced under fluoroscopic guidance with the target of the cisterna magna region. The introducer needle was withdrawn from the intrathecal space, and the catheter was flushed with 1.5 mL of saline. The test article (2.2 mL) was drawn up into a 3 cc syringe. One half of the total volume of the test article (1.1 mL) was dosed into the cisterna magna over 30 seconds and flushed with 1 mL saline. The catheter was repositioned in the upper lumbar region (L1) under fluoroscopic guidance, and the second half the total volume of the test article (1.1 mL) was dosed over 30 to 45 seconds and flushed with 1 mL saline. The catheter was then removed, and the incision was closed in standard fashion using any combination of absorbable sutures, skin staples, or skin glue.

(c). Group 4 Lumbar and Cisterna Magna Injection (Alcyone Pulsar Catheter)

Each animal was placed in ventral recumbency. An incision was made in the skin just caudal to L3-L4. A 16G introducer needle was advanced into the intrathecal space at L2-L3 or L3-L4. Placement was verified by fluoroscopic imaging and/or hanging drop technique as well as back flow of CSF. A fluoroscopic image of the needle placement was taken, and catheter placement was verified with a contrast injection of Omnipaque-300. The Alcylone Pulsar catheter was advanced under fluoroscopic guidance to the cisterna magna region. The introducer needle was withdrawn from the intrathecal space, and the catheter was flushed with 1.5 mL of saline. The test article (2.2 mL) was drawn up into a 3 cc syringe. One portion of the total volume of the test article (1.1 to 1.4 mL) was dosed in to the cisterna magna over 20 to 29 seconds and flushed with 1 mL saline. The catheter was repositioned to L1 under fluoroscopic guidance, and the second half of the total volume of the test article (0.9 to 1.1 mL) was dosed over 19 to 71 seconds and flushed with 1 mL saline. The catheter was then removed, and the incision was closed in standard fashion using any combination of absorbable sutures, skin staples, or skin glue.

(d). Group 5—Dentate Nucleus Injection (22 Ga Spinal Needle)

Each animal was placed in ventral recumbency. A midline dorsal incision was made on the dorsal surface of the skull extending to cervical region. The base of the skull was exposed, and a magnetic resonance imaging (MRI) fiducial was placed in the left occipital bone and sealed in place with bone wax. The skin incision was temporarily closed with suture, and the animal was transported to the MRI scanner for coronal and sagittal imaging of the cerebellum. Once the MRI was collected, it was uploaded to Osirix MD for targeting purposes. The animal was placed in a head immobilizer frame, and the incision was reopened. A craniotomy on the right side of the skull was performed with a burr. Based on the stereotaxic coordinates from Osirix, a 22G 3.50 inch spinal needle (BD Spinal Needle with Quincke point) was inserted into the right cerebellum in the area of the dentate nucleus. A fluoroscopic image of the needle placement was taken, and needle placement was verified with a contrast injection of Omnipaque-300. The test article (0.15 mL) was loaded into a microbore extension set, and a 30 μL air separation bubble was placed. The remainder of the microbore extension was filled with sterile saline. The test article (0.12 mL) was infused at a rate of 10 μL/min over approximately 12 minutes. A dwell time of at least 1 minute was allowed after completion of the dose. Bone wax was placed into the burr hole. The incision was closed in standard fashion using any combination of absorbable sutures, skin staples, or skin glue.

(e). Group 6—Dentate Nucleus Injection (Alcyone MEMS Cannula (AMC™))

Each animal was placed in ventral recumbency. A midline dorsal incision was made on the dorsal surface of the skull extending to cervical region. The base of the skull was exposed, and an MRI fiducial was placed on the left side of skull. The skin incision was temporarily closed with suture, and the animal was transported to the MRI scanner for coronal and sagittal imaging of the cerebellum. Once the MRI was collected, it was uploaded to Osirix MD for targeting purposes. The animal was placed in a head immobilizer frame, and the incision was reopened. A craniotomy on the right side of the skull was performed with a burr. Based on the stereotaxic coordinates from Osirix, the Alcyone MEMS Cannula was inserted into the right cerebellum in the area of the dentate nucleus. A fluoroscopic image of the catheter tip placement was taken. The test article (0.13 to 0.146 mL) was infused at a rate of 10 μL/min over 13 to 14 minutes and 40 seconds. Bone wax was placed into the burr hole. The incision was closed in standard fashion using any combination of absorbable sutures, skin staples, or skin glue.

B. Biodistribution Evaluations (qPCR)

Tissue samples (100 to 200 mg per organ) were collected from the brain, dorsal root ganglia ((DRG) (cervical, lumbar, and thoracic)), kidney (left), spinal cord (cervical, lumbar, and thoracic), spleen, and liver (left lateral lobe) of all surviving animals for analysis of the test article concentrations. For brain tissues, samples were taken from both right and left hemispheres maintaining laterality using an 8 mm circular punch; samples were taken from the region of the cerebellar cortex (to include Purkinje cell layer), dentate nucleus, hippocampus, and motor cortex. Spinal cord tissues were collected with an 8 mm circular punch from 4 to 6 mm axial segments in the area of the ventral horn to include both white and gray matter. DRG were collected as pairs consisting of left and right ganglia correlating to the spinal cord segments collected. A sufficient number of pairs of DRG from each spinal region specified were collected to obtain 100 to 200 mg of tissue.

Figure 22:
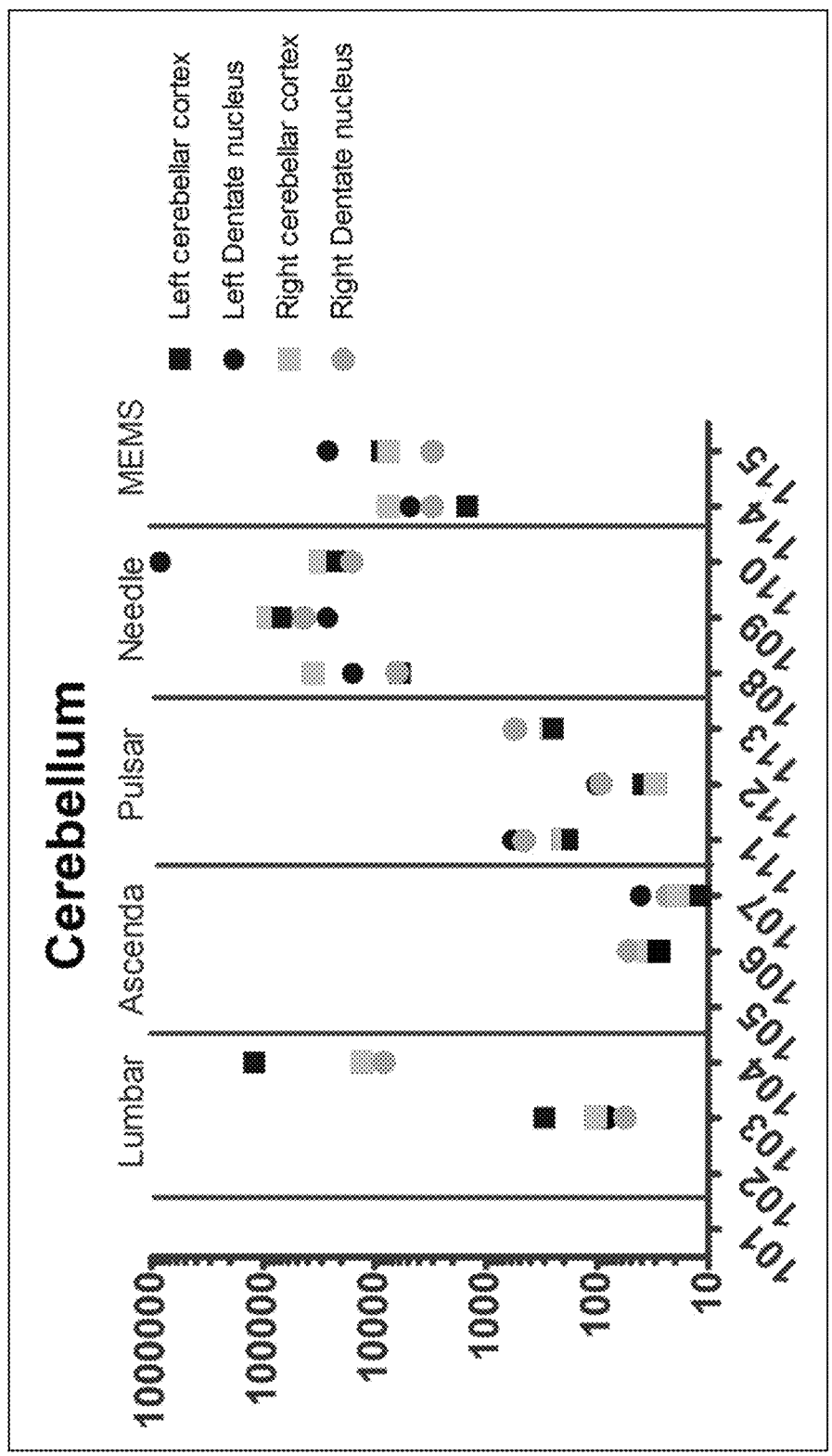
FIG. 22 is a chart showing DNA Copies per µg Tissue from Cerebellum of swine following the biodistribution of vector using several delivery locations and devices.
Figure 23:
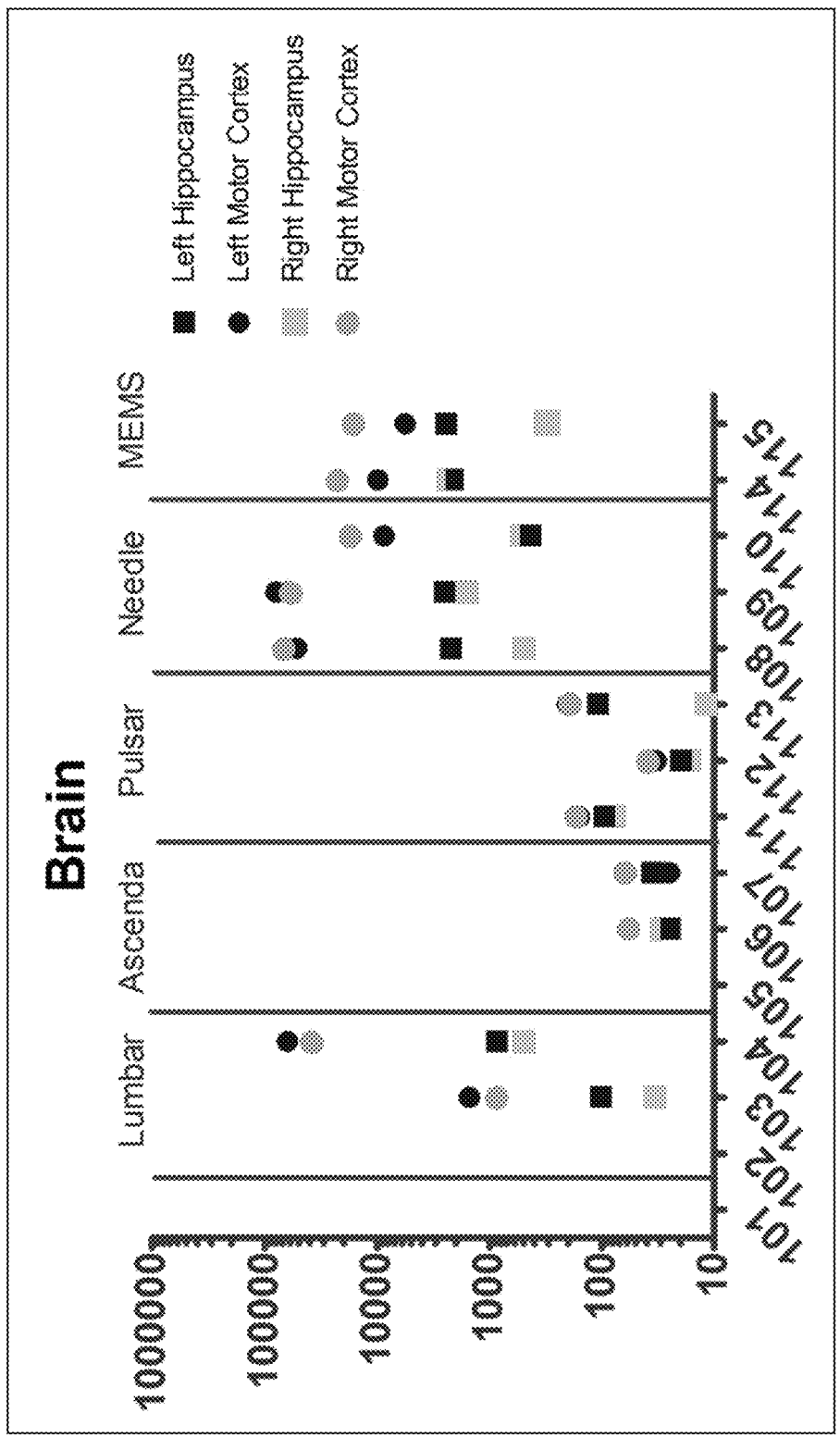
FIG. 23 is a chart showing DNA Copies per µg Tissue from Other Brain of swine following the biodistribution of vector using several delivery locations and devices.
Figure 24:
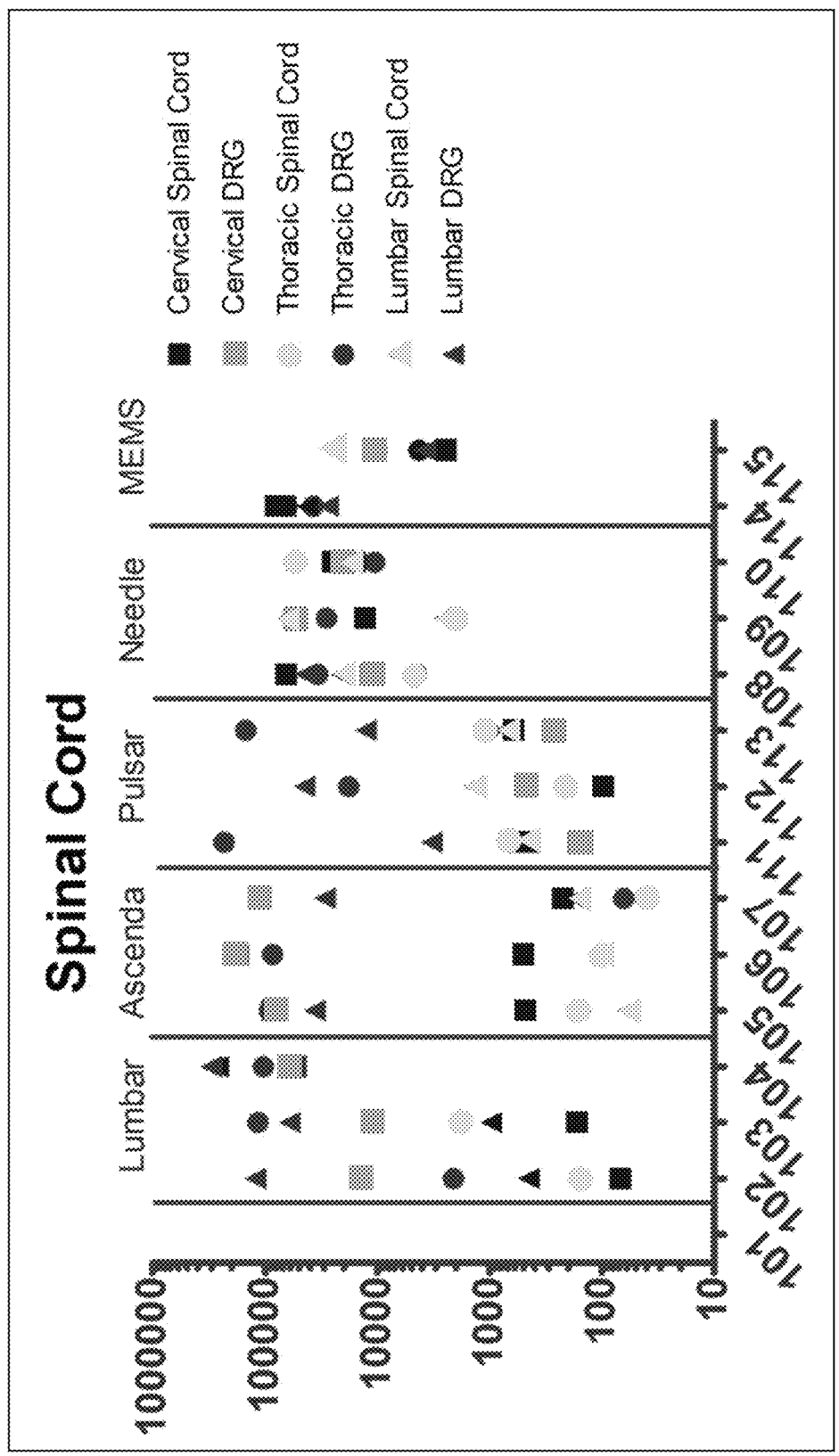
FIG. 24 is a chart showing DNA Copies per µg Tissue from Spinal Tissues of swine following the biodistribution of vector using several delivery locations and devices.
Figure 25:
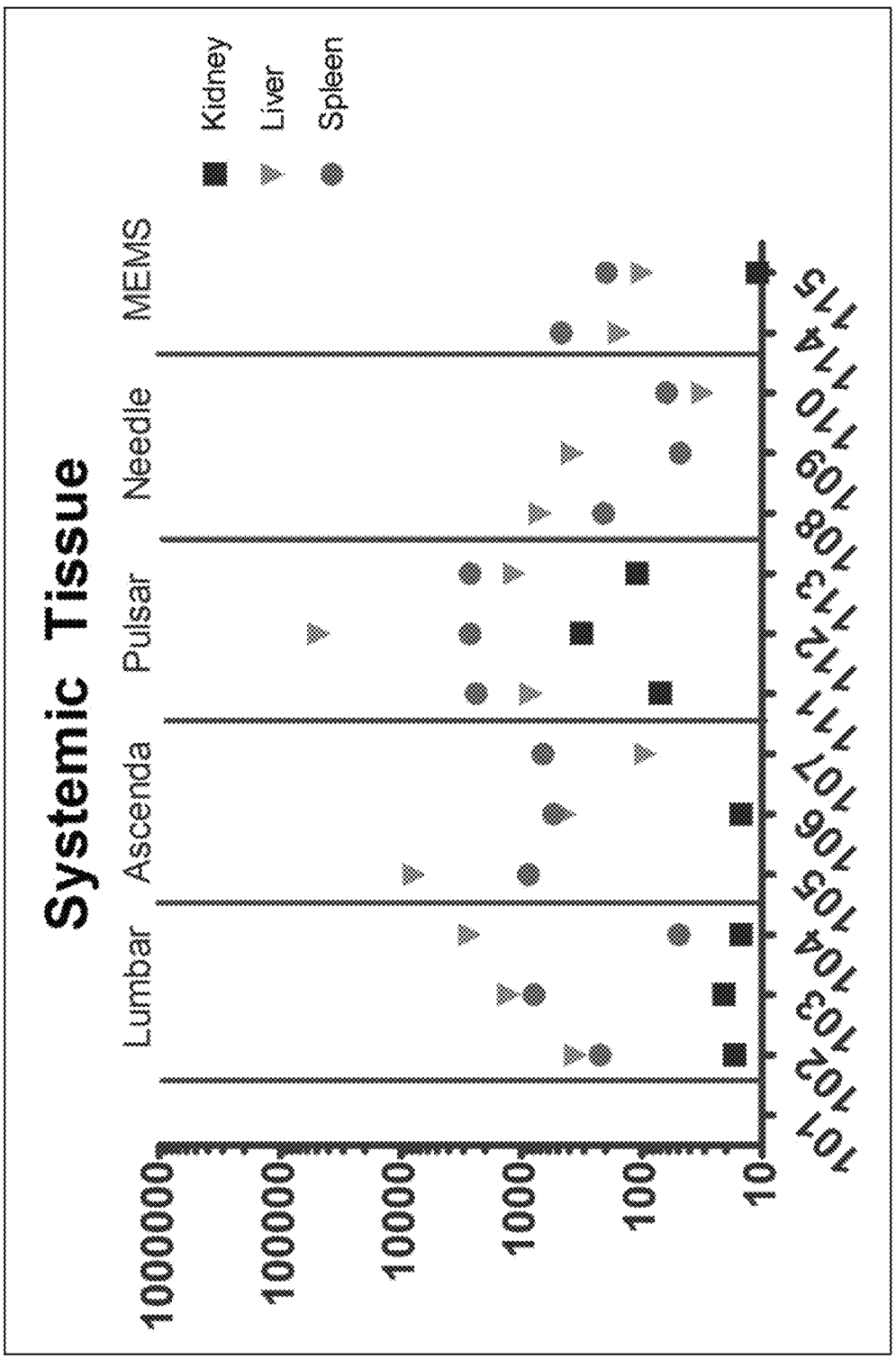
FIG. 25 is a chart showing DNA Copies per µg Tissue from Systemic Tissues of swine following the biodistribution of vector using several delivery locations and devices.

FIG. 22 shows DNA Copies per μg Tissue from Cerebellum. FIG. 23 shows DNA Copies per μg Tissue from Other Brain Areas. FIG. 24 shows DNA Copies per μg Tissue from Spinal Tissues. FIG. 25 shows DNA Copies per μg Tissue from Systemic Tissues. Intrathecal and intracranial administration of AAV5-FXN-026 was well tolerated in male Yucatan pigs weighing 51.0 to 55.2 kg. Biodistribution results were variable within and between each group. AAV5-FXN-026 levels in the area of the dentate nucleus of the cerebellum, was highest in those animals receiving diced infusion into the cerebellum (Groups 5 and 6). In general, injections with a 22 Ga spinal needle resulted in high cerebellar AAV5-FXN-026 levels. Intrathecal delivery, whether by a single lumbar bolus (Group 2), dosing at both the mid/lower and lumbar region with a Medtronic ASCENDA catheter (Group 3) or dosing at both the high cervical/cisterna magna and lumbar region with an Alcyone Pulsar catheter resulted in detectable levels of AAV5-FXN-026. The Alcyone Pulsar was able to be advanced to the C1 or cisterna magna level.

Example 15

Intracerebellar Tolerance and Biodistribution Study in Pigs

A direct injection into the dentate nucleus of pigs assessed the biodistribution of AAV5-FXN-026. Two treatment groups of three or six male Yucatan swine per group underwent a surgical procedure in which a single infusion of the test article was administered into the dentate nucleus of the cerebellum following a craniotomy of the skull. The treated animals were administered the test article on Day 0 at a dose level of $1\times10^{12}$ viral genomes (vg) (56 μL) (low-dose) or $3\times10^{12}$ vg (167 μL) (high-dose). One additional group of one male animal served as the control and did not receive test article nor underwent the surgical procedure; this animal was euthanized on Day 0 to provide control tissues. The animals were maintained for a 28±1 day or 60±4 days recovery period.

Observations for morbidity, mortality, injury, and the availability of food and water were conducted twice daily for all animals. Clinical observations were conducted daily on Days 1 to 7 and then weekly thereafter. Body weights were measured and recorded beginning in Week-1 and weekly during the study. Physical examinations were conducted pretest. Blood samples for clinical pathology evaluations were collected from all animals pretest. Blood samples were collected for possible future determination of the whole blood concentrations of the AAV5 antibody from all animals pretest and prior to each necropsy. Samples of cerebral spinal fluid (CSF) were collected for possible determination of CSF concentration of the AAV5 antibody pretest for Groups 2 and 3 and for all animals at each necropsy. At study termination, each animal was euthanized and a necropsy examination was conducted. Blood and selected tissues were collected for qPCR and frataxin protein analysis for all animals. Additionally, western blot analysis was conducted for the Group 1 animal and one of the Group 3 animals.

Figure 26:
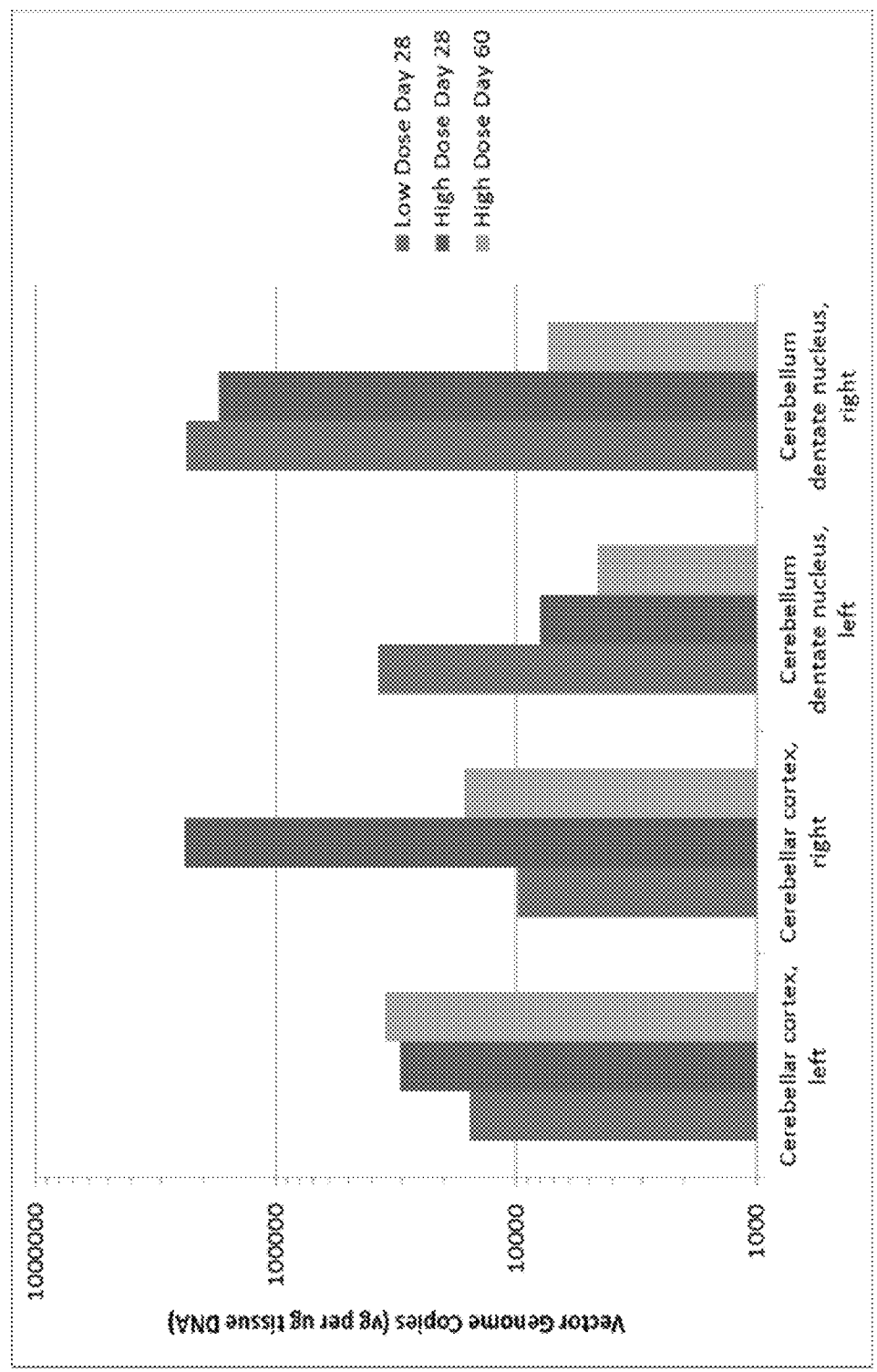
FIG. 26 is a chart showing distribution of rAAV5-FXN-026 following a single infusion into the cerebellum. Vector Genome Copies in the Cerebellum of male Yucatan swine Day 28 vs 60 (vg DNA/µg Tissue DNA).
Figure 27:
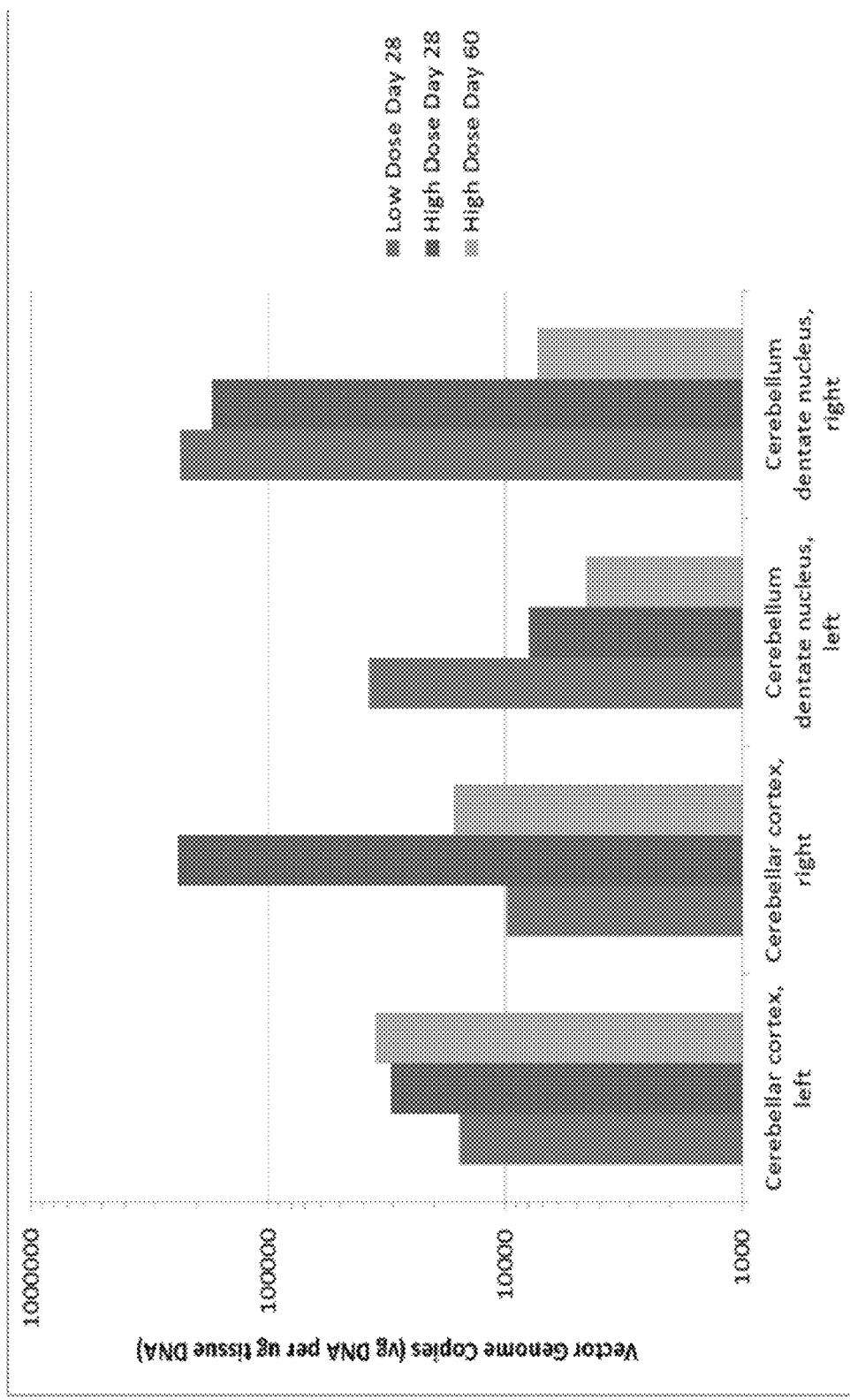
FIG. 27 is a chart showing distribution of rAAV5-FXN-026 following a single infusion into the cerebellum of male Yucatan swine. Vector Genome Copies in the Brain Day 28 vs 60 (vg DNA/µg Tissue DNA).
Figure 28:
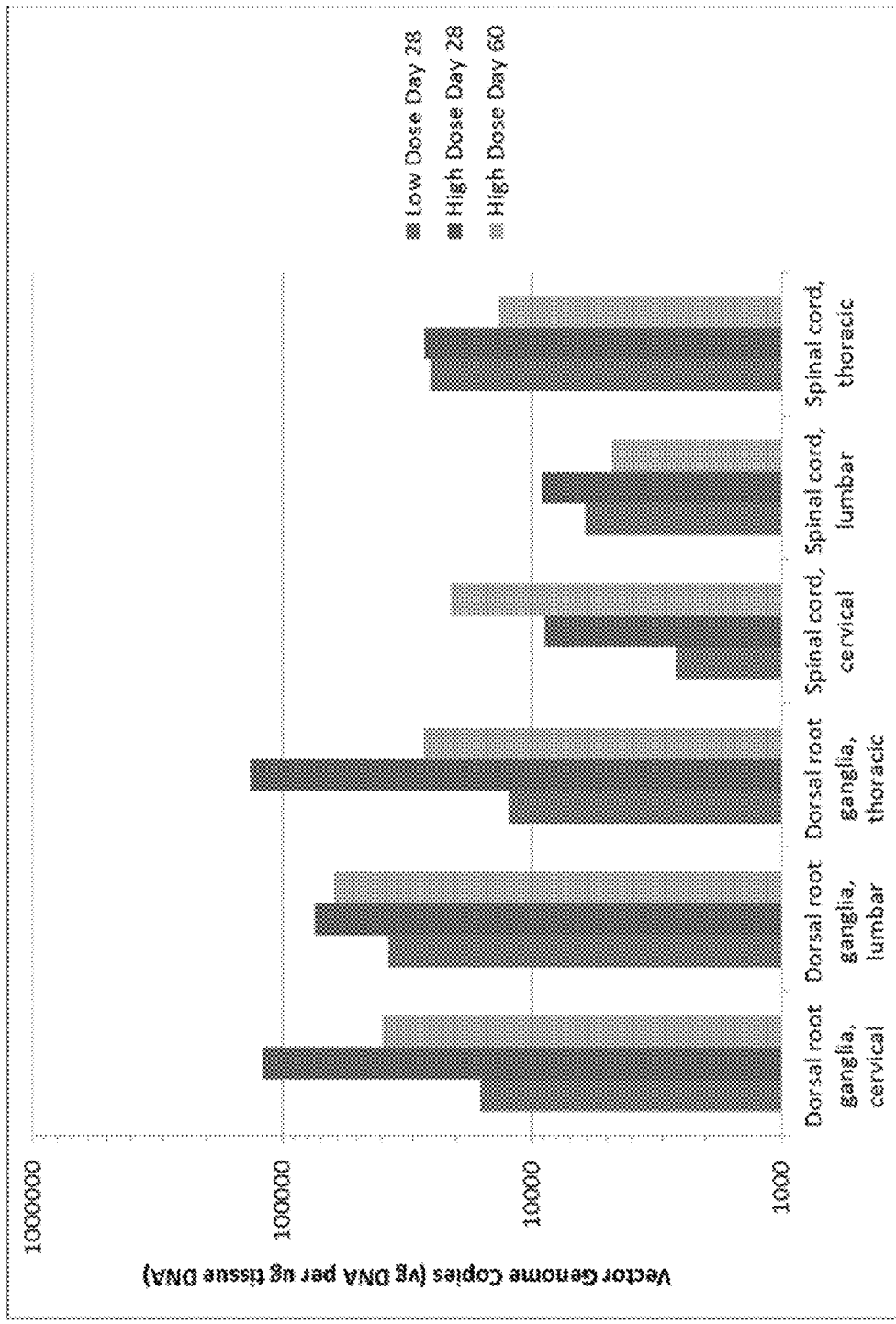
FIG. 28 is a chart showing distribution of rAAV5-FXN-026 following a single infusion into the cerebellum of male Yucatan swine. Vector Genome Copies in the Spinal Cord and DRG's Day 28 vs 60 (vg DNA/µg Tissue DNA).

The results of this study found extensive and persistent distribution of AAV5-FXN-026 throughout the brain and spinal cord following a single infusion into the cerebellum. Vector Genome Copies in the Cerebellum Day 28 vs 60 (vg DNA/μg Tissue DNA) are shown in FIG. 26. Vector Genome Copies in the Brain Day 28 vs 60 (vg DNA/μg Tissue DNA) are shown in FIG. 27. Vector Genome Copies in the Spinal Cord and DRG's Day 28 vs 60 (vg DNA/μg Tissue DNA are shown in FIG. 28. At 28 days, the highest levels of vector genome were found in the cerebellum, the motor cortex and the dorsal root ganglia. By 60 days, AAV5-FXN-026 was still present in these tissues, although the levels decreased relative to 28 days. These results demonstrate an affinity of the AAV5 capsid for the motor neuron tracts in the CNS. AAV5-FXN-026 levels in blood went from being undetectable in most animals on day 28 to detectable in all animals on Day 60, consistent with clearance of the vector from the CNS.

Figure 29:
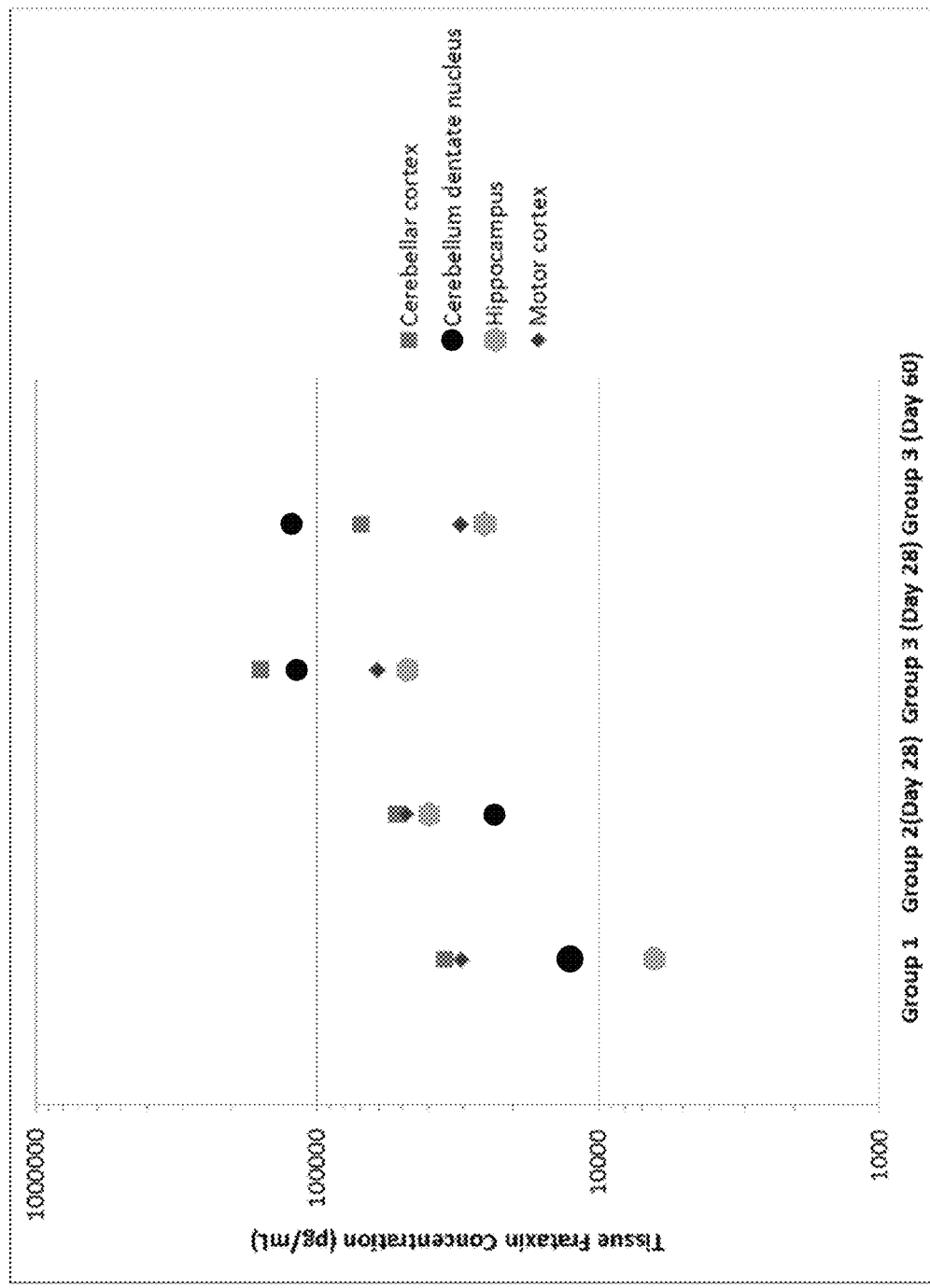
FIG. 29 is a chart showing expression of frataxin protein in tissue samples from the cerebellar cortex, the dentate nucleus, hippocampus, and the motor cortex of male Yucatan swine. Frataxin levels via ELISA.

Analyzing expression of frataxin protein, tissue samples from the cerebellar cortex, the dentate nucleus, hippocampus, and the motor cortex were collected. Frataxin levels via ELISA are shown in FIG. 29. Low dose animals showed variable increases over background control levels of frataxin. At Day-28 post-dose, frataxin levels increased between 1.5 (cerebellar cortex) and 6.4 (hippocampus) fold in the low dose tissues control tissues. High dose animals, at 28 and 60 days post-dose, showed frataxin levels increased approximately 2 (motor cortex) and 9 (dentate nucleus) fold over levels noted in the untreated, control tissues. These results demonstrate a persistent increase of frataxin protein production 60 days following treatment with the high dose of AAV5-FXN-026.

Overall this study demonstrated that following direct infusion of the test article at doses of $1 \times 10^{12}$ and $3 \times 10^{12}$ vg to the cerebellum, resulted in extensive and persistent biodistribution of the AAV5 capsid with an affinity for the motor neuron tracts.

Example 16

28-Day Intracerebellar Pilot Tolerance and Biodistribution Study in Primates

This study assessed the tolerance and biodistribution of an AAV5 human frataxin vector, AAV5-hFXN (026), following intracerebellar administration in cynomolgus monkeys (*Macaca facicularis*).

This study was based on the current International Council on Harmonization (ICH) Harmonized Tripartite Guidelines and generally accepted procedures for the testing of pharmaceutical compounds and in accordance with the United States Department of Agriculture's (USDA) Animal Welfare Act (9 CFR Parts 1, 2, and 3) and the Guide for the Care and Use of Laboratory Animals, Institute of Laboratory Animal Resources, National Academy Press, Washington, D.C., 2011. (See "Guidance on non-clinical safety studies for the conduct of human clinical trials and marketing authorization for pharmaceuticals," ICH M3(R2), 2009 June 11 and "Preclinical safety evaluation of biotechnology-derived pharmaceuticals," ICH S6 (R1), 1997 Jul. 16, (Addendum dated 12 Jun. 2011)).

Two treatment groups of three male cynomolgus monkeys per group underwent a surgical procedure in which a unilateral or bilateral infusion of the test article was administered into the dentate nucleus of the cerebellum following a craniotomy of the skull. The treated animals were administered the article on Day 1 at a dose level of $1.2 \times 10^{12}$ (30 µL) or $2.4 \times 10^{12}$ (30 µL/hemisphere) viral genomes (vg) per animal. One additional group of two male animals served as the control and received a bilateral infusion of the control article, phosphate buffered saline (PBS), pH 7.4. The animals were maintained until the Day 29±1 day necropsy.

Observations for morbidity, mortality, injury, and the availability of food and water were conducted twice daily for all animals. Clinical observations were conducted daily beginning on Day 1. Functional observational battery (FOB) assessments and neurological examinations were conducted prior to dosing (Day 1), 24 and 48 hours post-dose, and 7, 14, and 28 days post-dose. Body weights were measured and recorded weekly beginning on Day −1. Blood samples for clinical pathology evaluations were collected from all animals pretest and prior to necropsy. At study termination, necropsy examinations were performed and tissues were microscopically examined. Blood and selected tissues were collected for qPCR and frataxin protein enzyme-linked immunosorbent assay (ELISA) analysis.

The results demonstrated an affinity of the AAV5 capsid for the motor neuron tracts in the CNS. Upon analysis of brain tissue for expression frataxin protein by ELISA, at 28 days post-dose, frataxin levels increased between approximately 2 (cerebellar cortex) and 14 (dentate Nucleus) fold in test article treated animals over levels noted in the control animal tissues. Administration of the test article was associated with meningeal mononuclear cells infiltration within the meninges with occasional clustering around small meningeal vessels (perivascular). In addition, minimal perivascular mononuclear infiltrates were also noted within the brain parenchyma. Mononuclear cell infiltration is an expected non-adverse tissue response to the viral capsid.

In summary, the results of this study demonstrated that following direct infusion of the test article AAV5-hFXN (026) at doses of $1.2 \times 10^{12}$ vg and $2.4 \times 10^{12}$ vg to the cerebellum, extensive and persistent biodistribution of the AAV5 capsid with an affinity for the motor neuron tracts was observed. Frataxin expression was evident in the dentate nucleus and cortex regions of the cerebellum, where consistent increases in tissue frataxin levels relative to control tissues were observed. At 28 days, the highest levels of vector genome were found in the dentate nucleus and cerebellar cortex. These results demonstrated an affinity of the AAV5 capsid for the motor neuron tracts in the CNS. These results further demonstrated that intracerebellar injection of the test article at doses up to $2.4 \times 10^{12}$ vg are well tolerated and distributed well throughout the CNS.

Test Article and Control Preparation

The test article, AAV5-hFXN (026), was formulated at a concentration of $4 \times 10^{13}$ GC/mL and was warmed to between room temperature and body temperature prior to dosing. The control article was PBS, pH 7.4.

Animal Acquisition

A total of nine male cynomolgus monkeys (*Macaca fascicularis*) (approximately 3 years 10 months to 4 years 5 months of age at transfer)

Randomization, Assignment to Study, and Maintenance

Using a standard, by weight, randomization procedure, eight male animals (weighing 3.4 kg to 4.9 kg at randomization) were assigned to the study as identified in Table 8. Animals were maintained until the Day 29±1 day necropsy.

TABLE 8

Group Assignments

| Group Number | Route of Administration | Treatment | Dose (vg) | Number of Male Animals |
|---|---|---|---|---|
| 1 | Bilateral Intracerebellar Injection | PBS, pH 7.4 | 0 | 2 |
| 2 | Unilateral Intracerebellar Injection | AAV5-hFXN (026) | $1.2 \times 10^{12}$ | 3 |
| 3 | Bilateral Intracerebellar Injection | AAV5-hFXN (026) | $2.4 \times 10^{12}$ | 3 |

Surgical Procedure

The control and test article were administered via unilateral (Group 2) or bilateral (Groups 1 and 3) intracerebellar infusion into the area of the dentate nucleus. The treated groups (Groups 2 and 3) were administered the article on Day 1 at a dose level of $1.2 \times 10^{12}$ (30 µL) or $2.4 \times 10^{12}$ (30 µL/hemisphere) viral genomes (vg) per animal. The control group (Group 1) received a bilateral infusion of the control article, phosphate buffered saline (PBS), pH 7.4. The animals were maintained until the Day 29±1 day necropsy.

Following induction of anesthesia, the scalp was shaved and the animal was mounted in a magnetic resonance imaging (MRI) compatible stereotaxic frame (Kopf). A baseline MRI was given to establish targets and the animal was then transported to the surgical suite. An incision was made and the skin was reflected. A craniotomy was performed with a K wire and a cannulated drill bit at the appropriate injection site(s). Based on the stereotaxic coordinates, a blunt needle (22 gauge; 3.5 inch; B&D; reference number 405181) was inserted into the right (and left, for bilateral administration) cerebellum in the area of the dentate nucleus. Placement of the needle was confirmed via fluoroscopy and injection of contrast. The hub of the needle was flushed with sterile saline prior to attaching the dosing line. The control or test article (30 µL per infusion) was loaded into the microbore extension set with 30 µL of an air separation bubble. The remainder of the microbore extension was filled with sterile saline. The control or test article was infused at 10 µL/minute for 9 minutes to account for dead space in the needle. The needle was left in place for at least 2 minutes following completion of the infusion. Following removal of the needle, bone wax was placed into the drill hole and the incision was closed in standard fashion using any combination of absorbable sutures, skin staples, or skin glue.

Detailed Clinical Observations

A detailed clinical examination of each animal was performed daily during the study. On occasion, clinical observations were recorded at unscheduled intervals. The observations included, but were not limited to, evaluation of the skin, fur, eyes, ears, nose, oral cavity, thorax, abdomen, external genitalia, limbs and feet, respiratory and circulatory effects, autonomic effects such as salivation, and nervous system effects including tremors, convulsions, reactivity to handling, and unusual behavior.

Biodistribution Evaluations (Tissue, Blood, and Formulations)

Blood and tissue samples (approximately 100 to 200 mg per sample were collected from the brain (eight samples per animal), bone marrow, heart, liver, cervical lymph node, and kidney. For brain tissues, samples were taken from both right and left hemispheres, maintaining laterality. Samples were taken from the region of the cerebellar cortex (and included the Purkinje cell layer), cerebellum area of the dentate nucleus, hippocampus, and motor cortex. A section of each tissue was collected using an 8 mm punch biopsy and placed in labeled 2 mL microfuge tubes, snap-frozen in liquid nitrogen, and then placed on dry ice until stored frozen at −60 to −90° C. prior to qPCR analysis.

On each day of surgery, one sample (approximately 100 µL) of test article was injected through the needle and the sample was collected, placed on dry ice, and stored at −60 to −90° C. prior to qPCR analysis for test article concentration (vg/mL).

Tissue Collection for Frataxin Protein Analysis

Samples from the brain regions collected for qPCR analysis (at least 50 mg) were collected for frataxin protein ELISA analysis. Samples were taken from both right and left hemispheres maintaining laterality using a 5 mm circular punch.

Western Blot Analysis for Frataxin Localization in Mitochondria

Two additional cerebellar cortex samples (approximately 100 to 300 mg) were taken from one Group 1 (animal number 701) and all Group 3 animals for potential western blot analysis.

Neurologic examinations were performed by a staff veterinarian on Days 1, 2, 3, 7, 14, and 28. Cranial nerve response, peripheral sensation, and postural/behavior responses were assessed. Upon examination, all cranial nerve responses/reflexes and response to superficial pain were considered to be within normal limits. There were no test article-related effects observed among clinical pathology endpoints on Day 27 in cynomolgus monkeys administered AAV5-hFXN (026) via intracerebellar injection on Day 1 at doses of $1.2\times10^{12}$ vg or $2.4\times10^{12}$ vg.

There were no test article-related effects on hematology endpoints at either dose level. All apparent differences among hematology endpoints were not considered test article-related due to their negligible magnitude, lack of a dose-responsive pattern, and/or relation to expected values for biologic and procedure-related variation.

There were no test article-related effects on coagulation times (i.e. APTT and prothrombin times) or fibrinogen concentration at either dose level. All apparent differences among coagulation endpoints were not considered test article-related due to their negligible magnitude, lack of a dose-responsive pattern, and/or relation to expected values for biologic and procedure-related variation.

There were no test article-related effects on clinical chemistry endpoints at either dose level. All apparent differences among clinical chemistry endpoints were not considered test article-related due to their negligible magnitude, lack of a dose-responsive pattern, and/or relation to expected values for biologic and procedure-related variation.

There were no test article-related macroscopic findings; all tissues of all animals were considered within normal limits.

AAV5-hFXN (026)-related microscopic findings were limited to the presence of small numbers of mononuclear infiltrates in animals receiving $2.4\times10^{12}$ vg (bilateral injections) and $1.2\times10^{12}$ vg (unilateral injection, right). Mononuclear infiltrates were not observed in concurrent control animals.

In the majority of animals, the meningeal mononuclear cells were characterized by focal to locally extensive accumulations of small numbers of mononuclear cells within the meninges with occasional clustering around small meningeal vessels (perivascular). In addition, minimal perivascular mononuclear infiltrates were also noted within the brain parenchyma in a small number of animals (in the right cerebellar cortex and right motor cortex sections of one animal at $1.2\times10^{12}$ vg, and in the right cerebellar cortex or left motor cortex of single animals receiving $2.4\times10^{12}$ vg). The mononuclear infiltrates were associated with and/or exhibited increased IBA-1 staining/immunoreactivity. Mononuclear cell infiltration is an expected finding and is considered to be a non-adverse tissue response to the viral capsid.

Results and Discussion

Frataxin Protein Analysis

Figure 30:
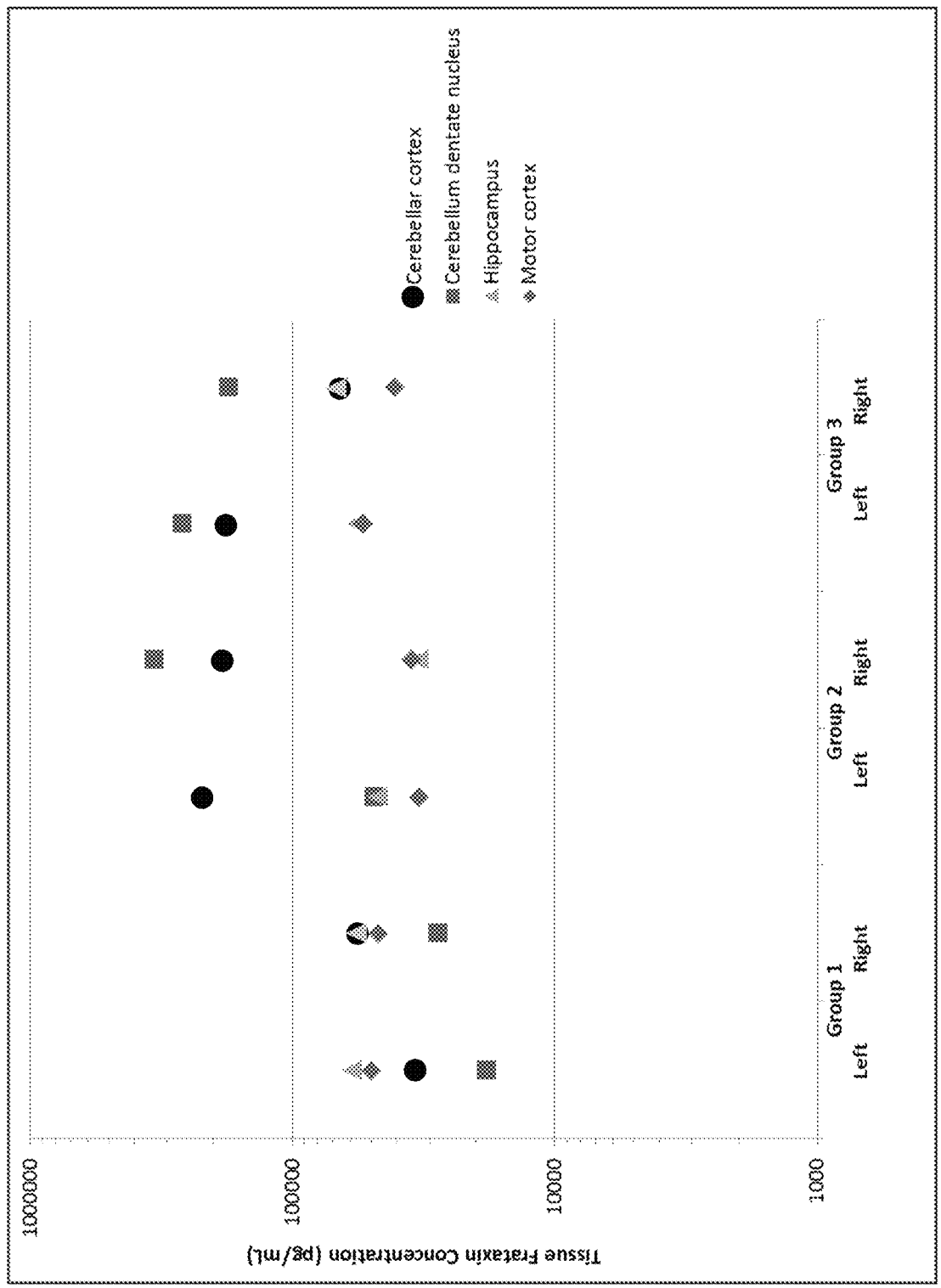
FIG. 30 is a chart showing biodistribution of an AAV5 human frataxin vector AAV5-hFXN (026) following intracerebellar administration to cynomolgus monkeys. Tissue samples from the cerebellar cortex, the dentate nucleus, hippocampus, and the motor cortex were analyzed for frataxin levels via ELISA.

Tissue samples from the cerebellar cortex, the dentate nucleus, hippocampus, and the motor cortex were collected and submitted for analysis of frataxin levels (FIG. 30) via ELISA. The results of this analysis found background levels of frataxin in the vehicle control animals. Frataxin levels are discussed as relative increases over background levels noted in the control animal. Animals in Group 2 received a single injection in the right cerebellar cortex and the animals in Group 3 received bilateral injections. At Day 28 post-dose, frataxin levels were noted to increase between 1.2 and 6.6 (cerebellar cortex) and 2.7 to 14.5 (dentate nucleus) fold over levels noted in the control tissues. At 28 days post-dose, frataxin levels were approximately equivalent in the hippocampus and motor cortex. These results, while variable, demonstrate a consistent increase over 28 days of frataxin protein production following treatment with the test article as either a single injection or bilateral injection in the cerebellar dentate nucleus and cerebellar cortex.

The invention claimed is:

1. A polynucleotide comprising a nucleic acid molecule encoding a human frataxin polypeptide having an amino acid sequence of SEQ ID NO:1, wherein the nucleic acid molecule is operably linked to a 5'UTR and a 3'UTR, wherein:
the 5'UTR is RPL6-5'Splice and the 3'UTR is a synthetic 3' regulatory element having a nucleic acid sequence of SEQ ID NO:7; or
the 5'UTR is 5U2 and the 3'UTR is a synthetic 3' regulatory element having a nucleic acid sequence of SEQ ID NO:7,
wherein the encoded human frataxin polypeptide is a functional frataxin protein.

2. The polynucleotide of claim 1, wherein said nucleic acid molecule encoding a human frataxin polypeptide is operably connected to a promoter.

3. The polynucleotide of claim 2 wherein said promoter is an inducible promoter.

4. The polynucleotide of claim 3 further comprising a gene switch that regulates expression from said inducible promoter.

5. The polynucleotide of claim 4, wherein said gene switch is an ecdysone receptor (EcR)-based gene switch.

6. The polynucleotide of claim 2 wherein said promoter is a CMV promoter, a UBC promoter, an EF1α promoter, a PGK1 promoter or a minimal frataxin promoter.

7. The polynucleotide of claim 2 wherein the promoter is a UBC promoter, the 5'UTR is 5U2, and the 3'UTR is a synthetic 3' regulatory element having a nucleic acid sequence of SEQ ID NO:7.

8. A viral vector comprising the polynucleotide of claim 1.

9. The viral vector of claim 8 wherein said vector is an adeno-associated viral vector.

10. The viral vector of claim 9 wherein said adeno-associated viral vector is AAV5.

11. A recombinant virion which comprises a viral vector, wherein said vector comprises a nucleic acid molecule encoding human frataxin operably linked to a 5'UTR, a 3'UTR, and a control element that directs transcription and/or translation, wherein:
the 5'UTR is RPL6-5'Splice and the 3'UTR is a synthetic 3' regulatory element having a nucleic acid sequence of SEQ ID NO:7; or
the 5'UTR is 5U2 and the 3'UTR is a synthetic 3' regulatory element having a nucleic acid sequence of SEQ ID NO:7.

12. The virion of claim 11 wherein said vector is an adeno-associated viral vector.

13. The virion of claim 12 wherein said adeno-associated viral vector is AAV5.

14. The virion of claim 11, wherein said nucleic acid encodes a protein with the amino acid sequence of SEQ ID NO:1.

15. The virion of claim 11, wherein said nucleic acid encodes a protein with the amino acid sequence of SEQ ID NO:1, the control element is a UBC promoter, the 5'UTR is 5U2, and the 3'UTR is a synthetic 3' regulatory element having a nucleic acid sequence of SEQ ID NO:7.

16. A composition comprising:
(a) a viral vector, wherein said vector comprises a nucleic acid molecule encoding human frataxin operably linked to a 5'UTR, a 3'UTR, and a control element that directs transcription and/or translation, wherein:
the 5'UTR is RPL6-5'Splice and the 3'UTR is a synthetic 3' regulatory element having a nucleic acid sequence of SEQ ID NO:7; or
the 5'UTR is 5U2 and the 3'UTR is a synthetic 3' regulatory element having a nucleic acid sequence of SEQ ID NO:7; and
(b) a pharmaceutically acceptable excipient.

17. The composition of claim 16 wherein said vector is an adeno-associated viral vector.

18. The composition of claim 17 wherein said adeno-associated viral vector is AAV5.

19. The composition of claim 16, wherein said nucleic acid encodes a protein with the amino acid sequence of SEQ ID NO:1.

20. The composition of claim 16, wherein said nucleic acid encodes a protein with the amino acid sequence of SEQ ID NO:1, the control element is a UBC promoter, the 5'UTR is 5U2, and the 3'UTR is a synthetic 3' regulatory element having a nucleic acid sequence of SEQ ID NO:7.

21. The polynucleotide of claim 2, wherein the promoter is a UBC promoter, the 5'UTR is RPL6-5' Splice, and the 3'UTR is a synthetic 3' regulatory element having a nucleic acid sequence of SEQ ID NO:7.

22. The virion of claim 11, wherein said nucleic acid encodes a protein with the amino acid sequence of SEQ ID NO:1, the control element is a UBC promoter, the 5'UTR is RPL6-5' Splice, and the 3'UTR is a synthetic 3' regulatory element having a nucleic acid sequence of SEQ ID NO:7.

23. The composition of claim 16, wherein said nucleic acid encodes a protein with the amino acid sequence of SEQ ID NO:1, the control element is a UBC promoter, the 5'UTR is RPL6-5' Splice, and the 3'UTR is a synthetic 3' regulatory element having a nucleic acid sequence of SEQ ID NO:7.

* * * * *

SEQUENCE LISTING

```
<160> NUMBER OF SEQ ID NOS: 20

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 2
<211> LENGTH: 633
<212> TYPE: DNA
<213> ORGANISM: Homo sapiens

<400> SEQUENCE: 2
atgtggactc tcgggcgccg cgcagtagcc ggcctcctgg cgtcacccag cccagcccag      60
gcccagaccc tcacccgggt cccgcggccg gcagagttgg ccccactctg cggccgccgt     120
ggcctgcgca ccgacatcga tgcgacctgc acgccccgcc gcgcaagttc gaaccaacgt     180
ggcctcaacc agatttggaa tgtcaaaaag cagagtgtct atttgatgaa tttgaggaaa     240
tctggaactt tgggccaccc aggctctcta gatgagacca cctatgaaag actagcagag     300
gaaacgctgg actctttagc agagtttttt gaagaccttg cagacaagcc atacacgttt     360
gaggactatg atgtctcctt tgggagtggt gtcttaactg tcaaactggg tggagatcta     420
```

```
ggaacctatg tgatcaacaa gcagacgcca acaagcaaa tctggctatc ttctccatcc      480
agtggaccta agcgttatga ctggactggg aaaaactggg tgtactccca cgacggcgtg      540
tccctccatg agctgctggc cgcagagctc actaaagcct taaaaaccaa actggacttg      600
tcttccttgg cctattccgg aaaagatgct tga                                  633

<210> SEQ ID NO 3
<211> LENGTH: 571
<212> TYPE: DNA
<213> ORGANISM: Homo sapiens

<400> SEQUENCE: 3
ggcctccgcg ccgggttttg gcgcctcccg cgggcgcccc cctcctcacg gcgagcgctg       60
ccacgtcaga cgaagggcgc agcgagcgtc ctgatccttc cgcccggacg ctcaggacag      120
cggcccgctg ctcataagac tcggccttag aaccccagta tcagcagaag acatttttag      180
gacgggactt gggtgactct agggcactgg ttttctttcc agagagcgga acaggcgagg      240
aaaagtagtc ccttctcggc gattctgcgg agggatctcc gtgggcggt gaacgccgat       300 gattatataa ggacgcgccg ggtgtggcac agctagttcc gtcgcagccg ggatttgggt      360
cgcggttctt gtttgtggat cgctgtgatc gtcacttggt gagtagcggg ctgctgggct      420
gggtacgtgc gctcggggtt ggcgagtgtg ttttgtgaag ttttttaggc accttttgaa      480
atgtaatcat ttgggtcaat atgtaatttt cagtgttaga ctagtaaatt gtccgctaaa      540
ttctggccgt ttttggcttt tttgttagac g                                    571

<210> SEQ ID NO 4
<211> LENGTH: 179
<212> TYPE: DNA
<213> ORGANISM: Homo sapiens

<400> SEQUENCE: 4
cgaagaaggt gagtaatctt aacatgctct ttttttttt ttttgctaat ccctttttgtg       60 tgctgatgtt aggatgacat ttacaacaaa tgtttgttcc tgacaggaaa aaccttgctg      120
ggtaccttcg ttgccggaca cttcttgtcc tctactttgg aaaaaaggaa ttgagagcc      179

<210> SEQ ID NO 5
<211> LENGTH: 627
<212> TYPE: DNA
<213> ORGANISM: Homo sapiens

<400> SEQUENCE: 5
tgatgggtgg catccctgtg acccctcccc agtgcctctc ctggccctgg aagttgccac       60
tccagtgccc accagccttg tcctaataaa attaagttgc atcattttgt ctgactaggt      120
gtccttctat aatattatgg ggtggagggg ggtggtatgg agcaaggggc aagttgggaa      180
gacaacctgt agggcctgcg gggtctattg ggaaccaagc tggagtgcag tggcacaatc      240
ttggctcact gcaatctccg cctcctgggt tcaagcgatt ctcctgcctc agcctcccga      300
gttgttggga ttccaggcat gcatgaccag gctcagctaa ttttttgtttt tttggtagag      360 acggggtttc accatattgg ccaggctggt ctccaactcc taatctcagg tgatctaccc      420
accttggcct cccaaattgc tgggattaca ggcgtgaacc actgctccct tccctgtcct      480
tctgatttta aaataactat accagcagga ggacgtccag acacagcata ggctacctgg      540
ccatgcccaa ccggtgggac atttgagttg cttgcttggc actgtcctct catgcgttgg      600
gtccactcag tagatgcctg ttgaatt                                         627
```

<210> SEQ ID NO 6
<211> LENGTH: 1711
<212> TYPE: DNA
<213> ORGANISM: Gallus gallus

<400> SEQUENCE: 6

```
attgattatt gactagttat taatagtaat caattacggg gtcattagtt catagcccat      60
atatggagtt ccgcgttaca taacttacgg taaatggccc gcctggctga ccgcccaacg     120
accccgccc attgacgtca ataatgacgt atgttcccat agtaacgcca atagggactt     180
tccattgacg tcaatgggtg gactatttac ggtaaactgc ccacttggca gtacatcaag     240
tgtatcatat gccaagtacg cccctattg acgtcaatga cggtaaatgg cccgcctggc     300
attatgccca gtacatgacc ttatgggact ttcctacttg gcagtacatc tacgtattag     360
tcatcgctat taccatgggt cgaggtgagc ccacgttct gcttcactct ccccatctcc     420
cccctccc cacccccaat tttgtattta tttatttttt aattattttg tgcagcgatg     480
ggggcggggg ggggggggc gcgcgccagg cggggcgggg cggggcgagg ggcggggcgg     540
ggcgaggcg agaggtgcgg cggcagccaa tcagagcggc gcgctccgaa agtttcctt     600
tatggcgagg cggcggcggc ggcggcccta taaaaagcga agcgcgcggc gggcgggagt     660
cgctgcgttg ccttcgcccc gtgccccgct ccgcgccgcc tcgcgccgcc cgccccggct     720
ctgactgacc gcgttactcc cacaggtgag cgggcgggac ggcccttctc ctccgggctg     780
taattagcgc ttggtttaat gacggctcgt ttcttttctg tggctgcgtg aaagccttaa     840
agggctccgg gagggccctt tgtgcggggg ggagcggctc gggggtgcg tgcgtgtgtg     900
tgtgcgtggg gagcgccgcg tgcggcccgc gctgcccggc ggctgtgagc gctgcgggcg     960
cggcgcgggg ctttgtgcgc tccgcgtgtg cgcgagggga gcgcggccgg gggcggtgcc    1020
ccgcggtgcg ggggggctgc gagggaaca aaggctgcgt gcggggtgtg tgcgtggggg    1080
ggtgagcagg gggtgtgggc gcggcggtcg ggctgtaacc ccccctgca ccccctccc    1140
cgagttgctg agcacggccc ggcttcgggt gcggggctcc gtgcggggcg tggcgcgggg    1200
ctcgccgtgc cgggcggggg gtggcggcag gtgggggtgc cgggcggggc ggggccgcct    1260
cgggccgggg agggctcggg ggaggggcgc ggcggccccg gagcgccggc ggctgtcgag    1320
gcgcggcgag ccgcagccat tgcctttat ggtaatcgtg cgagagggcg cagggacttc    1380
ctttgtccca aatctggcgg agccgaaatc tgggaggcgc cgccgcaccc cctctagcgg    1440
gcgcgggcga agcggtgcgg cgccggcagg aaggaaatgg gcggggaggg ccttcgtgcg    1500
tcgccgcgcc gccgtcccct tctccatctc cagcctcggg gctgccgcag ggggacggct    1560
gccttcgggg gggacgggc agggcgggt tcggcttctg gcgtgtgacc ggcggctcta    1620
gagcctctgc taaccatgtt catgccttct tctttttcct acagctcctg gcaacgtgc    1680
tggttgttgt gctgtctcat cattttggca a                                   1711
```

<210> SEQ ID NO 7
<211> LENGTH: 370
<212> TYPE: DNA
<213> ORGANISM: Artificial Sequence
<220> FEATURE:
<223> OTHER INFORMATION: Synthetic DNA

<400> SEQUENCE: 7

```
tacgctcctc tactctttga cacatcactg gcctataata aatgggttaa tttatgtaac      60
```

-continued

```
aaaattgcct tggcttgtta acttattag acattctgat gtttgcattg tgtaaatact      120
gttgtattgg aaaagcgtgc caagatggat tattgtaatt cagtgtcttt tttagtaggc      180
atagtgttac catcaaccac cttaacttca tttttcttat tcaataccta ggtaggtaga      240
tgctagattc tggaaataaa atatgagtct caagtggtcc ttgtcctctc tcccagtcaa      300
attctgaatc tagttggcaa gattctgaaa tcaaggcata taatcagtaa taagtgatga      360
tagaagggta                                                             370
```

<210> SEQ ID NO 8
<211> LENGTH: 132
<212> TYPE: DNA
<213> ORGANISM: Simian virus 40

<400> SEQUENCE: 8

```
aacttgttta ttgcagctta taatggttac aaataaagca atagcatcac aaatttcaca      60
aataaagcat ttttttcact gcattctagt tgtggtttgt ccaaactcat caatgtatct      120
tatcatgtct gg                                                          132
```

<210> SEQ ID NO 9
<211> LENGTH: 221
<212> TYPE: DNA
<213> ORGANISM: Simian virus 40

<400> SEQUENCE: 9

```
agacatgata agatacattg atgagtttgg acaaaccaca acaagaatgc agtgaaaaaa      60
atgctttatt tgtgaaattt gtgatgctat tgctttattt gtaaccatta taagctgcaa      120
taaacaagtt aacaacaaca attgcattca ttttatgttt caggttcagg gggagatgtg      180
ggaggttttt taaagcaagt aaaacctcta caaatgtggt a                          221
```

<210> SEQ ID NO 10
<211> LENGTH: 878
<212> TYPE: PRT
<213> ORGANISM: Drosophila melanogaster

<400> SEQUENCE: 10

Met Lys Arg Arg Trp Ser Asn Asn Gly Gly Phe Met Arg Leu Pro Glu
1               5                   10                  15

Glu Ser Ser Ser Glu Val Thr Ser Ser Ser Asn Gly Leu Val Leu Pro
            20                  25                  30

Ser Gly Val Asn Met Ser Pro Ser Ser Leu Asp Ser His Asp Tyr Cys
        35                  40                  45

Asp Gln Asp Leu Trp Leu Cys Gly Asn Glu Ser Gly Ser Phe Gly Gly
    50                  55                  60

Ser Asn Gly His Gly Leu Ser Gln Gln Gln Ser Val Ile Thr Leu
65                  70                  75                  80

Ala Met His Gly Cys Ser Ser Thr Leu Pro Ala Gln Thr Thr Ile Ile
                85                  90                  95

Pro Ile Asn Gly Asn Ala Asn Gly Asn Gly Ser Thr Asn Gly Gln
            100                 105                 110

Tyr Val Pro Gly Ala Thr Asn Leu Gly Ala Leu Ala Asn Gly Met Leu
        115                 120                 125

Asn Gly Gly Phe Asn Gly Met Gln Gln Gln Ile Gln Asn Gly His Gly
    130                 135                 140

Leu Ile Asn Ser Thr Thr Pro Ser Thr Pro Thr Thr Pro Leu His Leu
145                 150                 155                 160

```
Gln Gln Asn Leu Gly Gly Ala Gly Gly Gly Ile Gly Gly Met Gly
            165                 170                 175

Ile Leu His His Ala Asn Gly Thr Pro Asn Gly Leu Ile Gly Val Val
            180                 185                 190

Gly Gly Gly Gly Gly Val Gly Leu Gly Val Gly Gly Gly Val Gly
            195                 200                 205

Gly Leu Gly Met Gln His Thr Pro Arg Ser Asp Ser Val Asn Ser Ile
            210                 215                 220

Ser Ser Gly Arg Asp Asp Leu Ser Pro Ser Ser Ser Leu Asn Gly Tyr
225                 230                 235                 240

Ser Ala Asn Glu Ser Cys Asp Ala Lys Lys Ser Lys Lys Gly Pro Ala
            245                 250                 255

Pro Arg Val Gln Glu Glu Leu Cys Leu Val Cys Gly Asp Arg Ala Ser
            260                 265                 270

Gly Tyr His Tyr Asn Ala Leu Thr Cys Glu Gly Cys Lys Gly Phe Phe
            275                 280                 285

Arg Arg Ser Val Thr Lys Ser Ala Val Tyr Cys Cys Lys Phe Gly Arg
            290                 295                 300

Ala Cys Glu Met Asp Met Tyr Met Arg Arg Lys Cys Gln Glu Cys Arg
305                 310                 315                 320

Leu Lys Lys Cys Leu Ala Val Gly Met Arg Pro Glu Cys Val Val Pro
            325                 330                 335

Glu Asn Gln Cys Ala Met Lys Arg Arg Glu Lys Lys Ala Gln Lys Glu
            340                 345                 350

Lys Asp Lys Met Thr Thr Ser Pro Ser Ser Gln His Gly Gly Asn Gly
            355                 360                 365

Ser Leu Ala Ser Gly Gly Gly Gln Asp Phe Val Lys Lys Glu Ile Leu
            370                 375                 380

Asp Leu Met Thr Cys Glu Pro Pro Gln His Ala Thr Ile Pro Leu Leu
385                 390                 395                 400

Pro Asp Glu Ile Leu Ala Lys Cys Gln Ala Arg Asn Ile Pro Ser Leu
            405                 410                 415

Thr Tyr Asn Gln Leu Ala Val Ile Tyr Lys Leu Ile Trp Tyr Gln Asp
            420                 425                 430

Gly Tyr Glu Gln Pro Ser Glu Glu Asp Leu Arg Arg Ile Met Ser Gln
            435                 440                 445

Pro Asp Glu Asn Glu Ser Gln Thr Asp Val Ser Phe Arg His Ile Thr
            450                 455                 460

Glu Ile Thr Ile Leu Thr Val Gln Leu Ile Val Glu Phe Ala Lys Gly
465                 470                 475                 480

Leu Pro Ala Phe Thr Lys Ile Pro Gln Glu Asp Gln Ile Thr Leu Leu
            485                 490                 495

Lys Ala Cys Ser Ser Glu Val Met Met Leu Arg Met Ala Arg Arg Tyr
            500                 505                 510

Asp His Ser Ser Asp Ser Ile Phe Phe Ala Asn Asn Arg Ser Tyr Thr
            515                 520                 525

Arg Asp Ser Tyr Lys Met Ala Gly Met Ala Asp Asn Ile Glu Asp Leu
            530                 535                 540

Leu His Phe Cys Arg Gln Met Phe Ser Met Lys Val Asp Asn Val Glu
545                 550                 555                 560

Tyr Ala Leu Leu Thr Ala Ile Val Ile Phe Ser Asp Arg Pro Gly Leu
            565                 570                 575
```

-continued

```
Glu Lys Ala Gln Leu Val Glu Ala Ile Gln Ser Tyr Tyr Ile Asp Thr
                580                 585                 590

Leu Arg Ile Tyr Ile Leu Asn Arg His Cys Gly Asp Ser Met Ser Leu
            595                 600                 605

Val Phe Tyr Ala Lys Leu Leu Ser Ile Leu Thr Glu Leu Arg Thr Leu
        610                 615                 620

Gly Asn Gln Asn Ala Glu Met Cys Phe Ser Leu Lys Leu Lys Asn Arg
625                 630                 635                 640

Lys Leu Pro Lys Phe Leu Glu Glu Ile Trp Asp Val His Ala Ile Pro
                645                 650                 655

Pro Ser Val Gln Ser His Leu Gln Ile Thr Gln Glu Glu Asn Glu Arg
            660                 665                 670

Leu Glu Arg Ala Glu Arg Met Arg Ala Ser Val Gly Gly Ala Ile Thr
        675                 680                 685

Ala Gly Ile Asp Cys Asp Ser Ala Ser Thr Ser Ala Ala Ala Ala Ala
690                 695                 700

Ala Gln His Gln Pro Gln Pro Gln Pro Gln Pro Ser Ser Leu
705                 710                 715                 720

Thr Gln Asn Asp Ser Gln His Gln Thr Gln Pro Gln Leu Gln Pro Gln
            725                 730                 735

Leu Pro Pro Gln Leu Gln Gly Gln Leu Gln Pro Gln Leu Gln Pro Gln
        740                 745                 750

Leu Gln Thr Gln Leu Gln Pro Gln Ile Gln Pro Gln Pro Gln Leu Leu
        755                 760                 765

Pro Val Ser Ala Pro Val Pro Ala Ser Val Thr Ala Pro Gly Ser Leu
        770                 775                 780

Ser Ala Val Ser Thr Ser Ser Glu Tyr Met Gly Gly Ser Ala Ala Ile
785                 790                 795                 800

Gly Pro Ile Thr Pro Ala Thr Thr Ser Ser Ile Thr Ala Ala Val Thr
                805                 810                 815

Ala Ser Ser Thr Thr Ser Ala Val Pro Met Gly Asn Gly Val Gly Val
            820                 825                 830

Gly Val Gly Val Gly Gly Asn Val Ser Met Tyr Ala Asn Ala Gln Thr
        835                 840                 845

Ala Met Ala Leu Met Gly Val Ala Leu His Ser His Gln Glu Gln Leu
        850                 855                 860

Ile Gly Gly Val Ala Val Lys Ser Glu His Ser Thr Thr Ala
865                 870                 875

<210> SEQ ID NO 11
<211> LENGTH: 240
<212> TYPE: PRT
<213> ORGANISM: Choristoneura fumiferana

<400> SEQUENCE: 11

Leu Thr Ala Asn Gln Gln Phe Leu Ile Ala Arg Leu Ile Trp Tyr Gln
1               5                   10                  15

Asp Gly Tyr Glu Gln Pro Ser Asp Glu Asp Leu Lys Arg Ile Thr Gln
            20                  25                  30

Thr Trp Gln Gln Ala Asp Asp Glu Asn

```
Ile Thr Leu Leu Lys Ala Cys Ser Ser Glu Val Met Met Leu Arg Val
                85                  90                  95

Ala Arg Arg Tyr Asp Ala Ala Ser Asp Ser Val Leu Phe Ala Asn Asn
            100                 105                 110

Gln Ala Tyr Thr Arg Asp Asn Tyr Arg Lys Ala Gly Met Ala Tyr Val
        115                 120                 125

Ile Glu Asp Leu Leu His Phe Cys Arg Cys Met Tyr Ser Met Ala Leu
    130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205

Leu Arg Thr Leu Gly Met Gln Asn Ser Asn Met Cys Ile Ser Leu Lys
    210                 215                 220

Leu Lys Asn Arg Lys Leu Pro Pro Phe Leu Glu Glu Ile Trp Asp Val
225                 230                 235                 240
```

<210> SEQ ID NO 12
<211> LENGTH: 240
<212> TYPE: PRT
<213> ORGANISM: Choristoneura fumiferana

<400> SEQUENCE: 12

```
Leu Thr Ala Asn Gln Gln Phe Leu Ile Ala Arg Leu Ile Trp Tyr Gln
1               5                   10                  15

Asp Gly Tyr Glu Gln Pro Ser Asp Glu Asp Leu Lys Arg Ile Thr Gln
                20                  25                  30

Thr Trp Gln Gln Ala Asp Asp Glu Asn Glu Ser Asp Thr Pro Phe
            35                  40                  45

Arg Gln Ile Thr Glu Met Thr Ile Leu Thr Val Gln Leu Ile Val Glu
50                  55                  60

Phe Ala Lys Gly Leu Pro Gly Phe Ala Lys Ile Ser Gln Pro Asp Gln
65                  70                  75                  80

Ile Thr Leu Leu Lys Ala Cys Ser Ser Glu Val Met Met Leu Arg Val
                85                  90                  95

Ala Arg Arg Tyr Asp Ala Ala Ser Asp Ser Ile Leu Phe Ala Asn Asn
            100                 105                 110

Gln Ala Tyr Thr Arg Asp Asn Tyr Arg Lys Ala Gly Met Ala Glu Val
        115                 120                 125

Ile Glu Asp Leu Leu His Phe Cys Arg Cys Met Tyr Ser Met Ala Leu
    130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205

Leu Arg Thr Leu Gly Met Gln Asn Ser Asn Met Cys Ile Ser Leu Lys
```

210                 215                 220
Leu Lys Asn Arg Lys Leu Pro Pro Phe Leu Glu Glu Ile Trp Asp Val
225                 230                 235                 240

<210> SEQ ID NO 13
<211> LENGTH: 598
<212> TYPE: DNA
<213> ORGANISM: Human cytomegalovirus

<400> SEQUENCE: 13
gcattagtta ttaatagtaa tcaattacgg ggtcattagt tcatagccca tatatggagt     60
tccgcgttac ataacttacg gtaaatggcc cgcctggttg accgcccaac gaccccgcc    120 cattgacgtc aataatgacg tatgttccca tagtaacgcc aatagggact ttccattgac   180
gtcaatgggt ggagtattta cggtaaactg cccacttggt agtacatcaa gtgtatcata   240
cgccaagtac gccccctatt gacgtcaatg acggtaaatg gcccgcctgg tattatgccc   300
agtacatgac cttatgggac tttcctactt ggcagtacat ctgcgtatta gtcatcgcta   360
ttaccatggt gatgcggttt tggcagtaca tcaatgggcg tggatagcgg tttgactcac   420
ggggatttcc aagtctccac cccattgacg tcaatgggag tttgttttgg caccaaaatc   480
aacgggactt tccaaaatgt cgtaacaact ccgccccatt gacgcaaatg ggcggtaggc   540
gtgtacggtg gaggtctat ataagcagag ctggtttagt gaaccgtcag atccgcta     598

<210> SEQ ID NO 14
<211> LENGTH: 226
<212> TYPE: DNA
<213> ORGANISM: Homo sapiens

<400> SEQUENCE: 14
ataagagacc acaagcgacc cgcagggcca gacgttcttc gccgagagtc gtcggggttt     60
cctgcttcaa cagtgcttgg acggaacccg gcgctcgttc cccacccgg ccagccgccc    120 atagccagcc ctccgtcacc tcttcaccgc acctcggac tgcccaagg ccccgccgc      180 cgctccagcg ccgcgcagcc accgccgccg ccgccgcctc ccctta                   226

<210> SEQ ID NO 15
<211> LENGTH: 102
<212> TYPE: DNA
<213> ORGANISM: Homo sapiens

<400> SEQUENCE: 15
aaattgagcc cgcagcctcc cgcttcgctc tctgctcctc ctgttcgaca gtcagccgca     60
tcttcttttg cgtcgccagc cgagccacat cgctcagaca cc                      102

<210> SEQ ID NO 16
<211> LENGTH: 107
<212> TYPE: DNA
<213> ORGANISM: Homo sapiens

<400> SEQUENCE: 16
cagccgctaa atccaaggta agggaagagg accacggacc attatgtctt aaccttaatt     60
ggcattctct tactgttgat gcatttgtgt ccttgtaggt tgaaaag                 107

<210> SEQ ID NO 17
<211> LENGTH: 1400
<212> TYPE: DNA
<213> ORGANISM: Homo sapiens

<400> SEQUENCE: 17

```
ttgcagaccc tgcattctca tgcagcagag acaccaccc agactgataa tctggctcaa      60
ctagctccac gatcccaccc aggaagaact cgcaagaact cacttcgacc ccgtgattta    120
atcttcatcc cgaccaacta gcactcccca ctttccgaac ccattcctgc caaattatcc    180
ttaaaaactc tgattccaga atgctcaggg agactgattt gagtgataat gaaactctgg    240
tctcccgcac agcgctcagc gtgaattatt ctttcgccat tgcaattccc gtcttcataa    300
atcagctctg tctaggcagc ggacaaggtg aacccattgg gcggttacac tttcgttttc    360
aatacatctc tgcttttatt gcttcattct ttctttgctt tgtgcatttc gtccagttct    420
tagttcaaga cgctaagaac ttggacaccc tccacgggta acaggactac aggtgcccgc    480
caccacgtct agctaatttt ttgtattttt agtagagatg gggttttgct atgttgctca    540
ggctggtctc gaaccactgg gctcaagcaa tctgccgggc ttggcctccc aaagtgccgg    600
gattaaaggc gtgagccacc cgcgcctggcc cactaaactt ctctgtgcat cagttatttc    660
atttgcctaa tgaggataac agtagtcact actgcgtttt gtgagcgttg gttaatatat    720
gaaaaatgcc acgtgtttgc cattagcatc aatcatgcca taaccagaaa aattacattg    780
cattttttat tttaaaaaag gtgggggcca gagtggacct gggcctcttc caacttctga    840
gaggtctcta ttactaagta agccttaaca agcacaattc catgaaggga gctaggaaac    900
caggattttc caaaaggagg tggcatttgc attgatcctg gtaggcagc ctccaattcg     960
acggggttgg ggttgcgcct tttccaaggc agccctgggt ttgcgcaggg acgcggctgc   1020
tctgggcgtg gttccgggaa acgcagcggc gccgaccctg ggtctcgcac attcttcacg   1080
tccgttcgca gcgtcacccg gatcttcgcc gctacccttg tgggccccc ggcgacgctt    1140
cctgctccgc ccctaagtcg ggaaggttcc ttgcggttcg cggcgtgccg gacgtgacaa   1200
acggaagccg cacgtctgac tagaaccctc gcagacggac agcgccaggg agcaatggca   1260
gcgcgccgac cgcgatgggc tgtggccaat agcggctgct cagcaggccg cgccgagagc   1320
agcggccggg aagggggcggt gcgggaggcg gggtgtgggg cggtagtgtg ggccctgttc   1380
ctgcccgcgc ggtgttccgc                                              1400
```

<210> SEQ ID NO 18
<211> LENGTH: 244
<212> TYPE: DNA
<213> ORGANISM: Homo sapiens

<400> SEQUENCE: 18

```
gagcgtgcgt gaggctccgg tgcccgtcag tgggcagagc gcacatcgcc cacagtcccc      60
gagaagttgg ggggagggggg tcggcgattg aaccggtgcc tagagaaggt ggcgcggggt    120
aaactgggaa agtgatgtcg tgtactggct ccgccttttt cccgagggtg ggggagaacc    180
gtatataagt gcagtagtcg ccgtgaacgt tcttttttcgc aacgggtttg ccgccagaac    240
acag                                                                 244
```

<210> SEQ ID NO 19
<211> LENGTH: 4691
<212> TYPE: DNA
<213> ORGANISM: Artificial Sequence
<220> FEATURE:
<223> OTHER INFORMATION: Expression Vector

<400> SEQUENCE: 19

```
cctgcaggca gctgcgcgct cgctcgctca ctgaggccgc ccgggcaaag cccgggcgtc      60
```

```
gggcgacctt tggtcgcccg gcctcagtga gcgagcgagc gcgcagagag ggagtggcca    120
actccatcac taggggttcc ttaactataa cggtcctaag gtagcgagcg atcgcttaat    180
taaggccggc cggcctccgc gccgggtttt ggcgcctccc gcgggcgccc ccctcctcac    240
ggcgagcgct gccacgtcag acgaagggcg cagcgagcgt cctgatcctt ccgcccggac    300
gctcaggaca gcggcccgct gctcataaga ctcggcctta aaccccagt atcagcagaa     360
ggacatttta ggacgggact tgggtgactc tagggcactg gttttctttc cagagagcgg    420
aacaggcgag gaaaagtagt cccttctcgg cgattctgcg gagggatctc cgtggggcgg    480
tgaacgccga tgattatata aggacgcgcc gggtgtggca cagctagttc cgtcgcagcc    540
gggatttggg tcgcggttct tgtttgtgga tcgctgtgat cgtcacttgg tgagtagcgg    600
gctgctgggc tgggtacgtg cgctcggggt tggcgagtgt gttttgtgaa gttttttagg    660
cacctttga aatgtaatca tttgggtcaa tatgtaattt tcagtgttag actagtaaat     720
tgtccgctaa attctggccg tttttggctt ttttgttaga cgcctgcagg ggcgcgccac    780
gcgtcgaaga aggtgagtaa tcttaacatg ctcttttttt ttttttttgc taatcccttt    840
tgtgtgctga tgttaggatg acatttacaa caaatgtttg ttcctgacag gaaaaacctt    900
gctgggtacc ttcgttgccg gacacttctt gtcctctact ttggaaaaaa ggaattgaga    960
gccgctagcg ccaccatgtg gactctcggg cgccgcgcag tagccggcct cctggcgtca   1020
cccagcccag cccaggccca gaccctcacc cgggtcccgc ggccggcaga gttggcccca   1080
ctctgcggcc gccgtggcct cgcaccgac atcgatgcga cctgcacgcc ccgccgcgca    1140
agttcgaacc aacgtggcct caaccagatt tggaatgtca aaaagcagag tgtctatttg   1200
atgaatttga ggaaatctgg aactttgggc cacccaggct ctctagatga gaccaccctat 1260
gaaagactag cagaggaaac gctggactct ttagcagagt ttttttgaaga ccttgcagac  1320
aagccataca cgtttgagga ctatgatgtc tcctttggga gtggtgtctt aactgtcaaa   1380
ctgggtggag atctaggaac ctatgtgatc aacaagcaga cgccaaacaa gcaaatctgg   1440
ctatcttctc catccagtgg acctaagcgt tatgactgga ctgggaaaaa ctgggtgtac   1500
tcccacgacg gcgtgtccct ccatgagctg ctggccgcag agctcactaa agccttaaaa   1560
accaaactgg acttgtcttc cttggcctat tccggaaaag atgcttgaat cgattacgta   1620
gcggccgcgt cgactgatgg gtggcatccc tgtgaccct ccccagtgcc tctcctggcc    1680
ctggaagttg ccactccagt gcccaccagc cttgtcctaa taaaattaag ttgcatcatt   1740
ttgtctgact aggtgtcctt ctataatatt atggggtgga gggggtggt atggagcaag    1800
gggcaagttg ggaagacaac ctgtagggcc tgcgggtct attgggaacc aagctggagt    1860
gcagtggcac aatcttggct cactgcaatc tccgcctcct gggttcaagc gattctcctg   1920
cctcagcctc ccgagttgtt gggattccag gcatgcatga ccaggctcag ctaatttttg   1980
tttttttggt agagacgggg tttcaccata ttggccaggc tggtctccaa ctcctaatct   2040
caggtgatct acccaccttg gcctcccaaa ttgctgggat tacaggcgtg aaccactgct   2100
cccttccctg tccttctgat tttaaaataa ctataccagc aggaggacgt ccagacacag   2160
cataggctac ctggccatgc caaccggtg ggacatttga gttgcttgct tggcactgtc    2220
ctctcatgcg ttgggtccac tcagtagatg cctgttgaat tatttaaatc ggtccgcgta   2280
cgttatggct atagaatgcc ccatcttaga ttgtaggtga cttgagaggt ctaagtcctt   2340
ctataggata tccttctagg taggtataat actagtctag gttaaactag ctagggagt    2400
```

```
cagagagcat tcgcaaagtt tacctagtct acaagtctct cccactatcc ttgagcctac    2460
cctaggctag atcctaggaa tcatcccatg tcgtcattct agctcatagc actctcacta    2520
tcctactagc taggccatct tcctaggaaa agtataagat cctagtttga tatagcatca    2580
atgtagctag tgggaaggat acggatgacc tcatagcttg cagctttata aacttctccc    2640
tcccatacca cctacctagg tgctatgagg tgactttaga atcaccctct aggaggtaga    2700
ctatgatagt ccttccttct agtatcaaga tatcatctag ctacaagtta tcgaaggttg    2760
acctaacctt atagcaatat tttgacctac ctgagagctt tagagcccta gtttgagagt    2820
ctatgtccat ctagggccta cctaccttac ctactacatg atgtagctct atcctagagc    2880
cctctcatgg ttatgagttg cctgcaaggc tagaatctag gaagatcctt ccatcatatc    2940
cttgtagcta ttttctacaa tcgagaagag gtcctcctac ttctaacttt tgccattgcc    3000
ccatctagct acaaggttat gagagagagt ataagtcatg ccataatacc taggtagaaa    3060
ttctcaccta tcctatttct ttctagcttg cagtgctact agcatggggt gagatcttga    3120
gtctagcctt ttgtcctagg gacttttaga gcctaagact ctagagtgcc ccgatctaat    3180
atccttctat aacttcctac cagtctctta tagcctttga ccctatttct accacctact    3240
tcgcatggtc tttctttacc ttaccataag actgccttag actacctagg gagagactta    3300
aggccatgct ataagctata ggtctaggct atatcctttc accatatagc atgatcatag    3360
gcgcaaagta gaaaggactc taggatagag actctataga tgagcttgat actgactttg    3420
tcgttacttt gaccctagta gctcatacta tcatgatggt gactcttgag ccagtatgat    3480
cttcgtccta agtcccaccc catctttgcc acgctataga tctgctctaa gctatagacc    3540
atccttgacc taccttagag tataggtcaa actctagact agactttgta ggagggctat    3600
agcctttgcc ccatctcacc tcactctcta atatttctat gagcttttag gtaaagtatc    3660
ttctaaagct atcctagggt cctttttactt cagcaagtgc aaggagtcaa atctcttact    3720
ttaggcctag caatcttagg tcgcaagacc ctctatagct ctcttctagc tcatagcatg    3780
ggataacctt cagtcaaaag tgctagactt gctagagatg ctctagatag tttgacctaa    3840
ggtaggttag aaagtcactt tcgtcctttt gtagtaggtc actgagactt agaatggtct    3900
atccttgctc cctagcttag ggtgggatct tttaggcctt tgagcctagc aaggactcta    3960
gtctagggtc catcccatct cctgcaagaa tctctcaagg aaaggttgta gaaggaatga    4020
gagtagcaat ctatagcaag gatgatggtt gtagaatgag catgtaggta aggcatgaga    4080
tacttttacc tcgtaccttg taggcctata agactttgac ttataaaagt ctgtcctccc    4140
tagcctatat ggcctagaaa ataggacctt gaaagaatgc tatagtgagc ttatggccta    4200
catcctagag aatctaggta aaagatatta tgacttaggt actagagtac cagcaagcta    4260
gagcctatag ccccatccta cttcaaatct tagagtatag tacttcaaag atcatatact    4320
ctgactttag accatggcct tagaagaggt tagagtgagg gtcctccctt gcgaggtagg    4380
agagcatctt gagcttttag gagcatccta gcagctaggt ctagagaggg caagttagag    4440
aagtttgagt catgctagag ggcaaagtct cagcctcctt gtcctacaag agtcatctag    4500
gtatagctac atcaaactat catagaagtt tgattaccct gttatcccta aggaaccccct    4560 agtgatggag ttggccactc cctctctgcg cgctcgctcg ctcactgagg ccgggcgacc    4620
aaaggtcgcc cgacgcccgg gctttgcccg ggcggcctca gtgagcgagc gagcgcgcag    4680
ctgcctgcag g                                                         4691
```

<210> SEQ ID NO 20
<211> LENGTH: 7043
<212> TYPE: DNA
<213> ORGANISM: Artificial Sequence
<220> FEATURE:
<223> OTHER INFORMATION: Expression Vector

<400> SEQUENCE: 20

| | | | | | |
|---|---|---|---|---|---|
| taactataac | ggtcctaagg | tagcgagcga | tcgcttaatt | aaggccggcc | ggcctccgcg | 60 |
| ccgggttttg | gcgcctcccg | cgggcgcccc | cctcctcacg | gcgagcgctg | ccacgtcaga | 120 |
| cgaagggcgc | agcgagcgtc | ctgatccttc | cgcccggacg | ctcaggacag | cggcccgctg | 180 |
| ctcataagac | tcggccttag | aaccccagta | tcagcagaag | gacattttag | gacgggactt | 240 |
| gggtgactct | agggcactgg | ttttctttcc | agagagcgga | acaggcgagg | aaaagtagtc | 300 |
| ccttctcggc | gattctgcgg | agggatctcc | gtggggcggt | gaacgccgat | gattatataa | 360 |
| ggacgcgccg | ggtgtggcac | agctagttcc | gtcgcagccg | ggatttgggt | cgcggttctt | 420 |
| gtttgtggat | cgctgtgatc | gtcacttggt | gagtagcggg | ctgctgggct | gggtacgtgc | 480 |
| gctcggggtt | ggcgagtgtg | ttttgtgaag | ttttttaggc | accttttgaa | atgtaatcat | 540 |
| ttgggtcaat | atgtaatttt | cagtgttaga | ctagtaaatt | gtccgctaaa | ttctggccgt | 600 |
| ttttggcttt | tttgttagac | gcctgcaggg | gcgcgccacg | cgtcgaagaa | ggtgagtaat | 660 |
| cttaacatgc | tctttttttt | ttttttttgct | aatcccttttt | gtgtgctgat | gttaggatga | 720 |
| catttacaac | aaatgtttgt | tcctgacagg | aaaaaccttg | ctgggtacct | tcgttgccgg | 780 |
| acacttcttg | tcctctactt | tggaaaaaag | gaattgagag | ccgctagcgc | caccatgtgg | 840 |
| actctcgggc | gccgcgcagt | agccggcctc | ctggcgtcac | ccagcccagc | ccaggcccag | 900 |
| accctcaccc | gggtcccgcg | gccggcagag | ttggccccac | tctgcggccg | ccgtggcctg | 960 |
| cgcaccgaca | tcgatgcgac | ctgcacgccc | cgccgcgcaa | gttcgaacca | acgtggcctc | 1020 |
| aaccagattt | ggaatgtcaa | aaagcagagt | gtctatttga | tgaatttgag | gaaatctgga | 1080 |
| actttgggcc | acccaggctc | tctagatgag | accacctatg | aaagactagc | agaggaaacg | 1140 |
| ctggactctt | tagcagagtt | ttttgaagac | cttgcagaca | agccatacac | gtttgaggac | 1200 |
| tatgatgtct | cctttgggag | tggtgtctta | actgtcaaac | tgggtggaga | tctaggaacc | 1260 |
| tatgtgatca | acaagcagac | gccaaacaag | caaatctggc | tatcttctcc | atccagtgga | 1320 |
| cctaagcgtt | atgactggac | tgggaaaaac | tgggtgtact | cccacgacgg | cgtgtccctc | 1380 |
| catgagctgc | tggccgcaga | gctcactaaa | gccttaaaaa | ccaaactgga | cttgtcttcc | 1440 |
| ttggccctatt | ccgaaaaaga | tgcttgaatc | gattacgtag | cggccgcgtc | gactgatggg | 1500 |
| tggcatccct | gtgacccctc | cccagtgcct | ctcctggccc | tggaagttgc | cactccagtg | 1560 |
| cccaccagcc | ttgtcctaat | aaaattaagt | tgcatcattt | tgtctgacta | ggtgtccttc | 1620 |
| tataatatta | tggggtggag | gggggtggta | tggagcaagg | ggcaagttgg | gaagacaacc | 1680 |
| tgtagggcct | gcggggtcta | ttgggaacca | agctggagtg | cagtggcaca | atcttggctc | 1740 |
| actgcaatct | ccgcctcctg | ggttcaagcg | attctcctgc | ctcagcctcc | cgagttgttg | 1800 |
| ggattccagg | catgcatgac | caggctcagc | taattttttgt | ttttttggta | gagacggggt | 1860 |
| ttcaccatat | tggccaggct | ggtctccaac | tcctaatctc | aggtgatcta | cccaccttgg | 1920 |
| cctcccaaat | tgctgggatt | acaggcgtga | accactgctc | ccttccctgt | ccttctgatt | 1980 |
| ttaaaataac | tataccagca | ggaggacgtc | cagacacagc | ataggctacc | tggccatgcc | 2040 |
| caaccggtgg | gacatttgag | ttgcttgctt | ggcactgtcc | tctcatgcgt | tgggtccact | 2100 |

```
cagtagatgc ctgttgaatt atttaaatcg gtccgcgtac gttatggcta tagaatgccc    2160
catcttagat tgtaggtgac ttgagaggtc taagtccttc tataggatat ccttctaggt    2220
aggtataata ctagtctagg ttaaactagg ctagggagtc agagagcatt cgcaaagttt    2280
acctagtcta caagtctctc ccactatcct tgagcctacc ctaggctaga tcctaggaat    2340
catcccatgt cgtcattcta gctcatagca ctctcactat cctactagct aggccatctt    2400
cctaggaaaa gtataagatc ctagtttgat atagcatcaa tgtagctagt gggaaggata    2460
cggatgacct catagcttgc agcttttataa acttctcect cccataccac ctacctaggt    2520
gctatgaggt gactttagaa tcaccctcta ggaggtagac tatgatagtc cttccttcta    2580
gtatcaagat atcatctagc tacaagttat cgaaggttga cctaaccttta tagcaatatt    2640 ttgacctacc tgagagcttt agagcccctag tttgagagtc tatgtccatc tagggcctac    2700
ctaccttacc tactacatga tgtagctcta tcctagagcc ctctcatggt tatgagttgc    2760
ctgcaaggct agaatctagg aagatccttc catcatatcc ttgtagctat tttctacaat    2820
cgagaagagg tcctcctact tctaactttt gccattgccc catctagcta caaggttatg    2880
agagagagta taagtcatgc cataatacct aggtagaaat tctcacctat cctatttctt    2940
tctagcttgc agtgctacta gcatggggtg agatcttgag tctagccttt tgtcctaggg    3000
acttttagag cctaagactc tagagtgccc cgatctaata tccttctata acttcctacc    3060
agtctcttat agcctttgac cctatttcta ccacctactt cgcatggtct ttctttacct    3120
taccataaga ctgccttaga ctacctaggg agagacttaa ggccatgcta taagctatag    3180
gtctaggcta tatcctttca ccatatagca tgatcatagg cgcaaagtag aaaggactct    3240
aggatagaga ctctatagat gagcttgata ctgactttgt cgttactttg accctagtag    3300
ctcatactat catgatggtg actcttgagc cagtatgatc tttgtcctaa gtcccacccc    3360
atctttgcca cgctatagat ctgctctaag ctatagacca tccttgacct accttagagt    3420
ataggtcaaa ctctagacta gactttgtag gagggctata gcctttgccc catctcacct    3480
cactctctaa tatttctatg agcttttagg taaagtatct tctaaagcta tcctagggtc    3540
cttttacttc agcaagtgca aggagtcaaa tctcttactt taggcctagc aatcttaggt    3600
cgcaagaccc tctatagctc tcttctagct catagcatgg gataaccttc agtcaaaagt    3660
gctagacttg ctagagatgc tctagatagt ttgacctaag gtaggttaga aagtcacttt    3720
cgtccttttg tagtaggtca ctgagactta gaatggtcta tccttgctcc ctagcttagg    3780
gtgggatctt ttaggccttt gagcctagca aggactctag tctagggtcc atcccatctc    3840
ctgcaagaat ctctcaagga aaggttgtag aaggaatgag agtagcaatc tatagcaagg    3900
atgatggttg tagaatgagc atgtaggtaa ggcatgagat acttttacct cgtaccttgt    3960
aggcctataa gactttgact tataaaagtc tgtcctcect agcctatatg gcctagaaaa    4020
taggaccttg aaagaatgct atagtgagct tatggcctac atcctagaga atctaggtaa    4080
aagatattat gacttaggta ctagagtacc agcaagctag agcctatagc cccatcctac    4140
ttcaaatctt agagtatagt acttcaaaga tcatatactc tgactttaga ccatggcctt    4200
agaagaggtt agagtgaggg tcctcccttg cgaggtagga gagcatcttg agcttttagg    4260
agcatcctag cagctaggtc tagagagggc aagttagaga agtttgagtc atgctagagg    4320
gcaaagtctc agcctccttg tcctacaaga gtcatctagg tatagctaca tcaaaactatc    4380 atagaagttt gattaccctg ttatccctaa ggaaccccta gtgatggagt tggccactcc    4440
ctctctgcgc gctcgctcgc tcactgaggc cgggcgacca aaggtcgccc gacgcccggg    4500
```

```
ctttgcccgg gcggcctcag tgagcgagcg agcgcgcagc tgcctgcagg atctatgtcg    4560
ggtgcggaga aagaggtaat gaaatggcaa gtacttccgg aactataaat tgcgttgcgc    4620
tcactgcccg ctttccagtc gggaaacctg tcgtgccagc tgcataaatg aatcggccaa    4680
cgcgcgggga gaggcggttt gcgtattggg cgcgcttccg cttcctcgct cactgactcg    4740
ctgcgctcgg tcgttcggct gcggcgagcg gtatcagctc actcaaaggc ggtaatacgg    4800
ttatccacag aatcagggga taacgcagga agaacatgt gagcaaaagg ccagcaaaag    4860
gccaggaacc gtaaaaaggc cgcgttgctg gcgttttcc ataggctccg ccccctgac    4920 gagcatcaca aaatcgacg ctcaagtcag aggtggcgaa acccgacagg actataaaga    4980
taccaggcgt ttccccctgg aagctccctc gtgcgctctc ctgttccgac cctgccgctt    5040
accggatacc tgtccgcctt tctcccttcg ggaagcgtgg cgctttctca tagctcacgc    5100
tgtaggtatc tcagttcggt gtaggtcgtt cgctccaagc tgggctgtgt gcacgaaccc    5160
cccgttcagc ccgaccgctg cgccttatcc ggtaactatc gtcttgagtc aacccggta    5220 agacacgact tatcgccact ggcagcagcc actggtaaca ggattagcag agcgaggtat    5280
gtaggcggtg ctacagagtt cttgaagtgg tggcctaact acggctacac tagaagaaca    5340
gtatttggta tctgcgctct gctgaagcca gttaccttcg gaaaaagagt tggtagctct    5400
tgatccggca acaaaccac cgctggtagc ggtggttttt ttgtttgcaa gcagcagatt    5460
acgcgcagaa aaaaggatc tcaagaagat cctttgatct tttctacggg gtctgacgct    5520
cagtggaacg aaaactcacg ttaagggatt ttggtcatga gattatcaaa aaggatcttc    5580
acctagatcc ttttaaatta aaatgaagt tttaaatcaa tctaaagtat atatgagtaa    5640
acttggtctg acatgcgcag ttaccaatgc ttaatcagtg aggcacctat ctcagcgatc    5700
tgtctatttc gttcatccat agttgcctga ctccccgtcg tgtagataac tacgatacgg    5760
gagggcttac catctggccc cagtgctgca atgataccgc gagacccacg ctcaccggct    5820
ccagatttat cagcaataaa ccagccagcc ggaagcgccg agcgcagaag tggtcctgca    5880
actttatccg cctccatcca gtctattaac tgttgccggg aagctagagt aagtagttcg    5940
ccagttaata gtttgcggag cgttgttgcc attgctacag gcatcgtggt gtcacgctcg    6000
tcgtttggta tggcttcatt cagctccggt tcccaacgat caaggcgagt tacatgatcc    6060
cccatgttgt gcaaaaaagc ggttagctcc ttcggtcctc cgatggttgt cagaagtaag    6120
ttggccgcag tgttatcact catggttatg gcagcactgc ataattctct tactgtcatg    6180
ccatccgtaa gatgcttttc tgtgactggt gagtattcaa ccaagtcatt ctgagaatag    6240
tgtatgcggc gaccgagttg ctcttgcccg gcgtcaatac gggataatac cgcgccacat    6300
agcagaactt aaaagtgct catcattggg aagcgttctt cggggcgaaa actctcaagg    6360
atcttaccgc tgttgagatc cagttcgatg taacccacac gagcacccaa ctgatcttca    6420
gcatctttta ctttcaccag cgtttctggg tgagcaaaaa caggaaggca aaatgccgca    6480
aaaaagggaa taagggcgac acggaaatgt tgaatactca tactcttcct ttttcaatat    6540
tattgaagca tttatcaggg ttattgtctc atgagcggat acatatttga atgtatttag    6600
aaaaataaac aaatagggt tccgcgcaca tttccccgaa aagtgccacc tgaggtctaa    6660
gaaaccatta ttatcatgac attaacctat aaaaataggc gtatcacgag gccctttctt    6720
ctcgcgcgtt tcggtgatga cggtgaaaac ctctgacaca tgcagctccc ggatacggtc    6780
acagcttgtc tgtaagcgga tgccgggagc agacaagccc gtcagggcgc gtcagcgggt    6840
```

```
gttggcgggt gtcggggctg gcttaagctg agctaactat gactctctta aggtagccaa    6900
atcctgcagg cagctgcgcg ctcgctcgct cactgaggcc gcccgggcaa agcccgggcg    6960
tcgggcgacc tttggtcgcc cggcctcagt gagcgagcga gcgcgcagag agggagtggc    7020
caactccatc actaggggtt cct                                            7043
```